(12) United States Patent
Hoerr et al.

(10) Patent No.: US 10,441,653 B2
(45) Date of Patent: *Oct. 15, 2019

(54) NUCLEIC ACID COMPRISING $G_lX_mG_n$ AS AN IMMUNE-STIMULATING AGENT/ADJUVANT

(75) Inventors: Ingmar Hoerr, Tübingen (DE); Jochen Probst, Deizisau (DE); Thomas Ketterer, Tübingen (DE); Birgit Scheel, Tübingen (DE)

(73) Assignee: CureVac AG, Tübingen (DE)

(*) Notice: Subject to any disclaimer, the term of this patent is extended or adjusted under 35 U.S.C. 154(b) by 616 days.

This patent is subject to a terminal disclaimer.

(21) Appl. No.: 13/492,787

(22) Filed: Jun. 8, 2012

(65) Prior Publication Data

US 2013/0121988 A1 May 16, 2013

Related U.S. Application Data

(62) Division of application No. 12/375,178, filed as application No. PCT/EP2007/006772 on Jul. 31, 2007, now abandoned.

(60) Provisional application No. 60/942,740, filed on Jun. 8, 2007.

(30) Foreign Application Priority Data

Jul. 31, 2006 (DE) .................. 10 2006 035 618

(51) Int. Cl.
| | |
|---|---|
| A61K 39/39 | (2006.01) |
| C07H 21/02 | (2006.01) |
| C12N 15/117 | (2010.01) |
| A61K 39/00 | (2006.01) |

(52) U.S. Cl.
CPC ............ *A61K 39/39* (2013.01); *C07H 21/02* (2013.01); *C12N 15/117* (2013.01); *A61K 2039/55561* (2013.01); *C12N 2310/17* (2013.01); *C12N 2310/3515* (2013.01)

(58) Field of Classification Search
CPC .................. C12N 15/117; C12N 2310/17
See application file for complete search history.

(56) References Cited

U.S. PATENT DOCUMENTS

| | | | |
|---|---|---|---|
| 3,906,092 A | 9/1975 | Hilleman et al. |
| 4,373,071 A | 2/1983 | Itakura |
| 4,401,796 A | 8/1983 | Itakura |
| 4,415,732 A | 10/1983 | Caruthers et al. |
| 4,578,399 A | 3/1986 | Schorlemmer et al. |
| 5,516,652 A | 5/1996 | Abramovitz et al. |
| 5,663,153 A | 9/1997 | Hutcherson et al. |
| 5,663,163 A | 9/1997 | Takaya et al. |
| 5,844,075 A | 12/1998 | Kawakami et al. |
| 5,965,720 A | 10/1999 | Gryaznov et al. |
| 6,096,307 A | 8/2000 | Braswell et al. |
| 6,218,371 B1 | 4/2001 | Krieg et al. |
| 6,239,116 B1 | 5/2001 | Krieg et al. |
| 6,322,967 B1 | 11/2001 | Parkin |
| 6,406,705 B1 | 6/2002 | Davis et al. |
| 6,498,148 B1 | 12/2002 | Raz |
| 6,514,948 B1 | 2/2003 | Raz et al. |
| 6,552,006 B2 | 4/2003 | Raz et al. |
| 6,589,940 B1 | 7/2003 | Raz et al. |
| 6,610,661 B1 | 8/2003 | Carson et al. |
| 6,689,757 B1 | 2/2004 | Craig |
| 6,716,434 B1 | 4/2004 | Ansley et al. |
| 7,001,890 B1 | 2/2006 | Wagner et al. |
| 7,208,478 B2 | 4/2007 | Carson et al. |
| 7,407,944 B2 | 8/2008 | Agrawal et al. |
| 7,470,674 B2 | 12/2008 | Agrawal et al. |
| 7,517,862 B2 | 4/2009 | Agrawal et al. |
| 2003/0225016 A1 | 12/2003 | Fearon et al. |
| 2003/0232074 A1 | 12/2003 | Bauer |
| 2004/0006010 A1 | 1/2004 | Carson et al. |
| 2004/0006034 A1 | 1/2004 | Raz et al. |
| 2004/0047869 A1 | 3/2004 | Garcon et al. |
| 2004/0052763 A1 | 3/2004 | Mond et al. |
| 2005/0032730 A1 | 2/2005 | Von Der Mulbe et al. |
| 2005/0037494 A1 | 2/2005 | Hecker et al. |
| 2005/0059624 A1 | 3/2005 | Hoerr et al. |
| 2005/0130918 A1 | 6/2005 | Agrawal et al. |
| 2005/0250723 A1 | 11/2005 | Hoerr et al. |
| 2006/0172966 A1 | 8/2006 | Lipford et al. |
| 2006/0188490 A1 | 8/2006 | Hoerr et al. |
| 2007/0280929 A1 | 12/2007 | Hoerr et al. |
| 2008/0025944 A1 | 1/2008 | Hoerr et al. |
| 2008/0267873 A1 | 10/2008 | Hoerr et al. |
| 2009/0324584 A1 | 12/2009 | Hoerr et al. |

FOREIGN PATENT DOCUMENTS

| | | |
|---|---|---|
| AU | 776268 | 12/2000 |
| DE | 10148886 | 4/2003 |

(Continued)

OTHER PUBLICATIONS

Agrawal, 1996; Antisense oligonucleotides: towards clinical trials; Trends in Biotechnology; vol. 14; No. 10; pp. 376-387.

(Continued)

*Primary Examiner* — Jennifer Dunston
(74) *Attorney, Agent, or Firm* — Parker Highlander PLLC

(57) ABSTRACT

The present invention relates to a nucleic acid of the general formula (I): $G_lX_mG_n$, which may be modified by a lipid. The invention relates further to a pharmaceutical composition containing an immune-stimulating agent according to the invention in combination with a pharmaceutically active carrier/vehicle (and, optionally, further auxiliary substances, additives and/or further adjuvants). The present invention can relate to a vaccine, which corresponds to a pharmaceutical composition of the invention, wherein the pharmaceutically active component induces a specific immune response (e.g. an antigen). The present invention can relate to the use of a nucleic acid of the invention or a pharmaceutical composition according to the invention for the treatment of infectious diseases, autoimmune disease, allergies or cancer diseases.

33 Claims, 15 Drawing Sheets

Specification includes a Sequence Listing.

(56) References Cited

FOREIGN PATENT DOCUMENTS

| | | |
|---|---|---|
| DE | 69819150 | 7/2004 |
| DE | 102006007433 | 8/2007 |
| EP | 0347501 | 12/1989 |
| EP | 0772619 | 5/1997 |
| EP | 0839912 | 6/1998 |
| EP | 1083232 | 3/2001 |
| EP | 1167379 | 1/2002 |
| EP | 1374894 | 1/2004 |
| EP | 1393745 | 3/2004 |
| EP | 1564291 | 8/2005 |
| EP | 1905844 | 4/2008 |
| WO | WO1991/005560 | 5/1991 |
| WO | WO1994/017093 | 8/1994 |
| WO | WO1994/017792 | 8/1994 |
| WO | WO1999/053961 | 10/1999 |
| WO | WO2000/075304 | 12/2000 |
| WO | WO2001/004135 | 1/2001 |
| WO | WO2001/075164 | 10/2001 |
| WO | WO01/93902 | 12/2001 |
| WO | WO01/97843 | 12/2001 |
| WO | WO2002/000594 | 1/2002 |
| WO | WO2002/000694 | 1/2002 |
| WO | WO2002/078614 | 10/2002 |
| WO | WO2002/098443 | 12/2002 |
| WO | WO2003/028656 | 4/2003 |
| WO | WO2003/057822 | 7/2003 |
| WO | WO 2003-059381 | 7/2003 |
| WO | WO03/066649 | 8/2003 |
| WO | WO 2003-074551 | 9/2003 |
| WO | WO2003/086280 | 10/2003 |
| WO | WO2004/004743 | 1/2004 |
| WO | WO2004/058159 | 7/2004 |
| WO | WO2004/064782 | 8/2004 |
| WO | WO2004/092329 | 10/2004 |
| WO | WO 2005-000887 | 1/2005 |
| WO | WO2005/001022 | 1/2005 |
| WO | WO2005/030259 | 4/2005 |
| WO | WO 2005-030800 | 4/2005 |
| WO | WO2005/097993 | 10/2005 |
| WO | WO 2006/002538 | 1/2006 |
| WO | WO2006/029223 | 3/2006 |
| WO | WO2006/116458 | 11/2006 |
| WO | WO2007/031322 | 3/2007 |
| WO | WO 2007/031877 | 3/2007 |
| WO | WO2007/042554 | 4/2007 |
| WO | WO2007/051303 | 5/2007 |
| WO | WO2007/124755 | 11/2007 |
| WO | WO2008/014979 | 2/2008 |
| WO | WO 2008139262 A2 * | 11/2008 |
| WO | WO2009/030481 | 3/2009 |
| WO | WO2009/053700 | 4/2009 |
| WO | WO2009/086640 | 7/2009 |
| WO | WO2010/037408 | 4/2010 |

OTHER PUBLICATIONS

Ara et al., 2001; Zymosan enhances the immune response to DNA vaccine for human immunodeficiency virus type-1 through the activation of complement system; Immunology; vol. 103, pp. 98-108.
Bayard et al.; 1985; Antiviral activity in L1210 cells of liposome-encapsulated (2'-5')oligo(adenylate)analogues; Eur. J. Biochem., vol. 151, No. 2, pp. 319-326.
Bettinger T. et al, Peptide-mediated RNA deliveny: a novel approach for enhanced transfection of primary and Post-mitotic cells, Nucleic Acids Research, 2001, vol. 29, No. 18, 3882-3891.
Blaxter et al., 2002; The Brugia malayi genome project: expressed sequence tags and gene discovery; 2002; Transactions of the Royal Society of Tropical Medicine and Hygiene, vol. 96, No. 1, pp, 1-17.
Bocchia et al., 2000; Antitumor vaccination: where we stand; Heamatologica, vol. 85, No. 11, pp. 1172-1206.
Buteau et al., 2002; Challenges in the Development of Effective Peptide Vaccines for Cancer; Mayo Clin Proc, vol. 77. pp. 339-349.

CAPLUS accession No. 190686-49-8; Brugia malayi strain TRS Labs conle RRAMCA1537 EST; Chemical Abstracts Services; Database CAPLUS printed 2009.
EBI Database accession No. BP836659; Arabidopsis thaliana clone RAFL22-17-C17 EST; Database EMBL; 2005.
EBI Database accession No. CZ193289; PST12107-MICB1 Mus musculus genomic clone PST12107-NR; Database EMBL; 2005.
EBI Database accession No. DN868844; NEIBank analysis of Dog lens; Wistow, G., Database EMBL; 2005.
EMBL accession No. AA430815; Brugla malayi strain TRS Labs clone RRAMCA1537 EST; Database EMBL; 1997.
Feroze-Merzoug et al., 2001; Molecular profiling in prostate cancer, Cancer and Metastasis Reviews, vol. 20, pp. 185-171.
Fire et al., 1998; Potent and specific genetic interference by double-stranded RNA in Caenorhabditis elegans; Nature; vol. 391; pp. 806-811.
Fotin-Mleczek, Mariola et al: Messenger RNA-based vaccines with dual activity induce balanced TLR-7 dependent adaptive immune responses and provide antitumor activity, Journal of Immunotheraphy, Raven Press, NY, US, vo. 34, No. 1, Jan. 1, 2011, pp. 1-15.
Galbraith et al., 1994; Complement Activation and Hemodynamic Changes Following Intravenous Administration of Phosphorothioate Oligonucleotides in the Monkey; Antisense Research and Development; vol. 4, pp. 201-206.
Gao et al., 2007; Nonviral gene delivery what we know and what is next; The AAPS Journal, vol. 9, No. 1, pp. E92-104, XP02609380.
GenBank Accession No. JK489756.1, GI: , 346421249, publicly available Sep. 2011.
Georgieva et al., Comparative study on the changes in photosynthetic activity of the homoiochlorophyllous desiccation-tolerant Haberlea rhodopensis and desiccation-sensitive spinach leaves during desiccation and rehydration, Photosythesis Research, vol. 85, pp. 191-203, Aug. 2005.
Gryaznov, 1999; Oligonucleotide N3'-> P5' phosphoramidates as potential therapeutic agents; Biochimica et Biophysics Acta; vol. 1489, pp. 131-140.
Hardy et al., 2009; Synergistic effects on gene deiivery-co-formulation of small disulfide-linked dendritic polycations with Lipofectamine 2000; Organic & Biomolecular Chemistry, vol. 7, No. 4, pp. 789-793, XP002609381.
Hausch et al.; 1998; A novel carboxy-functionalized photocleavable dinucleotide analog for the selection fo RNA catalysts: Tetrahedron Letters, vol. 39, No. 34, pp. 6157-6158.
Heidenreich et al., 1993; Chemically modified RNA: approaches and applications; FASEB Journal; vol. 7 No. 1, pp. 90-96.
Herbert et al., The Dictionary of Immunology; Academic Press, 4th edition, 1995 entries for "v exon," "v-gene," "v-region," "vaccination," "vaccine," "vaccinia," and "valency".
Herbert et al.; 2005; Lipid modification of GRN163, an N3'- > P5' thio-phosphoramidate oligonucleotide, enhances the potency of telomerase inhibition; Oncogene; vol. 24; pp. 5262-5268.
Heymann, 1890; The immune complex: possible ways of regulating the antibody response; Immunology Today; vol. 11, No. 9, pp. 310-313.
Hoerr et al., 2000; In vivo application of RNA leads to induction of specific cytotoxic T lymphocytes and antibodies; Eur. J. Immunol., vol. 30, No. 1, pp. 1-7.
Janssen et al., 2003; Role of Toll-Like Receptors in Pathogen Recognition; Clinical Microbiology Reviews, vol. 16, No. 4; pp. 637-646.
Kim et al., 2009; VeGF siRNA delivery system using arginine-grafted bioreducible poly(dislfide amine); Molecular Pharmaceutics, vol. 6, No. 3, pp. 718-726, XP002609382.
Kwiatkowski et al., 1984; The 9-(4-Octadecyloxyphenylxanthen)-9-yl-Group. A new Acid-labile Hydroxyl Protective Group and 1st Application in the Preparative Reserve-phase Chromatographic Separation of Oligoribonucleotides; Acta Chemica Scandinavica; B38(8); pp. 657-671.
Lo et al., 2008: An endosomolytic Tat peptide produced by incorporation of histidine and cysteine residues as a nonviral vector for DNA transfection; Biomaterials, vol. 29, No. 15, pp. 2408-2414, XP022526913.

(56) References Cited

OTHER PUBLICATIONS

Lochmann et al.; 2004; Drug delivery of oligonucleotides by peptides; European Pharmaceutics and Biopharmaceutics; vol. 58, No. 2, pp. 237-251.
Mateo et al., 1999; An HLA-A2 Polyepitope Vaccine for Melanoma Immunotherapy; J Immunol, vol. 163, pp. 4058-4063.
Matray et al., 1999; Synthesis and properties of RNA analogs—oligoribonucleotide N3'-> P5' phosphoramidates; Nucleic Acids Research; vol. 27, No. 20, pp. 3976-3985.
McKenzie et al., 2000; A potent new class of reductively activated peptide gene delivery agents; Journal of Biological Chemistry, vol. 275, No. 14, pp. 9970-9977, XP002238140.
McKenzie et al., 2000; Low molecular weight disulfide cross-linking peptides as nonviral gene delivery carriers; Bioconjugate Chemistry, vol. 11, No. 6, pp. 901-909, XP002609379.
Milich et al., 1997; The Hepatitis B Virus Core and e Antigens Elicit Different Th Cell Subsets: Antigen Strucutre Can Affect TH Cell Phenotype; Journal of Virology, vol. 71, No. 3, pp. 2192-2201.
Minks et al., 1979; Structural requirements of Double-stranded RNA for the Activation of 2',5'-Oligo(A) Polymerase and Protein Kinase of Interferon-treated HeLa Cells; The Journal of Biological Chemistry; vol. 254, No. 20; pp. 10180-10183.
Miyata et al., 2004; Block Catiomer Polyplexes with Regulated Densities of Charge and Disulfide Cross-Linking Directed to Enhance Gene Expression; Journal of the American Chemical Society, vol. 126, No. 8, pp. 2355-2361, XP002993261.
Nicholson et al., 1988; Accurate in vitro cleavage by Rnase III of phosphothioate-substituted RNA processing signals in bacteriophage T7 early mRNA; Nucleic Acids Res., vol. 16, No. 4, pp. 1577-1591.
Parkinson et al., 2004, A transcriptomic analysis of the phylum Nematoda; Nature Genetics, vol. 36, No. 12, pp. 1259-1267.
Ramazeilles et al., 1994; Antisense phosphorothioate oligonucleotides: Selective killing of the intracellular parasite *Leishmania amazonensis*; Proc. Natl. Acad. Sci., vol. 91, pp. 7859-7863.
Read et al; 2003; Vectors based on reducible polycations facilitate intracellular release of nucleic acids; Journal of Gene Medicine, vol. 5 No. 3, pp. 232-245, XP002481542.
Read et al; 2005; A versatile reducible polycationic-based system for effeicient delivery of a broad range of nucleic acids; Nucleic acids research, vol. 33 No. 9, pp. 1-16; XP002447464.
Riedl et al., 2002; Priming Th1 Immunity to Voral Core Particles Is Facilitated by Trace Amounts of RNA Bound to 1st Arginine-Rich Domain; The Journal of Immunology, vol. 168, pp. 4951-4959.
Romagne F., Current and future drugs targeting one class of innate immunity receptors: the Toll-like receptors, Drug Discov Today. Jan. 2007;12(1-2):80-7. Epub Nov. 28, 2006.
Saenz-Badillos, 2001; RNA as a tumor vaccine: a review of the literature; Exp. Dermatol.; vol. 10, No. 3, pp. 143-154.
Scheel et al., 2003; mRNA as immmunostimulatory molecule; Krebsimmuntherapie—Annual Meeting 2003; Abstract (online publication, http://www.kimt.de/archiv/abstracts/htm ) Session 5 Abstract 10.
Schirrmacher et al., 2000; Intra-pinna anti-tumor vaccination with self-replicating infectious RNA or with DANN encoding a model tumor antigen and a cytokine; Gene Therapy, vol. 7 No. 13, pp. 1137-1147.
Shea et al., 1990, Synthesis, hybridization properties and antiviral activity of lipid-oligodeoxynucleotide conjugates; Nucleic Acids Research; vol. 18, No. 13, pp. 3777-3783.
Stephens et al., Sequence analysis of the major outer membrane protein gene from Chlamydia trachomatis serovar L2, Journal of Bacteriology, vol. 168, No. 3, pp. 1277-1282, Dec. 1986.
Takae et al., 2008: PEG-detachable polyplex micelles based on disulfide-linked block catiomers as bioresponsive nonviral gene vectors; Journal of the American Chemical Society, vol. 130, No. 18, pp. 6011-6009, XP002609383.
Teplova et al., 1999; Crystal structure and improved antisense properties of 2'-O-2-methoxyethyl)-RNA; Nature Structural Biology; vol. 6, No. 6, pp. 535-539.
Tokunaga et al., 2004; Effect of oligopeptides on gene expression: comparison of DNA/peptide and DNA/peptide/liposome complexes; International Journal of Pharmaceutics, vol. 269, No. 1, pp. 71-80, XP002609384.
Trinchieri et al., 2007; Cooperation of Toll-like receptor signals in innate immune defence; Nature Reviews Immunology; vol. 7, Mar. 2007; pp. 179-190.
Tse K et al., Update on toll-like receptor-directed therapies for human disease, Ann Rheum Dis. Nov. 2007;66 Suppl 3:iii77-80. Review.
Zhou et al., 1999; RNA Melanoma Vaccine: Induction of Antitumor Immunity by Human Glycoprotein 100 mRNA Immunization; Human Gene Therapy; vol. 10; pp. 2719-2724.
Zimmermann S et al., Immunostimulatory DNA as adjuvant: efficacy of phosphodiester CpG oligonucleotides is enhanced by 3' sequence modifications, Vaccine. Feb. 14, 2003;21(9-10):990-5. (only abstract).
Machine-generated English translation of EP1564291 (Document B11). printed as 16 pages on May 25, 2012.
Hell, et al., "Species-specific recognition of single-stranded RNA via Toll-like receptor 7 and 8," Science 303, Mar. 5, 2004, pp. 1526-1529.
Diebold, et al., "Innate antiviral responses by means of TLR7-mediated recognition of single-stranded RNA," Science 303, Mar. 5, 2004, pp. 1429-1531.
Adams, et al., "Preparation and hybridization properties of oligonucleotides containing 1-alpha-D arabinofuranosylthymine," Nucleic Acid Research 19(13), 1991, pp. 3647-3651.
Scheel, et al., "Therapeutic anti-tumor immunity triggered by injections of immunostimulating single-stranded RNA," European Journal of Immunology 36(10), Oct. 2006, pp. 2807-2816.
Scheel, et al., "Toll-like receptor-dependent activation of several human blood cells types by protamine-condensed mRNA," European Journal of Immunology 35(5), May 2005, pp. 1557-1566.
Scheel, et al., "Immunostimulating capacities of stabilized RNA molecules," European Journal of Immunology 34(2), 2004, pp. 537-547.
"Cell-penetrating peptide," Wikipedia, located at http://en.wikipedia.org/wiki/cell-penetrating_peptide, downloaded on Dec. 11, 2012.
"DOC/Alum Complex," Violin: Vaccine investigation and online information network, located at http://www.violinet.org/vaxjo/vaxjo_detail.php?c_vaxjo_id=49, downloaded on Aug. 28, 2012.
"QS21," Wikipedia, located at http://en.wikipedia.org/wiki/QS21, downloaded on Dec. 11, 2012.
"Ribi vaccine adjuvant," Violin: Vaccine investigation and online information network, located at http://www.violinet.org/vaxjo/vaxjo_detail.php?c_vaxjo_id=21, downloaded on Dec. 17, 2012.
"SPT (Antigen Formulation)," Violin: Vaccine investigation and online information network, located at http://www.violinet.org/vaxjo/vaxjo_detail.php?c_vaxjo_id=72, downloaded on Aug. 21, 2012.
"Virus-like particle," Wikipedia, located at http://en.wikipedia.org/wiki/virus-like_particle, downloaded on Sep. 3, 2012.
Berzofsky et al., "Progress on new vaccine strategies against chronic viral infections," *J. Clin. Invest.*, 114(4):450-462, 2004.
Cooper et al., "CPG 7909 adjuvant improves hepatitis B virus vaccine seroprotection in antiretroviral-treated HIV-infected adults," *AIDS*, 19:1473-1479, 2005.
Dmitriev, "Bactenecin 7 peptide fragment as a tool for intracellular delivery of a phosphorescent oxygen sensor," *FEBS Journal*, 277:4651-4661, 2010.
Fox, "Squalene emulsions for parenteral vaccine and drug delivery," *Molecules*, 14:3286-3312, 2009.
Huang et al., "Recent development of therapeutics for chronic HCV infection," *Antiviral Res.*, 71(2-3):351-362, 2006.
Huget et al., "Adjuvant and suppressor activity of the polycation protamine hydrochloride in the primary immune response of mice," *Z Immunitatsforsch Immunobiol.*, 152(3):190-199, 1976.
Kilk, "Cell-penetrating peptides and bioactive cargoes. Strategies and mechanisms," *Department of Neurochemistry and Neurotoxicology Arrhenius Laboratories of Natural Sciences, Stockholm University*, 2004.

(56) References Cited

OTHER PUBLICATIONS

Koziel et al., "Hepatitis C virus (HCV)-specific cytotoxic T lymphocytes recognize epitopes in the core and envelope proteins of HCV," *J. Virol.*, 67(12):7522-7532, 1993.

Racanelli et al., "Presentation of HCV antigens to naive CD8+T cells: why the where, when, what and how are important for virus control and infection outcome," *Clin Immunol.*, 124(1):5-12, 2007.

Rittner et al., "New basic membrane-destabilizing peptides for plasmid-based gene delivery in vitro and in vivo," *Molecular Therapy*, 5(2):104-114, 2002.

Rollier et al., "Control of heterologous hepatitis C virus infection in chimpanzees is associated with the quality of vaccine-induced peripheral T-helper immune response," *J. Virol.*, 78(1):187-196, 2004.

Shiffman et al., "Protein dissociation from DNA in model systems and chromatin," *Nucleic Acids Res.*, 5(9):3409-3426, 1978.

Shirai et al., "An epitope in hepatitis C virus core region recognized by cytotoxic T cells in mice and humans," *J. Virol.*, 68(5):3334-3342, 1994.

Sun et al., "Advances in saponin-based adjuvants," *Vaccine*, 27:1787-1796, 2009.

Tan et al., "Strategies for hepatitis C therapeutic intervention: now and next," *Curr Opin Pharmacol.*, 4(5):465-470, 2004.

Wyman et al., "Design, synthesis, and characterization of a cationic peptide that binds to nucleic acids and permeabilizes bilayers," *Biochemistry*, 36:3008-3017, 1997.

Zohra et al., "Effective delivery with enhanced translational activity synergistically accelerates mRNA-based transfection," *Biochem Biophys Res Commun.*, 358(1):373-378, 2007.

Alexopoulou et al., "Recognition of double-stranded RNA and activation of NF-kB by toll-like receptor 3", *Nature*, 413:732-738, 2001.

Grzelinski et al., "RNA interference-mediated gene silencing of pleiotrophin through polyethylenimine-complexed small interfering RNAs in vivo exerts antitumoral effects in glioblastoma xenografts", *Human Gene Therapy*, 17:751-766, 2006.

Hornung et al., "Sequence-specific potent induction of IFN-alpha by short interfering RNA in plasmacytoid dendritic cells through TLR7", *Nature Medicine*, 11(3):263-270, 2005.

Jacobs et al., "When two strands are better than one: the mediators and modulators of the cellular responses to double-stranded RNA", *Virology*, 219(2):339-349, 1996.

Judge et al., "Design of noninflammatory synthetic siRNA mediating potent gene silencing in vivo", *Molecular Therapy*, 13(3):494-505, 2006.

Ma et al., "Cationic lipids enhance siRNA-mediated interferon response in mice", *Biochemical and Biophysical Research Communications*, 330(3):755-759, 2005.

\* cited by examiner

SEQUENCE LISTING

<160> NUMBER OF SEQ ID NOS: 94

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 1
gguuuuuuuu uuuuuuuggg                                             20

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 2 gggggguuuuu uuuuugggggg                                           20

<210> SEQ ID NO 3
<211> LENGTH: 40
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 3
ggggguuuuu uuuuuuuuuu uuuuuuuuuu uuuuuggggg                       40

<210> SEQ ID NO 4
<211> LENGTH: 39
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 4
gugugugugu guuuuuuuuu uuuuuuugug ugugugugu                        39

<210> SEQ ID NO 5
<211> LENGTH: 39
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 5
gguugguugg uuuuuuuuuu uuuuuuugguu ugguugguu                       39

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic

```
        immune-stimulating oligonucleotide of formula (I)
        according to the invention

<400> SEQUENCE: 6
gggggggggu uugggggggg                                              20

<210> SEQ ID NO 7
<211> LENGTH: 20
<212> TYPE: RNA
<213> ORGANISM: Artificial Sequence
<220> FEATURE:
<223> OTHER INFORMATION: Description of Artificial Sequence: Synthetic
        immune-stimulating oligonucleotide of formula (I)
        according to the invention

<400> SEQUENCE: 7 ggggggggguu uugggggggg                                             20

<210> SEQ ID NO 8
<211> LENGTH: 20
<212> TYPE: RNA
<213> ORGANISM: Artificial Sequence
<220> FEATURE:
<223> OTHER INFORMATION: Description of Artificial Sequence: Synthetic
        immune-stimulating oligonucleotide of formula (I)
        according to the invention

<400> SEQUENCE: 8 gggggggguuu uuugggggggg                                            20

<210> SEQ ID NO 9
<211> LENGTH: 20
<212> TYPE: RNA
<213> ORGANISM: Artificial Sequence
<220> FEATURE:
<223> OTHER INFORMATION: Description of Artificial Sequence: Synthetic
        immune-stimulating oligonucleotide of formula (I)
        according to the invention

<400> SEQUENCE: 9
ggggggguuu uuuuggggggg                                             20

<210> SEQ ID NO 10
<211> LENGTH: 20
<212> TYPE: RNA
<213> ORGANISM: Artificial Sequence
<220> FEATURE:
<223> OTHER INFORMATION: Description of Artificial Sequence: Synthetic
        immune-stimulating oligonucleotide of formula (I)
        according to the invention

<400> SEQUENCE: 10
gggggguuuu uuuuggggggg                                             20

<210> SEQ ID NO 11
<211> LENGTH: 20
<212> TYPE: RNA
<213> ORGANISM: Artificial Sequence
<220> FEATURE:
<223> OTHER INFORMATION: Description of Artificial Sequence: Synthetic
        immune-stimulating oligonucleotide of formula (I)
        according to the invention

<400> SEQUENCE: 11
gggggguuuu uuuuugggggg                                             20

<210> SEQ ID NO 12
```

```
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 12
gggggguuuu uuuuuugggg                                                    20

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 13
ggggguuuuu uuuuuugggg                                                    20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 14
ggggguuuuu uuuuuuuggg                                                    20

<210> SEQ ID NO 15
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 15
gggguuuuuu uuuuuuuggg                                                    20

<210> SEQ ID NO 16
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 16
gggguuuuuu uuuuuuuugg                                                    20

<210> SEQ ID NO 17
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 17
```

-continued gguuuuuuuu uuuuuuuugg                                          20

<210> SEQ ID NO 18
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 18
guuuuuuuuu uuuuuuuuug                                          20

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 19
gggggggggg uuugggggggg gg                                      22

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 20 ggggggggggu uugggggggg gg                                      22

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 21
gggggggguu uuugggggggg gg                                      22

<210> SEQ ID NO 22
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 22
gggggggguu uuuugggggg gg                                       22

<210> SEQ ID NO 23
<211> LENGTH: 22
<212> TYPE: RNA
<213> ORGANISM: Artificial Sequence
<220> FEATURE:

<223> OTHER INFORMATION: Description of Artificial Sequence: Synthetic
      immune-stimulating oligonucleotide of formula (I)
      according to the invention

<400> SEQUENCE: 23
ggggggguuu uuuuuggggg gg                                              22

<210> SEQ ID NO 24
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 24
ggggggguuu uuuuuugggg gg                                              22

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 25
ggggggguuu uuuuuuuggg gg                                              22

<210> SEQ ID NO 26
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 26
gggggguuuu uuuuuuuggg gg                                              22

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 27
gggggguuuu uuuuuuuugg gg                                              22

<210> SEQ ID NO 28
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 28
gggggguuuu uuuuuuuugg gg                                              22

```
<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 29
ggggguuuuu uuuuuuuuug gg                                          22

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 30
ggguuuuuuu uuuuuuuuug gg                                          22

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 31
gguuuuuuuu uuuuuuuuuu gg                                          22

<210> SEQ ID NO 32
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 32
gggggggggg guuugggggg gggg                                        24

<210> SEQ ID NO 33
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 33
gggggggggg uuuugggggg gggg                                        24

<210> SEQ ID NO 34
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention
```

```
<400> SEQUENCE: 34
gggggggggu uuuuugggg gggg                                          24

<210> SEQ ID NO 35
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 35
gggggggggu uuuuuggggg gggg                                         24

<210> SEQ ID NO 36
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 36 ggggggggguu uuuuugggg gggg                                         24

<210> SEQ ID NO 37
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 37
gggggggguu uuuuuuggg gggg                                          24

<210> SEQ ID NO 38
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 38
gggggggguu uuuuuuugg gggg                                          24

<210> SEQ ID NO 39
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 39
ggggggguuu uuuuuuugg gggg                                          24

<210> SEQ ID NO 40
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      immune-stimulating oligonucleotide of formula (I)
      according to the invention

<400> SEQUENCE: 40
ggggggguuu uuuuuuuug gggg                                              24

<210> SEQ ID NO 41
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 41
gggggguuuu uuuuuuuug gggg                                              24

<210> SEQ ID NO 42
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 42
gggggguuuu uuuuuuuuu gggg                                              24

<210> SEQ ID NO 43
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 43
gggguuuuuu uuuuuuuuu gggg                                              24

<210> SEQ ID NO 44
<211> LENGTH: 24
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 44
ggguuuuuuu uuuuuuuuu uggg                                              24

<210> SEQ ID NO 45
<211> LENGTH: 32
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 45
guuuuuuuuu uuuuuuuuuu uuuuuuuuuu ug                                    32
```

```
<210> SEQ ID NO 46
<211> LENGTH: 34
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 46
gguuuuuuuu uuuuuuuuuu uuuuuuuuuu uugg                                 34

<210> SEQ ID NO 47
<211> LENGTH: 36
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 47
ggguuuuuuu uuuuuuuuuu uuuuuuuuuu uuuggg                               36

<210> SEQ ID NO 48
<211> LENGTH: 37
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 48
gggguuuuuu uuuuuuuuuu uuuuuuuuuu uuuuggg                              37

<210> SEQ ID NO 49
<211> LENGTH: 39
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 49 gggggguuuuu uuuuuuuuuu uuuuuuuuuu uuuuggggg                           39

<210> SEQ ID NO 50
<211> LENGTH: 41
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 50
gggggguuuu uuuuuuuuuu uuuuuuuuuu uuuuuggggg g                         41

<210> SEQ ID NO 51
<211> LENGTH: 43
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention
```

<400> SEQUENCE: 51
ggggggguuu uuuuuuuuu uuuuuuuuuu uuuuuuuggg ggg    43

<210> SEQ ID NO 52
<211> LENGTH: 45
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 52
gggggggguu uuuuuuuuuu uuuuuuuuuu uuuuuuugg ggggg    45

<210> SEQ ID NO 53
<211> LENGTH: 47
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 53 ggggggggu uuuuuuuuu uuuuuuuuuu uuuuuuuug ggggggg    47

<210> SEQ ID NO 54
<211> LENGTH: 7
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 54 gguuugg    7

<210> SEQ ID NO 55
<211> LENGTH: 8
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 55 gguuuugg    8

<210> SEQ ID NO 56
<211> LENGTH: 9
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 56 gguuuuugg    9

<210> SEQ ID NO 57
<211> LENGTH: 10
<212> TYPE: RNA

```
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 57
gguuuuuugg                                                               10

<210> SEQ ID NO 58
<211> LENGTH: 11
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 58
gguuuuuuug g                                                             11

<210> SEQ ID NO 59
<211> LENGTH: 12
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 59
gguuuuuuuu gg                                                            12

<210> SEQ ID NO 60
<211> LENGTH: 13
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 60
gguuuuuuuu ugg                                                           13

<210> SEQ ID NO 61
<211> LENGTH: 14
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 61
gguuuuuuuu uugg                                                          14

<210> SEQ ID NO 62
<211> LENGTH: 15
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 62
gguuuuuuuu uuugg                                                         15
```

<210> SEQ ID NO 63
<211> LENGTH: 16
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 63
gguuuuuuuu uuuugg                                                    16

<210> SEQ ID NO 64
<211> LENGTH: 17
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 64
gguuuuuuuu uuuuugg                                                   17

<210> SEQ ID NO 65
<211> LENGTH: 18
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 65
gguuuuuuuu uuuuuugg                                                  18

<210> SEQ ID NO 66
<211> LENGTH: 19
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 66
gguuuuuuuu uuuuuuugg                                                 19

<210> SEQ ID NO 67
<211> LENGTH: 9
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 67 ggguuuggg                                                             9

<210> SEQ ID NO 68
<211> LENGTH: 10
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)

according to the invention

<400> SEQUENCE: 68
ggguuuuggg                                                          10

<210> SEQ ID NO 69
<211> LENGTH: 11
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 69
ggguuuuugg g                                                        11

<210> SEQ ID NO 70
<211> LENGTH: 12
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 70
ggguuuuuug gg                                                       12

<210> SEQ ID NO 71
<211> LENGTH: 13
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 71
ggguuuuuuu ggg                                                      13

<210> SEQ ID NO 72
<211> LENGTH: 14
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 72
ggguuuuuuu uggg                                                     14

<210> SEQ ID NO 73
<211> LENGTH: 15
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 73
ggguuuuuuu uuggg                                                    15

<210> SEQ ID NO 74
<211> LENGTH: 16

-continued

```
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 74
ggguuuuuuu uuuggg                                                     16

<210> SEQ ID NO 75
<211> LENGTH: 17
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 75
ggguuuuuuu uuuuggg                                                    17

<210> SEQ ID NO 76
<211> LENGTH: 18
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 76
ggguuuuuuu uuuuuggg                                                   18

<210> SEQ ID NO 77
<211> LENGTH: 19
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 77
ggguuuuuuu uuuuuuggg                                                  19

<210> SEQ ID NO 78
<211> LENGTH: 57
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 78
ggguuuuuuu uuuuuuugg guuuuuuuuu uuuuugggu uuuuuuuuu uuuggg            57

<210> SEQ ID NO 79
<211> LENGTH: 42
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (I)
      according to the invention

<400> SEQUENCE: 79
```
gggguuuuuu uuuuuuuugg ggggguuuuuu uuuuuuuug gg 42

<210> SEQ ID NO 80
<211> LENGTH: 51
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (II)
      according to the invention

<400> SEQUENCE: 80
ggguuugggu uuggguuugg guuuggguuu ggguuugggu uuggguuugg g       51

<210> SEQ ID NO 81
<211> LENGTH: 57
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (II)
      according to the invention

<400> SEQUENCE: 81
cccuuuuuuu uuuuuuuucc cuuuuuuuuu uuuuuucccu uuuuuuuuuu uuucccc    57

<210> SEQ ID NO 82
<211> LENGTH: 51
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (II)
      according to the invention

<400> SEQUENCE: 82
cccuuucccu uucccuuucc cuuucccuuu cccuuucccu uucccuuucc c       51

<210> SEQ ID NO 83
<211> LENGTH: 42
<212> TYPE: RNA
<213> ORGANISM: Artificial Sequence
<220> FEATURE:
<223> OTHER INFORMATION: Description of Artificial Sequence: Synthetic
      immune-stimulating oligonucleotide of formula (II)
      according to the invention

<400> SEQUENCE: 83
cccuuuuuuu uuuuuuuucc ccccuuuuuu uuuuuuuuc cc       42

<210> SEQ ID NO 84
<211> LENGTH: 13
<212> TYPE: RNA
<213> ORGANISM: Artificial Sequence
<220> FEATURE:
<223> OTHER INFORMATION: Description of Artificial Sequence: Synthetic
      kozak oligonucleotide

<400> SEQUENCE: 84
gccgccacca ugg       13

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      protamin P1 peptide

```
<400> SEQUENCE: 85

Ser Arg Ser Arg Tyr Tyr Arg Gln Arg Gln Ser Arg Arg Arg
1               5                   10                  15

Arg Arg

<210> SEQ ID NO 86
<211> LENGTH: 21
<212> TYPE: PRT
<213> ORGANISM: Artificial Sequence
<220> FEATURE:
<223> OTHER INFORMATION: Description of Artificial Sequence: Synthetic
      protamin P2 peptide

<400> SEQUENCE: 86

Arg Arg Arg Leu His Arg Ile His Arg Arg Gln His Arg Ser Cys Arg
1               5                   10                  15

Arg Arg Lys Arg Arg
            20

<210> SEQ ID NO 87
<211> LENGTH: 20
<212> TYPE: RNA
<213> ORGANISM: Artificial Sequence
<220> FEATURE:
<223> OTHER INFORMATION: Description of Artificial Sequence: Synthetic
      immune-stimulating oligonucleotide RNA40

<400> SEQUENCE: 87
gcccgucugu ugugugacuc                                               20

<210> SEQ ID NO 88
<211> LENGTH: 15
<212> TYPE: RNA
<213> ORGANISM: Artificial Sequence
<220> FEATURE:
<223> OTHER INFORMATION: Description of Artificial Sequence: Synthetic
      stabilizing oligonucleotide
<220> FEATURE:
<221> NAME/KEY: modified_base
<222> LOCATION: (1)..(1)
<223> OTHER INFORMATION: c or u
<220> FEATURE:
<221> NAME/KEY: modified_base
<222> LOCATION: (5)..(5)
<223> OTHER INFORMATION: a, c, u, g, unknown or other
<220> FEATURE:
<221> NAME/KEY: modified_base
<222> LOCATION: (9)..( 9)
<223> OTHER INFORMATION: u or a
<220> FEATURE:
<221> NAME/KEY: modified_base
<222> LOCATION: (10)..(10)
<223> OTHER INFORMATION: Pyrimidine
<220> FEATURE:
<221> NAME/KEY: modified_base
<222> LOCATION: (13)..(13)
<223> OTHER INFORMATION: c or u
<220> FEATURE:
<223> OTHER INFORMATION: see specification as filed for detailed
      description of substitutions and preferred embodiments

<400> SEQUENCE: 88
nccancccnn ucncc                                                    15

<210> SEQ ID NO 89
<211> LENGTH: 10
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 89
uuuaauuuuc                                                              10

<210> SEQ ID NO 90
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
uuuuguuuua                                                              10

<210> SEQ ID NO 91
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
uuuguuuguu                                                              10

<210> SEQ ID NO 92
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
uuguuuuguu                                                              10

<210> SEQ ID NO 93
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
uuuuuuuuuu                                                              10

<210> SEQ ID NO 94
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
tgctcccccc tggtc                                                        15
```

NUCLEIC ACID COMPRISING $G_lX_mG_n$ AS AN IMMUNE-STIMULATING AGENT/ADJUVANT

RELATED APPLICATIONS

This application is a divisional application of U.S. application Ser. No. 12/375,178 filed on Sep. 2, 2009, now abandoned, which is a national stage application (under 35 U.S.C. 371) of PCT/EP2007/006772, filed on Jul. 31, 2007, and claim is made to benefit of German application 102006035618.7 filed Jul. 31, 2006 and U.S. provisional application 60/942,740 filed Jun. 8, 2007, the entirety of all which is incorporated by reference herein.

INCORPORATION OF SEQUENCE LISTING

The instant application contains a Sequence Listing which has been submitted in ASCII format via EFS-Web and is hereby incorporated by reference in its entirety. Said ASCII copy, created on Jul. 29, 2019, is named CRVCP0040USC1.txt and is 29 KB (as measured in Microsoft Windows®) in size.

The present invention relates to a nucleic acid of the general formula (I): $G_lX_mG_n$, or (II): $C_lX_mC_n$, optionally modified by a lipid, preferably used as such as an immune-stimulating agent or, alternatively, in combination with other biologically active agents, whereby the immune-stimulating agent of the invention acts as an adjuvant in the composition, which may optionally be combined with further adjuvants. Accordingly, the invention relates also to a pharmaceutical composition or to a vaccine, each containing nucleic acids of formulae (I) and/or (II) as an immune-stimulating agent. If the pharmaceutical composition contains the immune-stimulating agent of the invention as an adjuvant, the pharmaceutical composition contains at least one additional pharmaceutically active component, e.g. an antigenic agent. The pharmaceutical composition of the invention may typically contain a pharmaceutically acceptable carrier and, optionally, further auxiliary substances, additives and/or further adjuvants. The present invention relates likewise to the use of a pharmaceutical composition or of a vaccine according to the invention for the treatment of infectious diseases, cancer diseases, allergies and autoimmune diseases. Likewise, the present invention includes the use of the immune-stimulating adjuvant according to the invention for the preparation of a pharmaceutical composition for the treatment of cancer diseases, infectious diseases, allergies and autoimmune diseases.

In both conventional and genetic vaccination, the problem frequently occurs that only a small and therefore frequently inadequate immune response is brought about in the organism to be treated or inoculated. For this reason, so-called adjuvants are frequently added to vaccines or pharmaceutically active components, that is to say substances or compositions that are able to increase and/or influence in a targeted manner an immune response, for example to an antigen. For example, it is known that the effectiveness of some injectable medicinal active ingredients can be improved significantly by combining the active ingredient with an adjuvant which is capable of influencing the release of the active ingredient into the host cell system and optionally its uptake into the host cells. In this manner it is possible to achieve an effect that is comparable to the periodic administration of many small doses at regular intervals. The term "adjuvant" conventionally refers in this context to a compound or composition that serves as binder, carrier or auxiliary substance for immunogens and/or other pharmaceutically active compounds.

A number of compounds and compositions have been proposed as adjuvants in the art, for example Freund's adjuvant, metal oxides (aluminium hydroxide, etc.), alum, inorganic chelates or salts thereof, various paraffin-like oils, synthetic resins, alginates, mucoids, polysaccharide compounds, caseinates, as well as compounds isolated from blood and/or blood clots, such as, for example, fibrin derivatives, etc. However, such adjuvants in most cases produce undesirable side-effects, for example skin irritation and inflammation at the site of administration. Furthermore, toxic side-effects, in particular tissue necroses, are also observed. Finally, these known adjuvants in most cases bring about only inadequate stimulation of the cellular immune response, because only B-cells are activated.

For example, alums, metal oxides and chelates of salts have been associated with the generation of sterile abscesses. In addition, there are doubts among scientific experts that such compounds are excreted again fully. It is assumed, rather, that they result in undesirable inorganic residues in the body. Although such compounds usually have low toxicity, it is possible for them to be phagocyted by the cells of the reticulo-endothelial system (littoral and sinusoidal cells of the liver and spleen) as part of the insoluble debris. Furthermore, there are indications that such debris can have a damaging effect on the various filter mechanisms of the body, for example the kidneys, the liver or the spleen. Such residues accordingly represent a latent, ever present source of risk in the body and, generally, for the immune system.

The synthetic oils and petroleum derivatives used as adjuvants in the prior art likewise lead to adverse effects. However, these compounds are undesirable in particular because they metabolise rapidly in the body and decompose into their aromatic hydrocarbon compounds. It is known, however, that such aromatic hydrocarbon compounds can have a carcinogenic action to the greatest degree and/or can lead to irreparable DNA damage in other ways, for example by intercalation into the DNA. Moreover, it has been demonstrated that such compounds are likewise associated with the formation of sterile abscesses and can rarely be removed from the body again completely.

Compounds isolated from animals, such as, for example, gelatin, are also frequently unsuitable as adjuvants for the purpose of immune stimulation. Although such compounds do not usually have a destructive action on the host organism or the host cells in question, they typically migrate too rapidly from the injection site into the host organism or into the host cells, so that the properties generally desired for an adjuvant, such as, for example, delayed release of an active ingredient optionally injected together with the adjuvant, etc., are seldom achieved. Such rapid distribution can in some cases be counteracted with tannins or other (inorganic) compounds. The metabolism of such additional compounds and their whereabouts in the body have not been fully explained, however. In this case too, therefore, it is reasonable to assume that these compounds accumulate in the debris and thus considerably interfere with the filtration mechanisms, for example the kidney, liver and/or spleen cells. Also, the property of gelatin of swelling when administered parenterally can lead under in vivo conditions to unpleasant side-effects, such as, for example, swelling, in particular at the site of administration, and to a feeling of illness.

In the case of compounds isolated from blood and/or blood clots, such as, for example, fibrin derivatives, etc., immune-stimulating effects have typically been demonstrated. However, most of these compounds, when present as adjuvants, are unsuitable because of their side-effects on the immune system (which occur in parallel with the required immunogenic properties). For example, many of these compounds are categorised as allergenic and in some circumstances bring about an over-reaction of the immune system which far exceeds the desired degree. These compounds are therefore likewise unsuitable as adjuvants for immune stimulation for the mentioned reasons.

Accordingly, it is a first object of the present invention to provide immune-stimulating agents, which act as adjuvants, if administered in combination with other biologically active compounds, in particular if administered together with immune-modulating compounds, preferably in combination with compounds, which specifically stimulate the immune system, such as antigens.

However, (unspecific) immune-stimulating effects can also be produced by directly using nucleic acids to trigger an unspecific immune response (innate immune response). Bacterial CpG-DNA sequences not only serve for genetic information For example, DNA is known to play a central role in the production of unspecific immune responses. Bacterial DNA, for example, is known to act as "danger" signal to alert immune cells, such as macrophages and dendritic cells and to promote protective Th1 polarized T cell immune responses. An immune-stimulating action appears to result from the presence of unmethylated CG motifs, and such CpG-DNA has therefore been proposed as an immune-stimulating agent as such (see U.S. Pat. No. 5,663,153). CpG-DNA directly causes activation of members of the innate immune system yielding in up-regulation of co-stimulatory molecules and pro-inflammatory cytokines. This immune-stimulating property of DNA can also be achieved by DNA oligonucleotides which are stabilised by phosphorothioate modification (U.S. Pat. No. 6,239,116). Finally, U.S. Pat. No. 6,406,705 discloses immune-stimulating compositions which contain a synergistic combination of a CpG oligodeoxyribonucleotide and a non-nucleic acid compound to exert a stimulating effect on the innate immune system.

However, the use of DNA to exert an unspecific immune response can be less advantageous from several points of view. DNA is decomposed only relatively slowly in vivo, so that, when immune-stimulating (foreign) DNA is used, the formation of anti-DNA antibodies may occur, which has been confirmed in an animal model in the mouse (Gilkeson et al., J. Clin. Invest. 1995, 95: 1398-1402). Persistence of (foreign) DNA in the organism can thus lead to over-activation of the immune system, which is known to result in mice in splenomegaly (Montheith et al., Anticancer Drug Res. 1997, 12(5): 421-432). Furthermore, (foreign) DNA can interact with the host genome and cause mutations, in particular by integration into the host genome. For example, insertion of the introduced (foreign) DNA into an intact gene can occur, which represents a mutation which can impede or even eliminate completely the function of the endogenous gene. As a result of such integration events, on the one hand enzyme systems that are vital to the cell can be destroyed, and on the other hand there is also a risk that the cell so changed will be transformed into a degenerate state if, by the integration of the (foreign) DNA, a gene that is critical for the regulation of cell growth is changed. Therefore, in processes known hitherto, a possible risk of cancer formation cannot be ruled out when using (foreign) DNA as immune-stimulating agent.

It is therefore generally more advantageous to use specific RNA molecules as a compound to elicit an unspecific immune response by the innate immune system. RNA oligonucleotides are known to bind to TLR-7/-8 receptors thereby exerting an immuno-stimulating effect. RNA as immuno-stimulating agent typically has a substantially shorter half-life in vivo than DNA. Nevertheless, even the use of those specific RNA molecules known as immuno-stimulating agents in the art has limitations. For example, the specific RNA sequences disclosed hitherto in the art exhibit only limited cell permeability in vivo. This may require an increased amount of RNA for immune stimulation, which, regardless of the increased costs owing to the increased amounts of RNA to be administered, involves the risk of the mostly undesirable side-effects described generally hereinbefore, for example irritation and inflammation at the site of administration. Also, toxic side-effects cannot be ruled out when large amounts of the immune-stimulating agent are administered.

Despite the successes demonstrated hitherto, there is therefore a continued need for, and considerable interest in, improved immune stimulating agents which may exert by their own an immune response of the patient's innate immune system. Accordingly, it is a second object of the invention to provide immune-stimulating agents which exert an unspecific immune response by activating the patient's innate immune system.

Both objects of the present invention are solved by the provision of nucleic acid molecules of the following formulae (I) and (II). These inventive nucleic acid molecules activate the innate immune system, thus eliciting an unspecific immune response, and as adjuvants (e.g. as component of a vaccine) which support the immuno-stimulating activity of a second compound activtating the acquired immune system specifically.

The present invention provides a nucleic acid of formula (I):

$$G_l X_m G_n$$

wherein:
G is guanosine, uracil or an analogue of guanosine or uracil;
X is guanosine, uracil, adenosine, thymidine, cytosine or an analogue of the above-mentioned nucleotides;
l is an integer from 1 to 40,
wherein when l=1 G is guanosine or an analogue thereof,
when l>1 at least 50% of the nucleotides are guanosine or an analogue thereof;
m is an integer and is at least 3;
wherein when m=3 X is uracil or an analogue thereof,
when m>3 at least 3 successive uracils or analogues of uracil occur;
n is an integer from 1 to 40,
wherein when n=1 G is guanosine or an analogue thereof,
when n>1 at least 50% of the nucleotides are guanosine or an analogue thereof.

In addition, the present invention provides a nucleic acid of formula (II):

$$C_l X_m C_n$$

wherein
C is cytosine, uracil or an analogue of cytosine or uracil;
X is is guanosine, uracil, adenosine, thymidine, cytosine or an analogue of the above-mentioned nucleotides;
l is an integer from 1 to 40, wherein when l=1 C is cytosine or an analogue thereof,
when l>1 at least 50% of the nucleotides are cytosine or an analogue thereof;
m is an integer and is at least 3;
wherein when m=3 X is uracil or an analogue thereof,
when m>3 at least 3 successive uracils or analogues of uracil occur;
n is an integer from 1 to 40,
wherein when n=1 C is cytosine or an analogue thereof,
when n>1 at least 50% of the nucleotides are cytosine or an analogue thereof.

The nucleic acids of formula (I) or (II) according to the invention are typically relatively short nucleic acid molecules. The nucleic acid of either formula (I) or (II) according to the invention therefore typically has a length of approximately from 5 to 100 (but may also be longer than 100 nucleotides for specific embodiments, e.g. up to 200 nucleotides), from 5 to 90 or from 5 to 80 nucleotides, preferably a length of approximately from 5 to 70, more preferably a length of approximately from 8 to 60 and, more preferably a length of approximately from 15 to 60 nucleotides, more preferably from 20 to 60, most preferably from 30 to 60 nucleotides. If the nucleic acid of the invention has a maximum length of e.g. 100 nucleotides, m will typically be <=98.

The nucleic acid of either formula (I) or (II) according to the invention can be a RNA or DNA (for example a cDNA), it can be single-stranded or double-stranded, in the form of a homo- or hetero-duplex and be linear or circular. The nucleic acid of either formula (I) or (II) according to the invention is particularly preferably in the form of single-stranded RNA.

G in the nucleic acid of formula (I) according to the invention is guanosine or uracil or an analogue thereof. In this connection, guanosine or uracil nucleotide analogues are defined as non-natively occurring variants of naturally occurring nucleotides. Accordingly, guanosine or uracil analogues are chemically derivatized nucleotides with non-natively occurring functional groups, which are preferably added to or deleted from the naturally occurring guanosine or uracil nucleotide or which substitute the naturally occurring functional groups of a guanosine or uracil nucleotide. Accordingly, each component of the naturally occurring guanosine or uracil nucleotide may be modified, namely the base component, the sugar (ribose) component and/or the phosphate component forming the oligonucleotide's backbone. The phosphate moieties may be substituted by e.g. phosphoramidates, phosphorothioates, peptide nucleotides, methylphosphonates etc.

Accordingly, analogues of guanosine or uracil include, without implying any limitation, any naturally occurring or non-naturally occurring guanosine or uracil that has been altered chemically, for example by acetylation, methylation, hydroxylation, etc., including, for example, 1-methyl-guanosine, 2-methyl-guanosine, 2,2-dimethyl-guanosine, 7-methyl-guanosine, dihydro-uracil, 4-thio-uracil, 5-carboxymethylaminomethyl-2-thio-uracil, 5-(carboxy-hydroxylmethyl)-uracil, 5-fluoro-uracil, 5-bromo-uracil, 5-carboxymethylaminomethyl-uracil, 5-methyl-2-thio-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v). The preparation of such analogues is known to a person skilled in the art, for example from U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference herein in their entirety. In the case of an analogue as described above, preference is given according to the invention especially to those analogues that increase the immunogenity of the nucleic acid of formula (I) according to the invention and/or do not interfere with a further modification that has been introduced. At least one analogue can occur in the flanking sequence $G_l$ and/or $G_n$, optionally at least 10%, 20%, 30%, 50%, 60%, 70%, 80% 90% of the nucleotides of the flanking sequences $G_l$ and/or $G_n$ exhibit properties of an analogue as defined herein, if the flanking sequence contains at least one analogue at all. Most preferably, all nucleotides of the flanking sequence are analogues, which may—most preferably—be identical analogues for the same type of nucleotides (e.g. all guanosine nucleotides are provided as 1-methyl-guanosine) or they may be distinct (e.g. at least two different guanosin analogues substitute the naturally occurring guanosin nucleotide). Preferably, 1 and n are from 1 to 20, more preferably from 1 to 10 and yet more preferably from 2 to 8.

The number of nucleotides G in the nucleic acid of formula (I) according to the invention is determined by 1 or n. 1 and n, independently of one another, are each an integer from 1 to 40, wherein when 1 or n=1 G is guanosine or an analogue thereof, and when 1 or n>1 at least 50% of the nucleotides are guanosine or an analogue thereof. For example, without implying any limitation, when 1 or n=4 $G_l$ or $G_n$ can be, for example, a GUGU, GGUU, UGUG, UUGG, GUUG, GGGU, GGUG, GUGG, UGGG or GGGG, etc.; when 1 or n=5 $G_l$ or $G_n$ can be, for example, a GGGUU, GGUGU, GUGGU, UGGGU, UGGUG, UGUGG, UUGGG, GUGUG, GGGGU, GGGUG, GGUGG, GUGGG, UGGGG, or GGGGG, etc.; etc. A nucleotide adjacent to $X_m$ in the nucleic acid of formula (I) according to the invention is preferably not a uracil.

C in the nucleic acid of formula (II) according to the invention is cytosine or uracil or an analogue thereof. In this connection, cytosine or uracil nucleotide analogues are defined as non-natively occurring variants of naturally occurring cytosine or uracil nucleotides. Accordingly, cytosine or uracil analogues are chemically derivatized nucleotides with non-natively occurring functional groups, which are preferably added to or deleted from the naturally occurring cytosine or uracil nucleotide or which substitute the naturally occurring functional groups of a cytosine or uracil nucleotide. Accordingly, each component of the naturally occurring cytosine or uracil nucleotide may be modified, namely the base component, the sugar (ribose) component and/or the phosphate component forming the oligonucleotide's backbone. The phosphate moieties may be substituted by e.g. phosphoramidates, phosphorothioates, peptide nucleotides, methylphosphonates etc.

Accordingly, analogues of cytosine or uracil include, without implying any limitation, any naturally occurring or non-naturally occurring cytosine or uracil that has been altered chemically, for example by acetylation, methylation, hydroxylation, etc., including, for example, 2-thio-cytosine, 3-methyl-cytosine, 4-acetyl-cytosine, dihydro-uracil, 4-thio-uracil, 5-carboxymethylaminomethyl-2-thio-uracil, 5-(carboxy-hydroxylmethyl)-uracil, 5-fluoro-uracil, 5-bromo-uracil, 5-carboxymethylaminomethyl-uracil, 5-methyl-2-thio-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v). The preparation of such analogues is known to a person skilled in the art, for example from U.S. Pat. Nos.

4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference herein in their entirety. In the case of an analogue as described above, preference is given according to the invention especially to those analogues that increase the immunogenity of the nucleic acid of formula (II) according to the invention and/or do not interfere with a further modification that has been introduced. At least one analogue can occur in the flanking sequence $C_1$ and/or $C_n$, optionally at least 10%, 20%, 30%, 50%, 60%, 70%, 80% 90% of the nucleotides of the flanking sequences $C_1$ and/or $C_n$ exhibit properties of an analogue as defined herein, if the flanking sequence contains at least one analogue at all. Most preferably, all nucleotides of the flanking sequence are analogues, which may—most preferably—be identical analogues for the same type of nucleotides (e.g. all cytosine nucleotides of the flanking sequence(s) are provided as 2-thio-cytosine) or they may be distinct (e.g. at least two different cytosine analogues substitute the naturally occurring cytosine nucleotides of the flanking sequence(s)). Preferably, 1 and n are from 1 to 20, more preferably from 1 to 10 and yet more preferably from 2 to 8.

Similarly, the number of nucleotides C in the nucleic acid of formula (II) according to the invention is determined by 1 or n. 1 and n, independently of one another, are each an integer from 1 to 40, wherein when 1 or n=1 C is cytosine or an analogue thereof, and when 1 or n>1 at least 50% of the nucleotides are cytosine or an analogue thereof. For example, without implying any limitation, when 1 or n=4 $C_1$ or $C_n$ can be, for example, a CUCU, CCUU, UCUC, UUCC, CUUC, CCCU, CCUC, CUCC, UCCC or CCCC, etc.; when 1 or n=5 $C_1$ or $C_n$ can be, for example, a CCCUU, CCUCU, CUCCU, UCCCU, UCCUC, UCUCC, UUCCC, CUCUC, CCCCU, CCCUC, CCUCC, CUCCC, UCCCC, or CCCCC, etc.; etc. A nucleotide adjacent to $X_m$ in the nucleic acid of formula (II) according to the invention is preferably not a uracil.

The term "identity" in the present application means that the sequences are compared in relation to a reference sequence and the percentage identity is determined by comparing them. For example, in order to determine the percentage identity of two nucleic acid sequences, the sequences can first be arranged relative to one another (alignment) in order to permit subsequent comparison of the sequences. To this end, for example, gaps can be introduced into the sequence of the first nucleic acid sequence and the nucleotides can be compared with the corresponding position of the second nucleic acid sequence. When a position in the first nucleic acid sequence is occupied with the same nucleotide as in a position in the second sequence, then the two sequences are identical at that position. The percentage identity between two sequences is a function of the number of identical positions divided by the sequences. If, for example, a specific sequence identity is assumed for a particular nucleic acid in comparison with a reference nucleic acid having a defined length, then this percentage identity is indicated relatively in relation to the reference nucleic acid. Therefore, starting, for example, from a nucleic acid that has 50% sequence identity with a reference nucleic acid having a length of 100 nucleotides, that nucleic acid can represent a nucleic acid having a length of 50 nucleotides that is wholly identical with a section of the reference nucleic acid having a length of 50 nucleotides. It can, however, also represent a nucleic acid having a length of 100 nucleotides that has 50% identity, that is to say in this case 50% identical nucleic acids, with the reference nucleic acid over its entire length. Alternatively, that nucleic acid can be a nucleic acid having a length of 200 nucleotides that, in a section of the nucleic acid having a length of 100 nucleotides, is wholly identical with the reference nucleic acid having a length of 100 nucleotides. Other nucleic acids naturally fulfil these criteria equally.

The determination of the percentage identity of two sequences can be carried out by means of a mathematical algorithm. A preferred but non-limiting example of a mathematical algorithm which can be used for comparing two sequences is the algorithm of Karlin et al. (1993), PNAS USA, 90:5873-5877. Such an algorithm is integrated into the NBLAST program, with which sequences having a desired identity with the sequences of the present invention can be identified. In order to obtain a gapped alignment as described above, the "Gapped BLAST" program can be used, as described in Altschul et al. (1997), Nucleic Acids Res, 25:3389-3402. When using BLAST and Gapped BLAST programs, the default parameters of the particular program (e.g. NBLAST) can be used. The sequences can further be aligned using version 9 of GAP (global alignment program) from "Genetic Computing Group", using the default (BLOSUM62) matrix (values −4 to +11) with a gap open penalty of −12 (for the first zero of a gap) and a gap extension penalty of −4 (for each additional successive zero in the gap). After the alignment, the percentage identity is calculated by expressing the number of correspondences as a percentage of the nucleic acids in the claimed sequence. The described methods for determining the percentage identity of two nucleic acid sequences can also be applied correspondingly to amino acid sequences using the appropriate programs.

Likewise preferably, for formula (I), when 1 or n>1, at least 60%, 70%, 80%, 90% or even 100% of the nucleotides are guanosine or an analogue thereof, as defined above. The remaining nucleotides to 100% (when guanosine constitutes less than 100% of the nucleotides) in the flanking sequences $G_l$ and/or $G_n$ are uracil or an analogue thereof, as defined hereinbefore. Also preferably, 1 and n, independently of one another, are each an integer from 2 to 30, more preferably an integer from 2 to 20 and yet more preferably an integer from 2 to 15. The lower limit of 1 or n can be varied if necessary and is at least 1, preferably at least 2, more preferably at least 3, 4, 5, 6, 7, 8, 9 or 10. This definition applies correspondingly to formula (II).

X in the nucleic acid of either formula (I) or formula (II) according to the invention is guanosine, uracil, adenosine, thymidine, cytosine or an analogue thereof. In this connection, nucleotide analogues are defined as non-natively occurring variants of naturally occurring nucleotides. Accordingly, analogues are chemically derivatized nucleotides with non-natively occurring functional groups, which are preferably added to or deleted from the naturally occurring nucleotide or which substitute the naturally occurring functional groups of a nucleotide. Accordingly, each component of the naturally occurring nucleotide may be modified, namely the base component, the sugar (ribose) component and/or the phosphate component forming the oligonucleotide's backbone. The phosphate moieties may be substituted by e.g. phosphoramidates, phosphorothioates, peptide nucleotides, methylphosphonates etc. Preferably, at least 10%, more preferably at least 20%, more preferably at least 30%, more preferably at least 50%, more preferably at least 70% and even more preferably at least 90% of all "X" nucleotides exhibit properties of an analogue as defined herein, if the inventive nucleic acid contains at least one analogue at all. The analogues substituting a specific nucleotide type within the core sequence formed by "Xm" may be identical, e.g. all cytosine nucleotides occurring in the core sequences are formed by 2-thio-cytosine, or they may be distinct for a specific nucleotide, e.g. at least two distinct cytosine analogues are contained within the core sequence.

Analogues of guanosine, uracil, adenosine, thymidine, cytosine include, without implying any limitation, any naturally occurring or non-naturally occurring guanosine, uracil, adenosine, thymidine or cytosine that has been altered chemically, for example by acetylation, methylation, hydroxylation, etc., including 1-methyl-adenosine, 2-methyl-adenosine, 2-methylthio-N-6-isopentenyl-adenosine, N6-methyl-adenosine, N6-isopentenyl-adenosine, 2-thio-cytosine, 3-methyl-cytosine, 4-acetyl-cytosine, 2,6-diaminopurine, 1-methyl-guanosine, 2-methyl-guanosine, 2,2-dimethyl-guanosine, 7-methyl-guanosine, inosine, 1-methyl-inosine, dihydro-uracil, 4-thio-uracil, 5-carboxymethylaminomethyl-2-thio-uracil, 5-(carboxyhydroxylmethyl)-uracil, 5-fluoro-uracil, 5-bromo-uracil, 5-carboxymethylaminomethyl-uracil, 5-methyl-2-thio-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), queosine, β-D-mannosyl-queosine, wybutoxosine, and inosine. The preparation of such analogues is known to a person skilled in the art, for example from U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642. In the case of an analogue as described above, particular preference is given according to the invention to those analogues that increase the immunogenity of the nucleic acid of either formula (I) or formula (II) according to the invention and/or do not interfere with a further modification that has been introduced.

The number of X in the nucleic acid of either formula (I) or formula (II) according to the invention is determined by m. m is an integer and is typically at least 3, 4, 5, 6, 7, 8, 9 or 10, wherein when m=3 X is uracil or an analogue thereof, and when m>3 at least 3 directly successive uracils or an analogue thereof occur. Such a sequence of at least 3 directly successive uracils is referred to in connection with this application as a "monotonic uracil sequence". A monotonic uracil sequence typically has a length of at least 3, 4, 5, 6, 7, 8, 9 or 10, 10-15, 15-20, 20-25, 25-30, 30-50 or 50-90 uracils or optionally analogues of uracil as defined above. Such a monotonic uracil sequence occurs at least once in the nucleic acid of either formula (I) or formula (II) according to the invention. It is therefore possible, for example, for 1, 2, 3, 4, 5 or more monotonic uracil sequences having at least 3 uracils or analogues thereof to occur, which monotonic uracil sequences can be interrupted by at least one guanosine, adenosine, thymidine, cytosine or an analogue thereof, preferably 2, 3, 4, 5 or more. For example, when m=3 $X_m$ is a UUU. When m=4 $X_m$ can be, for example, without implying any limitation, a UUUA, UUUG, UUUC, UUUU, AUUU, GUUU or CUUU, etc. When n=10 $X_m$ can be, for example, without implying any limitation, a UUUAAUUUUC (SEQ ID NO: 89), UUUUGUUUUA (SEQ ID NO: 90), UUUGUUUGUU (SEQ ID NO: 91), UUGUUUUGUU (SEQ ID NO: 92), (SEQ ID NO: 93), etc. The nucleotides adjacent to $G_l$ or $G_n$ of the nucleic acid of formula (I) according to the invention preferably comprise uracil or analogues thereof. Similarly, the nucleotides adjacent to $C_l$ or $C_n$ of the nucleic acid of formula (II) according to the invention preferably comprise uracil or analogues thereof.

When m>3, typically at least 50%, preferably at least 60%, 70%, 80%, 90% or even 100%, of the nucleotides are uracil or an analogue thereof, as defined above. The remaining nucleotides to 100% (where there is less than 100% uracil in the sequence $X_m$) are then guanosine, uracil, adenosine, thymidine, cytosine or an analogue thereof, as defined above. Likewise preferably, m is an integer and is at least 4, 5, 6, 7, 8, 9 or 10, 10-15, 15-20, 20-25, 25-30, 30-50 or 50-90.

The nucleic acid of formula (I) according to the invention particularly preferably contains at least one of the following sequences of SEQ ID NOs: 1-80:

```
                                              (SEQ ID NO: 1)
GGUUUUUUUUUUUUUUUGGG;

(SEQ ID NO: 2)
GGGGGUUUUUUUUUGGGGG;

(SEQ ID NO: 3)
GGGGGUUUUUUUUUUUUUUUUUUUUUUUUUUGGGGG;

(SEQ ID NO: 4)
GUGUGUGUGUGUUUUUUUUUUUUUUGUGUGUGUGU;

(SEQ ID NO: 5)
GGUUGGUUGGUUUUUUUUUUUUUUUUGGUUGGUUGGUU;

(SEQ ID NO: 6)
GGGGGGGGGUUUGGGGGGG;

(SEQ ID NO: 7)
GGGGGGGGUUUUGGGGGGG;

(SEQ ID NO: 8)
GGGGGGGUUUUUGGGGGGG;

(SEQ ID NO: 9)
GGGGGGGUUUUUUGGGGGG;

(SEQ ID NO: 10)
GGGGGGUUUUUUUGGGGGG;

(SEQ ID NO: 11)
GGGGGGUUUUUUUUGGGGG;

(SEQ ID NO: 12)
GGGGGGUUUUUUUUUGGGG;

(SEQ ID NO: 13)
GGGGGUUUUUUUUUUGGGG;

(SEQ ID NO: 14)
GGGGGUUUUUUUUUUUGGG;

(SEQ ID NO: 15)
GGGGUUUUUUUUUUUUGGG;

(SEQ ID NO: 16)
GGGUUUUUUUUUUUUUUGG;

(SEQ ID NO: 17)
GGUUUUUUUUUUUUUUUGG;

(SEQ ID NO: 18)
GUUUUUUUUUUUUUUUUUG;

(SEQ ID NO: 19)
GGGGGGGGGUUUGGGGGGGG;

(SEQ ID NO: 20)
GGGGGGGGGUUUUGGGGGGGG;

(SEQ ID NO: 21)
GGGGGGGGUUUUUGGGGGGGG;

(SEQ ID NO: 22)
GGGGGGGGUUUUUUGGGGGGG;
```

```
                                                    (SEQ ID NO: 23)
GGGGGGGUUUUUUUGGGGGGG;

(SEQ ID NO: 24)
GGGGGGGUUUUUUUUGGGGGG;

(SEQ ID NO: 25)
GGGGGGUUUUUUUUUGGGGGG;

(SEQ ID NO: 26)
GGGGGGUUUUUUUUUUGGGGG;

(SEQ ID NO: 27)
GGGGGGUUUUUUUUUUUGGGG;

(SEQ ID NO: 28)
GGGGGUUUUUUUUUUUUGGGG;

(SEQ ID NO: 29)
GGGGGUUUUUUUUUUUUUGGG;

(SEQ ID NO: 30)
GGGUUUUUUUUUUUUUUUGGG;

(SEQ ID NO: 31)
GUUUUUUUUUUUUUUUUUUGG;

(SEQ ID NO: 32)
GGGGGGGGGGUUUGGGGGGGGG;

(SEQ ID NO: 33)
GGGGGGGGGGUUUUGGGGGGGG;

(SEQ ID NO: 34)
GGGGGGGGGUUUUUGGGGGGGG;

(SEQ ID NO: 35)
GGGGGGGGGUUUUUUGGGGGGG;

(SEQ ID NO: 36)
GGGGGGGGUUUUUUUGGGGGGG;

(SEQ ID NO: 37)
GGGGGGGGUUUUUUUUGGGGGG;

(SEQ ID NO: 38)
GGGGGGGGUUUUUUUUUGGGGG;

(SEQ ID NO: 39)
GGGGGGGUUUUUUUUUUGGGGG;

(SEQ ID NO: 40)
GGGGGGGUUUUUUUUUUUGGGG;

(SEQ ID NO: 41)
GGGGGGUUUUUUUUUUUUGGGG;

(SEQ ID NO: 42)
GGGGGGUUUUUUUUUUUUUGGG;

(SEQ ID NO: 43)
GGGGUUUUUUUUUUUUUUUGGG;

(SEQ ID NO: 44)
GGGUUUUUUUUUUUUUUUUUGG;

(SEQ ID NO: 45)
GUUUUUUUUUUUUUUUUUUUUG;

(SEQ ID NO: 46)
GGUUUUUUUUUUUUUUUUUUUUGG;

(SEQ ID NO: 47)
GGGUUUUUUUUUUUUUUUUUUUUGGG;

(SEQ ID NO: 48)
GGGGUUUUUUUUUUUUUUUUUUUUGGG;

(SEQ ID NO: 49)
GGGGGUUUUUUUUUUUUUUUUUUUUUGGGG;

(SEQ ID NO: 50)
GGGGGGUUUUUUUUUUUUUUUUUUUUUUGGGG;

(SEQ ID NO: 51)
GGGGGGGUUUUUUUUUUUUUUUUUUUUUUUGGGGG;

(SEQ ID NO: 52)
GGGGGGGGUUUUUUUUUUUUUUUUUUUUUUUUGGGGGG;

(SEQ ID NO: 53)
GGGGGGGGGUUUUUUUUUUUUUUUUUUUUUUUUUGGGGGGG;

(SEQ ID NO: 54)
GGUUUGG;

(SEQ ID NO: 55)
GGUUUUGG;

(SEQ ID NO: 56)
GGUUUUUGG;

(SEQ ID NO: 57)
GGUUUUUUGG;

(SEQ ID NO: 58)
GGUUUUUUUGG;

(SEQ ID NO: 59)
GGUUUUUUUUGG;

(SEQ ID NO: 60)
GGUUUUUUUUUGG;

(SEQ ID NO: 61)
GGUUUUUUUUUUGG;

(SEQ ID NO: 62)
GGUUUUUUUUUUUGG;

(SEQ ID NO: 63)
GGUUUUUUUUUUUUGG;

(SEQ ID NO: 64)
GGUUUUUUUUUUUUUGG;

(SEQ ID NO: 65)
GGUUUUUUUUUUUUUUGG;

(SEQ ID NO: 66)
GGUUUUUUUUUUUUUUUGG;

(SEQ ID NO: 67)
GGGUUUGGG;

(SEQ ID NO: 68)
GGGUUUUGGG;

(SEQ ID NO: 69)
GGGUUUUUGGG;

(SEQ ID NO: 70)
GGGUUUUUUGGG;

(SEQ ID NO: 71)
GGGUUUUUUUGGG;

(SEQ ID NO: 72)
GGGUUUUUUUUGGG;

(SEQ ID NO: 73)
GGGUUUUUUUUUGGG;

(SEQ ID NO: 74)
GGGUUUUUUUUUUGGG;

(SEQ ID NO: 75)
GGGUUUUUUUUUUUGGG;

(SEQ ID NO: 76)
GGGUUUUUUUUUUUUGGG;
```

-continued (SEQ ID NO: 77)
GGGUUUUUUUUUUUUGGG;

SEQ ID NO: 78
GGGUUUUUUUUUUUUUUGGGUUUUUUUUUUUUUUGGGUUUUUUUUUU
UUUUGGG;

SEQ ID NO: 79
GGGUUUUUUUUUUUUUUGGGGGUUUUUUUUUUUUUUGGG;

SEQ ID NO: 80
GGGUUUGGGUUUGGGUUUGGGUUUGGGUUUGGGUUUGGGUUUGGGUUUGG
G;

The nucleic acid of formula (II) according to the invention particularly preferably contains at least one of the following sequences of SEQ ID NOs: 81-83:

SEQ ID NO: 81
CCCUUUUUUUUUUUUUUCCCUUUUUUUUUUUUUUUCCCUUUUUUUUUU
UUUUCCC

SEQ ID NO: 82
CCCUUUCCCUUUCCCUUUCCCUUUCCCUUUCCCUUUCCCUUUCCCUUUCC
C

SEQ ID NO: 83
CCCUUUUUUUUUUUUUUCCCCCUUUUUUUUUUUUUUCCC

Nucleic acid sequences of either formula (I) or formula (II) according to the invention are preferably not naturally or synthetically prepared sequences of viral or bacterial origin.

The nucleic acid of either formula (I) or formula (II) according to the invention is typically provided as a "stabilised oligonucleotide", that is to say as an oligoribonucleotide or oligodeoxyribonucleotide that is resistant to in vivo degradation (e.g. by an exo- or endo-nuclease). Such stabilisation can be effected, for example, by a modified phosphate backbone of the nucleic acid of either formula (I) or formula (II) according to the invention. Nucleotides that are preferably used in this connection contain a phosphorothioate-modified phosphate backbone, preferably at least one of the phosphate oxygens contained in the phosphate backbone being replaced by a sulfur atom. Other stabilised oligonucleotides include, for example: non-ionic analogues, such as, for example, alkyl and aryl phosphonates, in which the charged phosphonate oxygen is replaced by an alkyl or aryl group, or phosphodiesters and alkylphosphotriesters, in which the charged oxygen residue is present in alkylated form.

The nucleic acid of either formula (I) or formula (II) according to the invention can likewise be stabilised. As mentioned above, any nucleic acid, for example DNA or RNA, can in principle be used for the nucleic acid of either formula (I) or formula (II) according to the invention. From the point of view of safety, however, the use of RNA for such a nucleic acid is preferred. In particular, RNA does not involve the risk of being stably integrated into the genome of the transfected cell. In addition, RNA is degraded substantially more easily in vivo. Likewise, no anti-RNA antibodies have hitherto been detected, presumably owing to the relatively short half-life of RNA in vivo as compared with DNA. In comparison with DNA, RNA is considerably less stable in solution, however, which is due substantially to RNA-degrading enzymes, so-called RNases (ribonucleases). Even the smallest ribonuclease contaminations are sufficient to degrade RNA completely in solution. Such RNase contaminations can generally be removed only by special treatment, in particular with diethyl pyrocarbonate (DEPC). Accordingly, the natural degradation of mRNA in the cytoplasm of cells is very finely regulated. A number of mechanisms are known in this connection in the prior art. Thus, the terminal structure is typically of critical importance for a mRNA in vivo. At the 5' end of naturally occurring mRNAs there is usually a so-called "cap structure" (a modified guanosine nucleotide) and at the 3' end a sequence of up to 200 adenosine nucleotides (the so-called poly-A tail).

The nucleic acid of either formula (I) or formula (II) according to the invention, particularly if provided as an RNA, can therefore be stabilised against degradation by RNases by the addition of a so-called "5' cap" structure. Particular preference is given in this connection to a m7G(5')ppp (5'(A,G(5')ppp(5')A or G(5')ppp(5')G as the 5' cap" structure. However, such a modification is introduced only if a modification, for example a lipid modification, has not already been introduced at the 5' end of the nucleic acid of either formula (I) or formula (II) according to the invention or if the modification does not interfere with the immunogenic properties of the (unmodified or chemically modified) nucleic acid of either formula (I) or formula (II) according to the invention.

Alternatively, the 3' end of the nucleic acid of either formula (I) or formula (II) according to the invention, particularly if provided as an RNA, can be modified by a sequence of at least 50 adenosine ribonucleotides, preferably at least 70 adenosine ribonucleotides, more preferably at least 100 adenosine ribonucleotides, particularly preferably at least 200 adenosine ribonucleotides (so-called "poly-A tail"). Analogously, in this case too, such a modification can be introduced only if no modification, for example a lipid modification, has already been introduced at the 3' end of the nucleic acid of either formula (I) or formula (II) according to the invention or if the modification does not interfere with the immunogenic properties of the (unmodified or chemically modified) nucleic acid of either formula (I) or formula (II) according to the invention. Both above-mentioned modifications, that is to say the insertion of a "5' cap" structure or the insertion of a "poly-A tail" at the 3' end, prevent premature degradation of the nucleic acid of either formula (I) or formula (II) according to the invention in vivo and accordingly stabilise the nucleic acid of either formula (I) or formula (II) according to the invention in vivo.

According to a particular embodiment, the nucleic acid of either formula (I), $G_lX_mG_n$, or of formula (II), $C_lX_mC_n$, according to the invention can contain a lipid modification. Such a lipid-modified nucleic acid according to the invention typically comprises a nucleic acid of either formula (I) or formula (II) according to the invention as defined above, at least one linker covalently linked with that nucleic acid according to the invention, and at least one lipid covalently linked with the respective linker. Alternatively, the lipid-modified nucleic acid according to the invention comprises a (at least one) nucleic acid of either formula (I) or formula (II) according to the invention as described above and at least one (bifunctional) lipid covalently linked (without a linker) with that nucleic acid according to the invention. According to a third alternative, the lipid-modified nucleic acid according to the invention comprises a nucleic acid of either formula (I) or formula (II) according to the invention as defined above, at least one linker covalently linked with that nucleic acid according to the invention, and at least one lipid covalently linked with the respective linker, and also at least one (bifunctional) lipid covalently linked (without a linker) with that nucleic acid according to the invention The lipid contained in the lipid-modified nucleic acid according to the invention is typically a lipid or a lipophilic residue that preferably is itself biologically active. Such lipids preferably include natural substances or compounds such as, for example, vitamins, e.g. α-tocopherol (vitamin E), including RRR-α-tocopherol (formerly D-α-tocopherol), L-α-tocopherol, the racemate D,L-α-tocopherol, vitamin E succinate (VES), or vitamin A and its derivatives, e.g. retinoic acid, retinol, vitamin D and its derivatives, e.g. vitamin D and also the ergosterol precursors thereof, vitamin E and its derivatives, vitamin K and its derivatives, e.g. vitamin K and related quinone or phytol compounds, or steroids, such as bile acids, for example cholic acid, deoxycholic acid, dehydrocholic acid, cortisone, digoxygenin, testosterone, cholesterol or thiocholesterol. Further lipids or lipophilic residues within the scope of the present invention include, without implying any limitation, polyalkylene glycols (Oberhauser et al., Nucl. Acids Res., 1992, 20, 533), aliphatic groups such as, for example, $C_1$-$C_{20}$-alkanes, $C_1$-$C_{20}$-alkenes or $C_1$-$C_{20}$-alkanol compounds, etc., such as, for example, dodecanediol, hexadecanol or undecyl residues (Saison-Behmoaras et al., EMBO J, 1991, 10, 111; Kabanov et al., FEBS Lett., 1990, 259, 327; Svinarchuk et al., Biochimie, 1993, 75, 49), phospholipids such as, for example, phosphatidylglycerol, diacylphosphatidylglycerol, phosphatidylcholine, dipalmitoylphosphatidylcholine, distearoylphosphatidylcholine, phosphatidylserine, phosphatidylethanolamine, di-hexadecyl-rac-glycerol, sphingolipids, cerebrosides, gangliosides, or triethylammonium 1,2-di-O-hexadecyl-rac-glycero-3-H-phosphonate (Manoharan et al., Tetrahedron Lett., 1995, 36, 3651; Shea et al., Nucl. Acids Res., 1990, 18, 3777), polyamines or polyalkylene glycols, such as, for example, polyethylene glycol (PEG) (Manoharan et al., Nucleosides & Nucleotides, 1995, 14, 969), hexaethylene glycol (HEG), palmitin or palmityl residues (Mishra et al., Biochim. Biophys. Acta, 1995, 1264, 229), octadecylamines or hexylamino-carbonyl-oxycholesterol residues (Crooke et al., J. Pharmacol. Exp. Ther., 1996, 277, 923), and also waxes, terpenes, alicyclic hydrocarbons, saturated and mono- or poly-unsaturated fatty acid residues, etc.

Linking between the lipid and the nucleic acid of either formula (I) or formula (II) according to the invention can in principle take place at any nucleotide, at the base or the sugar component of any nucleotide of the inventive nucleic acid, at the 3' and/or 5' end, and/or at the phosphate backbone of the nucleic acid of either formula (I) or formula (II) according to the invention. Particular preference is given according to the invention to a terminal lipid modification of the nucleic acid according to the invention at the 3' and/or 5' end thereof. A terminal modification has a number of advantages over modifications within the sequence. On the one hand, modifications within the sequence can influence the hybridisation behaviour, which may have an adverse effect in the case of sterically demanding residues. On the other hand, in the case of the synthetic preparation of a lipid-modified nucleic acid according to the invention that is modified only terminally, the synthesis of the nucleic acid of either formula (I) or formula (II) according to the invention can be carried out with commercially available monomers that are obtainable in large quantities, and synthesis protocols known in the prior art can be used.

According to a first preferred embodiment, linking between the nucleic acid according to the invention and at least one lipid that is used is effected via a "linker" (covalently linked with the nucleic acid of either formula (I) or formula (II) according to the invention). Linkers within the scope of the present invention typically have at least two and optionally 3, 4, 5, 6, 7, 8, 9, 10, 10-20, 20-30 or more reactive groups, selected from, for example, a hydroxy group, an amino group, an alkoxy group, etc. One reactive group preferably serves to bind the above-described nucleic acid of either formula (I) or formula (II) according to the invention, for example a RNA oligonucleotide. This reactive group can be present in protected form, for example as a DMT group (dimethoxytrityl chloride), as a Fmoc group, as a MMT (monomethoxytrityl) group, as a TFA (trifluoroacetic acid) group, etc. Furthermore, sulfur groups can be protected by disulfides, for example alkylthiols such as, for example, 3-thiopropanol, or by activated components such as 2-thiopyridine. One or more further reactive groups serve according to the invention for the covalent binding of one or more lipids. According to the first embodiment, therefore, a nucleic acid of either formula (I) or formula (II) according to the invention can bind via the covalently bound linker preferably at least one lipid, for example 1, 2, 3, 4, 5, 5-10, 10-20, 20-30 or more lipid(s), particularly preferably at least 3-8 or more lipid(s) per nucleic acid of either formula (I) or formula (II) according to the invention. The bound lipids can thereby be bound separately from one another at different positions of the nucleic acid of either formula (I) or formula (II) according to the invention, or they can be present in the form of a complex at one or more positions of the nucleic acid of either formula (I) or formula (II) according to the invention. An additional reactive group of the linker can be used for direct or indirect (cleavable) binding to a carrier material, for example a solid phase. Preferred linkers according to the present invention are, for example, glycol, glycerol and glycerol derivatives, 2-aminobutyl-1,3-propanediol and 2-aminobutyl-1,3-propanediol derivatives/skeleton, pyrrolidine linkers or pyrrolidine-containing organic molecules (in particular for a modification at the 3' end), etc. Glycerol or glycerol derivatives ($C_3$ anchor) or a 2-aminobutyl-1,3-propanediol derivative/skeleton ($C_7$ anchor) are particularly preferably used according to the invention as linkers. A glycerol derivative ($C_3$ anchor) as linker is particularly preferred when the lipid modification can be introduced via an ether bond. If the lipid modification is to be introduced via an amide or a urethane bond, for example, a 2-aminobutyl-1,3-propanediol skeleton ($C_7$ anchor), for example, is preferred.

In this connection, the nature of the bond formed between the linker and the nucleic acid of either formula (I) or formula (II) according to the invention is preferably such that it is compatible with the conditions and chemicals of amidite chemistry, that is to say it is preferably neither acid-nor base-labile. Preference is given in particular to bonds that are readily obtainable synthetically and are not hydrolysed by the ammoniacal cleavage procedure of a nucleic acid synthesis process. Suitable bonds are in principle all correspondingly suitable bonds, preferably ester bonds, amide bonds, urethane and ether bonds. In addition to the good accessibility of the starting materials (few synthesis steps), particular preference is given to the ether bond owing to its relatively high biological stability towards enzymatic hydrolysis.

According to a second preferred embodiment, the (at least one) nucleic acid of either formula (I) or formula (II) according to the invention is linked directly with at least one (bifunctional) lipid as described above, that is to say without the use of a linker as described above. In this case, the (bifunctional) lipid used according to the invention preferably contains at least two reactive groups or optionally 3, 4, 5, 6, 7, 8, 9, 10 or more reactive groups, a first reactive group serving to bind the lipid directly or indirectly to a carrier material described herein and at least one further reactive group serving to bind a nucleic acid of either formula (I) or formula (II) according to the invention. According to the second embodiment, a nucleic acid of either formula (I) or formula (II) according to the invention can therefore preferably bind at least one lipid (directly without a linker), for example 1, 2, 3, 4, 5, 5-10, 10-20, 20-30 or more lipid(s), particularly preferably at least 3-8 or more lipid(s) per nucleic acid of either formula (I) or formula (II) according to the invention. The bound lipids can be bound separately from one another at different positions of the nucleic acid of either formula (I) or formula (II) according to the invention, or they can be present in the form of a complex at one or more positions of the nucleic acid of either formula (I) or formula (II) according to the invention. Alternatively, at least one nucleic acid of either formula (I) or formula (II) according to the invention, for example optionally 3, 4, 5, 6, 7, 8, 9, 10, 10-20, 20-30 or more nucleic acids of either formula (I) or formula (II) according to the invention, can be bound according to the second embodiment to a lipid as described above via its reactive groups. Lipids that can be used for this second embodiment particularly preferably include those (bifunctional) lipids that permit coupling (preferably at their termini or optionally intramolecularly), such as, for example, polyethylene glycol (PEG) and derivatives thereof, hexaethylene glycol (HEG) and derivatives thereof, alkanediols, aminoalkane, thioalkanols, etc. The nature of the bond between a (bifunctional) lipid and a nucleic acid of either formula (I) or formula (II) according to the invention, as described above, is preferably as described for the first preferred embodiment.

According to a third embodiment, linking between the nucleic acid of either formula (I) or formula (II) according to the invention and at least one lipid as described above can take place via both of the above-mentioned embodiments simultaneously. For example, the nucleic acid of either formula (I) or formula (II) according to the invention can be linked at one position of the nucleic acid with at least one lipid via a linker (analogously to the first embodiment) and at a different position of the nucleic acid of either formula (I) or formula (II) according to the invention directly with at least one lipid without the use of a linker (analogously to the second embodiment). For example, at the 3' end of a nucleic acid of either formula (I) or formula (II) according to the invention, at least one lipid as described above can be covalently linked with the nucleic acid via a linker, and at the 5' end of the nucleic acid according to the invention, a lipid as described above can be covalently linked with the nucleic acid without a linker. Alternatively, at the 5' end of a nucleic acid of either formula (I) or formula (II) according to the invention, at least one lipid as described above can be covalently linked with the nucleic acid of either formula (I) or formula (II) according to the invention via a linker, and at the 3' end of the nucleic acid of either formula (I) or formula (II) according to the invention, a lipid as described above can be covalently linked with the nucleic acid of either formula (I) or formula (II) according to the invention without a linker. Likewise, covalent linking can take place not only at the termini of the nucleic acid of either formula (I) or formula (II) according to the invention but also intramolecularly, as described above, for example at the 3' end and intramolecularly, at the 5' end and intramolecularly, at the 3' and 5' end and intramolecularly, only intramolecularly, etc.

The lipid-modified nucleic acid of either formula (I) or formula (II) according to the invention can preferably be obtained by various processes. The lipid modification can in principle—as defined above—be introduced at any position of the nucleic acid of either formula (I) or formula (II) according to the invention, for example at the 3' and/or 5' ends or at the phosphate backbone of the nucleic acid of either formula (I) or formula (II) according to the invention and/or at any base or at the sugar of any nucleotide of the nucleic acid of either formula (I) or formula (II) according to the invention. According to the invention, preference is given to terminal lipid modifications at the 3' and/or 5' ends of the nucleic acids of either formula (I) or formula (II) according to the invention. By means of such a terminal chemical modification it is possible according to the invention to obtain a large number of differently derivatised nucleic acids. Examples of variants included in the invention are shown in FIG. 4. The process for preparing such lipid-modified nucleic acids of either formula (I) or formula (II) according to the invention is preferably chosen in dependence on the position of the lipid modification.

If, for example, the lipid modification takes place at the 3' end of the nucleic acid of either formula (I) or formula (II) according to the invention, then the lipid modification is typically carried out either before or after the preparation of the nucleic acid of either formula (I) or formula (II) according to the invention. The preparation of the nucleic acid of either formula (I) or formula (II) according to the invention can be carried out by direct synthesis of the nucleic acid or optionally by addition of a ready synthesised nucleic acid or a nucleic acid from samples isolated from other sources.

According to a first alternative, the nucleic acid of either formula (I) or formula (II) according to the invention is synthesised directly before introduction of the lipid, typically by means of processes known in the prior art for the synthesis of nucleic acids. To this end, a starting nucleoside is preferably bound to a solid phase, for example via a coupling molecule, e.g. a succinyl residue, and the nucleic acid of either formula (I) or formula (II) according to the invention is synthesised, for example by the process of amidite chemistry. A linker as described hereinbefore is then covalently bonded, preferably via a first reactive group of the linker, to the 3' end of the nucleic acid of either formula (I) or formula (II) according to the invention. A lipid as described hereinbefore can then be covalently linked with the linker via a second reactive group of the linker. Alternatively, the linker can be covalently linked with the lipid before it is bound to the 3' end of the nucleic acid of either formula (I) or formula (II) according to the invention. In this case, only the binding of a first reactive group of the linker with the 3' end of the nucleic acid of either formula (I) or formula (II) according to the invention is necessary. After synthesis of the nucleic acid of either formula (I) or formula (II) according to the invention, or after binding of the lipid, the nucleic acid of either formula (I) or formula (II) according to the invention can be separated from the solid phase and deprotected. If the synthesis has been carried out in solution, a washing and purification step for removing unreacted reactants as well as solvents and undesirable secondary products can be carried out after the synthesis of the lipid-modified nucleic acid according to the invention (and optionally before separation from the carrier material).

According to a further alternative, a 3'-lipid-modified nucleic acid of either formula (I) or formula (II) according to the invention, as defined above, is synthesised after introduction of the lipid on a reactive group of the linker or is bound to the reactive group of the linker as a ready synthesised nucleic acid of either formula (I) or formula (II) or a nucleic acid of either formula (I) or formula (II) that has been isolated from samples (see e.g. FIG. 5). To this end, for example, a first reactive group of a linker as described above can be reacted with a lipid as described hereinbefore. Then, preferably in a second step, a second reactive group of the linker is provided with an acid-stable protecting group, e.g. DMT, Fmoc, etc., in order to permit subsequent binding of the nucleic acid of either formula (I) or formula (II) according to the invention to that reactive group. The linker can then be bound directly or indirectly to a solid phase via a third reactive group of the linker. Indirect binding is possible, for example, via a (coupling) molecule, which can be bound both covalently to the linker and to the solid phase. Such a (coupling) molecule is, for example, a succinyl residue, etc., as described hereinbelow. Removal of the protecting group at the third reactive group of the linker and the binding or synthesis of the nucleic acid of either formula (I) or formula (II) according to the invention at the reactive group that is now accessible then usually take place. Finally, the lipid-modified nucleic acid according to the invention is typically cleaved from the carrier material (and the protective groups on the nucleic acid are optionally removed). However, a further lipid can optionally also be coupled to the 3' end of the coupled nucleic acid according to the invention, preferably according to one of the steps described hereinbefore.

According to a variant of this above-mentioned alternative, a linker as described above can be bound directly or indirectly to a solid phase via a first reactive group. An acid-stable protecting group is then first bound to a second reactive group of the linker. After binding of the protecting group to the second reactive group, a lipid as described above can first be bound to a third reactive group of the linker. Then there are likewise preferably carried out the removal of the protecting group at the third reactive group of the linker, the binding or synthesis of a nucleic acid of either formula (I) or formula (II) according to the invention at the reactive group that is now accessible, and the cleavage of the lipid-modified nucleic acid according to the invention from the carrier material (and optionally the removal of the protecting groups at the nucleic acid).

According to a particularly preferred embodiment of the 3'-lipid modification of a nucleic acid of either formula (I) or formula (II) according to the invention, as described above, such a lipid-modified nucleic acid according to the invention can be synthesised via a linker having three reactive groups (a trifunctional anchor comopund) based on a glycerol fundamental substance ($C_3$ anchor) and having a monofunctional lipid, such as, for example, a palmityl residue, cholesterol or tocopherol. As starting material for the synthesis of the linker there can be used, for example, alpha,beta-isopropylidene-glycerol (a glycerol containing a ketal protecting group), which is preferably first converted into the alcoholate with sodium hydride and is reacted with hexadecyl bromide and a lipid in a Williamson synthesis to form the corresponding ether. Alternatively, the ether bond can be linked in the first step by a different method, for example by formation of a tosylate of the α,β-isopropylidene-glycerol, and reaction of the tosylate with the reactive group of a lipid, for example an acidic proton, to form the corresponding ether. In a second stage, the ketal protecting group can be removed with an acid, for example acetic acid, dilute hydrochloric acid, etc., and then the primary hydroxy group of the diol can be protected selectively by dimethoxytrityl chloride (DMT-Cl). In the last stage, the reaction of the product obtained in the preceding step with succinic anhydride is preferably carried out to form the succinate with DMAP as catalyst. Such a linker is particularly suitable, for example, for the binding of palmityl residues or tocopherol as lipid (see e.g. FIG. 5).

According to another alternative, the 3'-lipid modification of a nucleic acid of either formula (I) or formula (II) according to the invention, as defined above, is effected using a (bifunctional) lipid, such as, for example, polyethylene glycol (PEG) or hexaethylene glycol (HEG), without using a linker as described above. Such bifunctional lipids typically have two functional groups as described above, wherein one end of the bifunctional lipid can preferably be bound to the carrier material via a (coupling) molecule, for example a base-labile succinyl anchor, etc., as described herein, and the nucleic acid of either formula (I) or formula (II) according to the invention can be synthesised at the other end of the bifunctional lipid (E. Bayer, M. Maier, K. Bleicher, H.-J. Gaus Z. *Naturforsch.* 50b (1995) 671). By the omission of the third functionalisation and of a linker, respectively, as used hereinbefore, the synthesis of such a lipid-modified nucleic acid according to the invention is simplified (see e.g. FIG. 6). For the preparation, the bifunctional lipid used according to the invention, for example polyethylene glycol, is typically first monosubstituted with a protecting group, for example DMT. In a second stage, esterification of the lipid protected at a reactive group is usually carried out with succinic anhydride, with DMAP catalysis, to form the succinate. Thereafter, in a third stage, the bifunctional lipid can be coupled to a carrier material and deprotected, following which the synthesis of the nucleic acid of either formula (I) or formula (II) according to the invention takes place in a fourth step in accordance with a process as described hereinbefore. Deprotection of the synthesised nucleic acid of either formula (I) or formula (II) according to the invention and cleavage of the lipid-modified nucleic acid from the carrier material are then optionally carried out.

According to another preferred embodiment, the lipid modification of a nucleic acid of either formula (I) or formula (II) according to the invention, as described above, takes place at the 5' end of the nucleic acid. The lipid modification is thereby typically carried out either after the provision or after the synthesis of the nucleic acid of either formula (I) or formula (II) according to the invention. The provision of the nucleic acid of either formula (I) or formula (II) according to the invention can be carried out—as defined above—via a direct synthesis of the nucleic acid of either formula (I) or formula (II) according to the invention or by addition of a ready synthesised nucleic acid of either formula (I) or formula (II) or a nucleic acid of either formula (I) or formula (II) isolated from samples. A synthesis of the nucleic acid of either formula (I) or formula (II) according to the invention takes place, preferably analogously to the method described above, according to processes of nucleic acid synthesis known in the prior art, more preferably according to the phosphoramidite process (see e.g. FIG. 7).

According to a particularly preferred embodiment, the lipid modification of a nucleic acid of either formula (I) or formula (II) according to the invention takes place at the 5' end of the nucleic acid according to the invention by specially modified phosphoramidites following a phosphoramidite process for the synthesis of the nucleic acid. Such amidites, which are obtainable relatively simply by synthesis, are conventionally coupled as the last monomer to a commercially available or to a ready synthesised nucleic acid. These reactions are distinguished by a relatively rapid reaction kinetics and very high coupling yields. The synthesis of the modified amidites preferably takes place by reaction of a phosphoramidite, for example beta-cyanoethyl-monochlorophosphoramidite (phosphorous acid mono-(2-cyanoethyl ester)-diisopropyl-amide chloride), with an alcohol, dissolved in a suitable solvent, for example in absolute dichloromethane, of a lipid as defined above, for example a lipid alcohol of tocopherol, cholesterol, hexadecanol, DMT-PEG, etc. Likewise preferably, DIPEA is added to the reaction solution as acid acceptor.

These phosphoramidites used for the synthesis of the 5'-lipid-modified nucleic acids according to the invention are relatively resistant to hydrolysis and can (prior to the synthesis) be purified chromatographically by means of silica gel. To this end, a small amount of a weak base, such as, for example, triethylamine, is typically added to the eluent in order to avoid decomposition of the amidite. It is important that this base is removed completely from the product again, in order to avoid poor coupling yields. This can be carried out, for example, by simple drying in vacuo, but preferably by purification of the phosphoramidites by precipitation thereof from tert-butyl methyl ether using pentane. If the lipid-modified amidites used have a very high viscosity, for example are present in the form of a viscous oil, (rapid) column chromatography can also be carried out, which makes it possible to dispense with triethylamine as base. Such a purification is typically not carried out in the case of PEG-modified amidites, however, because they contain the acid-labile DMT protecting group.

For the coupling reaction of the lipid-modified phosphoramidites to the 5' end of a nucleic acid of either formula (I) or formula (II) according to the invention there are preferably used those solvents in which the amidites used are sufficiently soluble. For example, owing to the high lipophilicity of the amidites used according to the invention, their solubility in acetonitrile can be limited. Apart from acetonitrile as the solvent that is typically used, a solution of chlorinated hydrocarbons is therefore preferably used for the coupling reactions, for example a 0.1 M solution in (absolute) dichloromethane. The use of dichloromethane requires some changes to the standard protocol of the synthesis cycle, however. For example, in order to avoid precipitation of the amidite in the pipes of the automatic synthesis device and on the carrier material, all the valves and pipes that come into contact with the amidite are flushed with (absolute) dichloromethane before and after the actual coupling step and blown dry.

When lipid-modified amidites are used, high coupling yields are typically obtained, which are comparable with the coupling yield of amidites conventionally used in the prior art. The kinetics of the reaction of lipid-modified amidites generally proceeds more slowly. For this reason, the coupling times are preferably (markedly) lengthened when lipid-modified amidites are used, as compared with standard protocols. Such coupling times can easily be determined by a person skilled in the art. Because a capping step after the coupling can be omitted, it is likewise possible, if required, to carry out a further synthesis cycle with the same lipid-modified amidite, in order to increase the overall yield of the reaction. In this case, the detritylation step is not usually carried out, for example in the case of DMT-modified lipids such as DMT-PEG.

In the synthesis of 5'-lipid-modified nucleic acids according to the invention, the phosphite triester via which the lipid is bound to the nucleic acid of either formula (I) or formula (II) according to the invention can be oxidised by a sulfurising agent. To this end there is preferably used a sulfurising agent that achieves oxidation of the phosphotriester as completely as possible. Otherwise, the sulfurisation reaction, for example for steric reasons, may proceed so incompletely that only a small amount of product, or no product at all, is obtained after the ammoniacal cleavage and deprotection of the MON. This phenomenon is dependent on the type of modification, the sulfurising agent used and the sulfurisation conditions. The oxidation is therefore carried out preferably with iodine. As a result, although a phosphodiester bond is introduced, it is not to be expected, owing to the proximity of the lipid residue, that this bond will be recognised as a substrate by nucleases.

In a lipid modification, linkers or (bifunctional) lipids contained in the nucleic acid of either formula (I) or formula (II) according to the invention, or optionally the nucleic acid of either formula (I) or formula (II) according to the invention itself, can, as described hereinbefore, be coupled directly or indirectly to a carrier material. Direct coupling is carried out preferably directly with the carrier material, while indirect coupling to the carrier material is typically carried out via a further (coupling) molecule. The bond formed by the coupling to a carrier material preferably exhibits a (cleavable) covalent bond with the linker or bifunctional lipid and/or a (cleavable) covalent bond with the solid phase. Compounds suitable as (coupling) molecule are, for example, dicarboxylic acids, for example succinyl residues (=succinyl anchors), oxalyl residues (=Oxalyl anchors), etc. Linkers, (bifunctional) lipids or optionally nucleic acids of either formula (I) or formula (II) according to the invention which, like, for example, aminoalkyl residues (e.g. aminopropyl or aminohexanyl residues), carry a free amino function, can be bound to the carrier material via a phthalimide linker. Thiol-containing linkers, (bifunctional) lipids or optionally nucleic acids of either formula (I) or formula (II) according to the invention can be bound in disulfide form to the carrier material. Suitable carrier materials in connection with this invention are in particular solid phases such as CPG, Tentagel®, amino-functionalised PS-PEG (Tentagel® S $NH_2$), etc., preferably Tentagel® or amino-functionalised PS-PEG (Tentagel® S $NH_2$). According to a particular embodiment it is possible for the coupling to a carrier material to couple, for example, the succinates of the described linkers or bifunctional lipids used according to the invention, preferably with TBTU/NMM (1H-benzotriazol-1-yl-1,1,3,3-tetramethyluronium tetrafluoroborate/N-methylmorpholine) as coupling reagent, to amino-functionalised PS-PEG (Tentagel® S $NH_2$). In the case of PS-PEG carrier materials on the 1 μmol scale that is conventionally used, the best results are typically obtained with loads of from 50 to 100 μmmol/g (E. Bayer, K. Bleicher, M. Maier Z. Naturforsch. 50b (1995) 1096). If, however, nucleotides are to be synthesised on a large scale according to the invention, the loading of the carrier materials is preferably as high as possible 100 μmol). According to the invention, such a process likewise results in good coupling yields (M. Gerster, M. Maier, N. Clausen, J. Schewitz, E. Bayer Z. Naturforsch. 52b (1997) 110). For example, carrier materials such as, for example, resins with a load of up to 138 μmmol/g or optionally more can be used with good synthesis yields. Because the coupling yields with the above-described linkers or bifunctional lipids are approximately 100%, the loading of the carrier material can be adjusted relatively precisely via the stoichiometry of these compounds. The loading is preferably monitored by spectroscopic quantification of the cleaved DMT protecting group (see experimental part). The residual amino functions still present on the carrier material can be capped with acetic anhydride. This capping is normally carried out following the loading of the carrier material but can also take place directly in the nucleic acid synthesis, for example in a DNA synthesiser. For the synthesis of lipid-modified nucleic acids on the derivatised PS-PEG carrier materials there are preferably used synthesis cycles developed specifically for Tentagel®, which take into account the characteristic properties of the material (E. Bayer, M. Maier, K. Bleicher, H.-J. Gaus Z. *Naturforsch.* 50b (1995) 671, E. Bayer, K. Bleicher, M. Maier Z. *Naturforsch.* 50b (1995) 1096.). Preferred changes as compared with the standard protocol include:

lengthened reaction times in the coupling, capping and oxidation steps;

increased number of detritylation steps;

lengthened washing steps after each step;

use of an ascorbic-acid-containing washing solution (0.1 M in dioxane/water=9:1) after the oxidation step that is usually necessary (for oxidation of the phosphite triester) during the amidite process, in order to remove traces of iodine.

It should be noted that the nature of the modification can have an influence on the individual steps of the synthesis cycle. For example, in the case of $PEG_{1500}$-derivatised carrier materials, a considerably slowed reaction kinetics is observed, which requires the detritylation steps to be lengthened again and the coupling time to be lengthened in addition. Such changes and adaptations are within the scope of the normal capability of a person skilled in the art and can be carried out at any time within the context of the present disclosure. With these reaction cycles so modified, both lipid-modified phosphorodiesters and phosphorothioates can be synthesised. The coupling yields of amidites on linkers or bifunctional lipids used according to the invention are not impaired by the lipid residues but correspond to conventional values (97-99%). The possibility of 5' derivatisation and the introduction of further modifications, for example at base, sugar or phosphate backbone, is retained when such 3' modifications are used.

The nucleic acid of either formula (I) or formula (II), as chemically unmodified nucleic acid or as (chemically) modified nucleic acid, e.g. as a lipid modified nucleic acid of either formula (I) or formula (II), can likewise be stabilised by forming a complex of the nucleic acid of either formula (I) or formula (II), e.g., without being limited thereto, with a cationic polymer, cationic peptides or polypeptides, preferably with a polycationic polymer such as polylysine or polyarginine or alternatively with cationic lipids or lipofectants, with a histone, a nucleoline, protamine, oligofectamine, spermine or spermidine, and cationic polysaccharides, in particular chitosan, TDM, MDP, muramyl dipeptide, pluronics, and/or one of the derivatives thereof, etc. Histones and protamines are cationic proteins which naturally compact DNA. They are thus responsible in vivo for the condensation of non-transcribed DNA and the DNA of certain viruses. As histones which may be used in the context of the present invention to form a complex with the nucleic acid of either formula (I) or formula (II), mention may be made more particularly of histones H1, H2a, H3 and H4. However, protamin (protamin P1 or P2) or cationic partial sequences of protamine are specifically preferred. In the context of the present invention, the compound may advantageously be represented by a peptide sequence derived from the protamin P1 or P2, and more precisely corresponding to the (cationic) sequence (SRSRYYRQRQRSRRRRRR (SEQ ID No. 85) or RRRLHRIHRRQHRSCRRRKRR (SEQ ID NO: 86). Other compounds suitable for forming a complex with the nucleic acid of either formula (I) or formula (II) according to the invention may be selected from the adjuvant compounds as defined herein, without being limited thereto.

In this context, "forming a complex" shall mean that the nucleic acid of either formula (I) or formula (II) is bound to a stabilizing compound as defined above, e.g. a cationic polymer, cationic peptides or polypeptides, etc. by forming a non-covalent complex between nucleic acid and stabilizing compound. Herein, "non-covalent" means that a reversible association of nucleic acid and stabilizing compound is formed by non-covalent interactions of these molecules, wherein the molecules are associated together by some type of interaction of electrons, other than a covalent bond, e.g. by van der Waals-bonds, i.e. a weak electrostatic attraction arising from a nonspecific attractive force of both molecules. Association of the nucleic acid of either formula (I) or formula (II) and the stabilizing compound is in equilibrium with dissociation of that complex. Without being bound to any theory, it is expected that the equilibrium is intracellularly shifted towards dissociated nucleic acid of either formula (I) or formula (II) and the stabilizing compound.

According to an embodiment, the nucleic acid of either formula (I) or formula (II) according to the invention can be an immune-stimulating agent, if administered without any other pharmaceutically active component, or may be used as an adjuvant, if administered together with a pharmaceutically active component, e.g. as a composition containing both the pharmaceutically active component and the adjuvant component (e.g. a vaccine composition containing a specific antigen and a nucleic acid according to formula (I) or (II) as an adjuvant).

A nucleic acid of either formula (I) or formula (II) according to the invention as an "immune-stimulating agent" is preferably capable of triggering a non-antigen-specific, immune reaction (as provided by the innate immune system), preferably in an immune-stimulating manner. An immune reaction can generally be brought about in various ways. An important factor for a suitable immune response is the stimulation of different T-cell sub-populations. T-lymphocytes typically differentiate into two sub-populations, the T-helper 1 (Th1) cells and the T-helper 2 (Th2) cells, with which the immune system is capable of destroying intracellular (Th1) and extracellular (Th2) pathogens (e.g. antigens).

The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of the B-cells for conversion into plasma cells and by formation of antibodies (e.g. against antigens). The Th1/Th2 ratio is therefore of great importance in the immune response. In connection with the present invention, the Th1/Th2 ratio of the immune response is preferably displaced by the immune-stimulating agent, namely the nucleic acid of either formula (I) or formula (II) according to the invention in the direction towards the cellular response, that is to say the Th1 response, and a predominantly cellular immune response is thereby induced. As defined above, the nucleic acid of the invention exerts by itself an unspecific immune response, which allows the nucleic acid to be used as such (without adding another pharmaceutically active component) as an immune-stimulating agent. If administered together with another pharmaceutically active component, preferably a specifically immune-stimulating component, the nucleic acid of the invention serves as an adjuvant supporting the specific immune response elicited by the other pharmaceutically active component.

The present invention relates also to pharmaceutical compositions containing a nucleic acid of either formula (I) or formula (II) according to the invention, or both, and optionally a pharmaceutically acceptable carrier and/or further auxiliary substances and additives and/or adjuvants (first embodiment of an inventive composition). Moreover, the present invention relates to pharmaceutical compositions containing a nucleic acid of either formula (I) or formula (II) according to the invention, or both, a pharmaceutically active component and optionally a pharmaceutically acceptable carrier and/or further auxiliary substances and additives and/or adjuvants (second embodiment of an inventive composition).

The pharmaceutical compositions according to the present invention typically comprise a safe and effective amount of a nucleic acid of either formula (I) or formula (II) according to the invention, or both, as described above. As used here, "safe and effective amount" means an amount of the nucleic acid of either formula (I) or formula (II) according to the invention, or both, that is sufficient to significantly induce a positive modification of a condition to be treated, for example of a tumour, autoimmune diseases, allergies or infectious disease. At the same time, however, a "safe and effective amount" is small enough to avoid serious side-effects, that is to say to permit a sensible relationship between advantage and risk. The determination of these limits typically lies within the scope of sensible medical judgment. In relation to the nucleic acid of either formula (I) or formula (II) according to the invention, the expression "safe and effective amount" preferably means an amount that is suitable for stimulating the immune system in such a manner that no excessive or damaging immune reactions are achieved but, preferably, also no such immune reactions below a measurable level. A "safe and effective amount" of the nucleic acid of either formula (I) or formula (II) according to the invention will vary in connection with the particular condition to be treated and also with the age and physical condition of the patient to be treated, the severity of the condition, the duration of the treatment, the nature of the accompanying therapy, of the particular pharmaceutically acceptable carrier used, and similar factors, within the knowledge and experience of the accompanying doctor. The pharmaceutical compositions according to the invention can be used according to the invention for human and also for veterinary medical purposes.

According to the first embodiment, the above-described nucleic acid of either formula (I) or formula (II) according to the invention can by itself be the immune-stimulating agent (without addition of any other pharmaceutically active components). This holds in particular, if the nucleic acid of either formula (I) or formula (II) according to the invention contains a lipid modification. The lipid may enhance the immune-stimulatory properties of the inventive nucleic acids or may well form a therapeutically active molecule, such as, for example, a vitamin, or steroid, as described above, for example α-tocopherol (vitamin E), D-alpha-tocopherol, L-alpha-tocopherol, D,L-alpha-tocopherol, vitamin E succinate (VES), vitamin A and its derivatives, vitamin D and its derivatives, vitamin K and its derivatives, etc.

The pharmaceutical composition according to the second embodiment of the invention contains (in addition to the nucleic acid of either formula (I) or formula (II) according to the invention) at least one additional pharmaceutically active component. A pharmaceutically active component in this connection is a compound that has a therapeutic effect against a particular indication, preferably cancer diseases, autoimmune disease, allergies or infectious diseases. Such compounds include, without implying any limitation, peptides, proteins, nucleic acids, (therapeutically active) low molecular weight organic or inorganic compounds (molecular weight less than 5000, preferably less than 1000), sugars, antigens or antibodies, therapeutic agents already known in the prior art, antigenic cells, antigenic cellular fragments, cellular fractions; modified, attenuated or de-activated (e.g. chemically or by irridation) pathogens (virus, bacteria etc.) etc.

According to a first alternative of the second embodiment (of a composition according to the invention), the pharmaceutically active component contained in the pharmaceutical composition is a immuno-modulatory component, preferably an immuno-stimulatory component. Most preferably, the pharmaceutically active component is an antigen or immunogen. An "antigen" and an "immunogen" are to be understood as being any structure that is able to bring about the formation of antibodies and/or the activation of a cellular immune response, that is to say a specific (and not an adjuvant) immune response. According to the invention, therefore, the terms "antigen" and "immunogen" are used synonymously. Examples of antigens are peptides, polypeptides, that is to say also proteins, cells, cell extracts, polysaccharides, polysaccharide conjugates, lipids, glycolipids and carbohydrates. There come into consideration as antigens, for example, tumour antigens, viral, bacterial, fungal and protozoological antigens. Preference is given to surface antigens of tumour cells and surface antigens, in particular secreted forms, of viral, bacterial, fungal or protozoological pathogens. The antigen can, of course, be present, for example in a vaccine according to the invention, also as a haptene coupled to a suitable carrier. Other antigenic components, e.g. deactivated or attenuated pathogens (as described above), may be used as well.

Antigenic (poly)peptides include all known antigenic peptides, for example tumour antigens, etc. Specific examples of tumour antigens are inter alfa tumour-specific surface antigens (TSSAs), for example 5T4, alpha5β1-integrin, 707-AP, AFP, ART-4, B7H4, BAGE, β-catenin/m, Bcr-abl, MN/C IX antigen, CA125, CAMEL, CAP-1, CASP-8, beta-catenin/m, CD4, CD19, CD20, CD22, CD25, CDC27/m, CD 30, CD33, CD52, CD56, CD80, CDK4/m, CEA, CT, Cyp-B, DAM, EGFR, ErbB3, ELF2M, EMMPRIN, EpCam, ETV6-AML1, G250, GAGE, GnT-V, Gp100, HAGE, HER-2/new, HLA-A*0201-R170I, HPV-E7, HSP70-2M, HAST-2, hTERT (or hTRT), iCE, IGF-1R, IL-2R, IL-5, KIAA0205, LAGE, LDLR/FUT, MAGE, MART-1/melan-A, MART-2/Ski, MC1R, myosin/m, MUC1, MUM-1, -2, -3, NA88-A, PAP, proteinase-3, p190 minor bcr-abl, Pml/RARα, PRAME, PSA, PSM, PSMA, RAGE, RU1 or RU2, SAGE, SART-1 or SART-3, survivin, TEL/AML1, TGFβ, TPI/m, TRP-1, TRP-2, TRP-2/INT2, VEGF and WT1, or from sequences such as, for example, NY-Eso-1 or NY-Eso-B. Any class of tumor antigens is suitable for the purpose of the present invention, e.g. tumor antigens known to be involved in neovascularization, influencing the extracellular matrix structure etc. The tumor antigens may be provided in the pharmaceutical composition as protein antigen or as mRNA or DNA encoding the tumor antigens, preferably the above tumor antigens.

By a second alternative of the second embodiment (for a composition according to the invention containing the inventive nucleic acid (as an adjuvant) and the additional pharmaceutically active component) the pharmaceutically active component is an antibody. In this connection, any therapeutically suitable antibody can be used. Particular preference is given according to the invention to an antibody directed against antigens, proteins or nucleic acids that play an important part in cancer diseases or infectious diseases, for example cell surface proteins, tumour suppressor genes or inhibitors thereof, growth and elongation factors, apoptosis-relevant proteins, tumour antigens, or antigens as described hereinbefore, etc.

According to a third alternative of the second embodiment, the pharmaceutically active component contained in the pharmaceutical composition according to the invention is a nucleic acid. Such a nucleic acid can be single-stranded or double-stranded and can be in the form of a homo- or hetero-duplex and also in linear or circular form. A nucleic acid contained as a pharmaceutically active component in the pharmaceutical composition is not limited in terms of its length and can include any naturally occurring nucleic acid sequence or its complement or a fragment thereof. Likewise, the nucleic acid used in this connection can be partially or wholly of synthetic nature. For example, the nucleic acid can include a nucleic acid that codes for a (therapeutically relevant) protein and/or that is capable of bringing about an immune reaction, for example an antigen or a nucleic acid coding for an antigen. An antigen here is preferably an antigen as described hereinbefore.

Preferably, the nucleic acid contained as a pharmaceutically active component in the pharmaceutical composition according to the invention is an mRNA. Such a mRNA can be added in its naked form to the pharmaceutical composition according to the invention or in a stabilised form that reduces or even prevents the degradation of the nucleic acid in vivo, for example by exo- and/or endo-nucleases.

For example, the mRNA contained as a pharmaceutically active component in the pharmaceutical composition according to the invention can be stabilised by an above-defined 5' cap and/or a poly-A tail at the 3' end of at least 50 nucleotides, preferably at least 70 nucleotides, more preferably at least 100 nucleotides, particularly preferably at least 200 nucleotides. As already mentioned, the terminal structure is of critical importance in vivo. The RNA is recognised as mRNA via these structures and the degradation is regulated. In addition, however, there are further processes that stabilise or destabilise RNA. Many of these processes are still unknown, but an interaction between the RNA and proteins often appears to be decisive therefor. For example, a "mRNA surveillance system" has recently been described (Hellerin and Parker, Ann. Rev. Genet. 1999, 33: 229 to 260), in which incomplete or non-sense mRNA is recognised by particular feedback protein interactions in the cytosol and is made amenable to degradation, a majority of these processes being carried out by exonucleases.

The stabilisation of the mRNA contained as a pharmaceutically active component in the pharmaceutical composition according to the invention can likewise by carried out by associating or complexing the mRNA with, or binding it to, a cationic compound, in particular a polycationic compound, for example a (poly)cationic peptide or protein. In particular the use of protamine, nucleoline, spermin or spermidine as the polycationic, nucleic-acid-binding protein is particularly effective. Furthermore, the use of other cationic peptides or proteins, such as poly-L-lysine or histones, is likewise possible. This procedure for stabilising mRNA is described in EP-A-1083232, the disclosure of which is incorporated by reference into the present invention in its entirety. Further preferred cationic substances which can be used for stabilising the mRNA present as a pharmaceutically active component include cationic polysaccharides, for example chitosan, polybrene, polyethyleneimine (PEI) or poly-L-lysine (PLL), etc. Apart from the action of the lipid-modified nucleic acid according to the invention in the form of an adjuvant in improving cell permeability, which is already advantageous, the association or complexing of the mRNA with cationic compounds, e.g. cationic proteins or cationic lipids, e.g. oligofectamine as a lipid based complexation reagent) preferably increases the transfer of the mRNA present as a pharmaceutically active component into the cells to be treated or into the organism to be treated. It is also referred to the disclosure herein with regard to the stabilizing effect for the nucleic acid of the invention by complexation, which holds for the stabilization of mRNA as well.

Another approach to stabilise mRNA as a pharmaceutically active component in the pharmaceutical composition according to the invention is the targeted changing of the sequence of the mRNA by removing or changing so-called destabilising sequence elements (DSEs). Signal proteins are able to bind to these destabilising sequence elements (DSEs), which occur in eukaryotic mRNA in particular, and regulate the enzymatic degradation of the mRNA in vivo. Therefore, in order further to stabilise the mRNA present as a pharmaceutically active component, one or more changes are preferably made as compared with the corresponding region of the wild-type mRNA, so that no destabilising sequence elements are present. Of course, it is likewise preferred according to the invention to eliminate DSEs optionally present in the untranslated regions (3'- and/or 5'-UTR) from the mRNA. Examples of the above DSEs are AU-rich sequences ("AURES"), which occur in 3'-UTR sections of numerous unstable mRNAs (Caput et al., Proc. Natl. Acad. Sci. USA 1986, 83: 1670 to 1674). The mRNA used as a pharmaceutically active component is therefore preferably modified as compared with the wild-type mRNA in such a manner that it does not contain any such destabilising sequences. This is also true of those sequence motifs that are recognised by possible endonucleases, for example the sequence GAACAAG, which is contained in the 3'-UTR segment of the gene coding for the transferrin receptor (Binder et al., EMBO J. 1994, 13: 1969 to 1980). Such sequence motifs are preferably also eliminated from the lipid-modified nucleic acid according to the invention.

The mRNA as a pharmaceutically active component in the pharmaceutical composition according to the invention can further be modified, for example for an efficient translation that may be desired, in such a manner that effective binding of the ribosomes to the ribosomal binding site (Kozak sequence: GCCGCCACCAUGG (SEQ ID NO: 84), the AUG forms the start codon) takes place. It has been noted in this connection that an increased A/U content around this position permits more efficient ribosome binding to the mRNA.

Furthermore, it is possible to introduce one or more so-called IRESs (internal ribosome entry side) into the mRNA used as a pharmaceutically active component. An IRES can thus function as the only ribosomal binding site, but it can also serve to provide a mRNA that codes for a plurality of peptides or polypeptides which are to be translated independently of one another by the ribosomes ("multicistronic mRNA"). Examples of IRES sequences which can be used according to the invention are those from picorna viruses (e.g. FMDV), plague viruses (CFFV), polio viruses (PV), encephalo-myocarditis viruses (ECMV), foot-and-mouth viruses (FMDV), hepatitis C viruses (HCV), conventional swine fever viruses (CSFV), murine leukoma virus (MLV), simean immune deficiency virus (SIV) or cricket paralysis viruses (CrPV).

The mRNA optionally used as a pharmaceutically active component in the pharmaceutical composition according to the invention can likewise contain in its 5'- and/or 3'-untranslated regions stabilising sequences that are capable of increasing the half-life of the mRNA in the cytosol. These stabilising sequences can exhibit 100% sequence homology with naturally occurring sequences that occur in viruses, bacteria and eukaryotes, but they can also be partially or wholly of synthetic nature. As examples of stabilising sequences which can be used in the present invention there may be mentioned the untranslated sequences (UTR) of the β-globin gene, for example of *Homo sapiens* or *Xenopus laevis*.

Another example of a stabilising sequence has the general formula (C/U)CCAN$_x$CCC(U/A)Py$_x$UC(C/U)CC (SEQ ID NO: 88), which is contained in the 3'-UTR of the very stable mRNA that codes for α-globin, α-(I)-collagen, 15-lipoxygenase or for tyrosine-hydroxylase (see Holcik et al., Proc. Natl. Acad. Sci. USA 1997, 94: 2410 to 2414). Of course, such stabilising sequences can be used individually or in combination with one another as well as in combination with other stabilising sequences known to a person skilled in the art.

In order to further increase an eventually desired translation, the mRNA used as a pharmaceutically active component can exhibit the following modifications as compared with a corresponding wild-type mRNA, which modifications can be present either as alternatives or in combination with one another. On the one hand, the G/C content of the region of the modified mRNA coding for a peptide or polypeptide can be greater than the G/C content of the coding region of the wild-type mRNA coding for the peptide or polypeptide, the amino acid sequence coded for being unmodified compared with the wild type. This modification is based on the fact that, for an efficient translation of a mRNA, the stability of the mRNA as such is critical. The composition and sequence of the various nucleotides plays a large part thereby. In particular, sequences having an increased G(guanosine)/C(cytosine) content are more stable than sequences having an increased A(adenosine)/U(uracil) content. According to the invention, therefore, while retaining the translated amino acid sequence, the codons are varied as compared with the wild-type mRNA in such a manner that they contain more G/C nucleotides. Because several codons code for the same amino acid (degeneracy of the genetic code), the codons that are advantageous for the stability can be determined (alternative codon usage). In dependence on the amino acid to be coded for by the mRNA, different possibilities for the modification of the mRNA sequence as compared to the wild-type sequence are possible. In the case of amino acids coded for by codons that contain solely G or C nucleotides, no modification of the codon is necessary. Accordingly, the codons for Pro (CCC or CCG), Arg (CGC or CGG), Ala (GCC or GCG) and Gly (GGC or GGG) do not require any change because no A or U is present. In the following cases, the codons that contain A and/or U nucleotides are changed by the substitution of different codons that code for the same amino acids but do not contain A and/or U. Examples are: the codons for Pro can be changed from CCU or CCA to CCC or CCG; the codons for Arg can be changed from CGU or CGA or AGA or AGG to CGC or CGG; the codons for Ala can be changed from GCU or GCA to GCC or GCG; the codons for Gly can be changed from GGU or GGA to GGC or GGG. In other cases, although A and U nucleotides cannot be eliminated from the codons, it is possible to reduce the A and U content by the use of codons that contain fewer A and/or U nucleotides. For example: the codons for Phe can be changed from UUU to UUC; the codons for Leu can be changed from UUA, CUU or CUA to CUC or CUG; the codons for Ser can be changed from UCU or UCA or AGU to UCC, UCG or AGC; the codon for Tyr can be changed from UAU to UAC; the stop codon UAA can be changed to UAG or UGA; the codon for Cys can be changed from UGU to UGC; the codon H is can be changed from CAU to CAC; the codon for Gln can be changed from CAA to CAG; the codons for Ile can be changed from AUU or AUA to AUC; the codons for Thr can be changed from ACU or ACA to ACC or ACG; the codon for Asn can be changed from AAU to AAC; the codon for Lys can be changed from AAA to AAG; the codons for Val can be changed from GUU or GUA to GUC or GUG; the codon for Asp can be changed from GAU to GAC; the codon for Glu can be changed from GAA to GAG. In the case of the codons for Met (AUG) and Trp (UGG), on the other hand, there is no possibility of sequence modification. The substitutions listed above can, of course, be used individually but also in all possible combinations for increasing the G/C content of the modified mRNA as compared with the original sequence. Thus, for example, all codons for Thr occurring in the original (wild-type) sequence can be changed to ACC (or ACG). Preferably, however, combinations of the above substitution possibilities are used, for example: substitution of all codons in the original sequence coding for Thr to ACC (or ACG) and substitution of all codons originally coding for Ser to UCC (or UCG or AGC);

substitution of all codons in the original sequence coding for Ile to AUC and substitution of all codons originally coding for Lys to AAG and substitution of all codons originally coding for Tyr to UAC; substitution of all codons in the original sequence coding for Val to GUC (or GUG) and substitution of all codons originally coding for Glu to GAG and substitution of all codons originally coding for Ala to GCC (or GCG) and substitution of all codons originally coding for Arg to CGC (or CGG); substitution of all codons in the original sequence coding for Val to GUC (or GUG) and substitution of all codons originally coding for Glu to GAG and substitution of all codons originally coding for Ala to GCC (or GCG) and substitution of all codons originally coding for Gly to GGC (or GGG) and substitution of all codons originally coding for Asn to AAC; substitution of all codons in the original sequence coding for Val to GUC (or GUG) and substitution of all codons originally coding for Phe to UUC and substitution of all codons originally coding for Cys to UGC and substitution of all codons originally coding for Leu to CUG (or CUC) and substitution of all codons originally coding for Gln to CAG and substitution of all codons originally coding for Pro to CCC (or CCG); etc. Preferably, the G/C content of the region (or of each other further section optionally present) of the mRNA that codes for the peptide or polypeptide is increased by at least 7% points, more preferably by at least 15% points, particularly preferably by at least 20% points, as compared with the G/C content of the coded region of the wild-type mRNA coding for the corresponding peptide or polypeptide and is preferably at least 50%, more preferably at least 70% and most preferably at least 90%. It is particularly preferred in this connection to increase the G/C content of the mRNA so modified in comparison with the wild-type sequence to the maximum possible degree.

A further preferred modification of a mRNA used as a pharmaceutically active component in the pharmaceutical composition is based on the finding that the translation efficiency is also determined by a different frequency in the occurrence of tRNAs in cells. If, therefore, so-called "rare"

codons are present in an increased number in a RNA sequence, then the corresponding mRNA is translated markedly more poorly than in the case where codons coding for relatively "frequent" tRNAs are present. According to the invention, therefore, the coding region in the mRNA used as a pharmaceutically active component is modified as compared with the corresponding region of the wild-type mRNA in such a manner that at least one codon of the wild-type sequence that codes for a relatively rare tRNA in the cell is replaced by a codon that codes for a relatively frequent tRNA in the cell, which carries the same amino acid as the relatively rare tRNA. By means of this modification, the RNA sequences are so modified that codons are introduced for which frequently occurring tRNAs are available. Which tRNAs occur relatively frequently in the cell and which, by contrast, are relatively rare is known to a person skilled in the art; see, for example, Akashi, Curr. Opin. Genet. Dev. 2001, 11(6): 660-666. By means of this modification it is possible according to the invention to replace all codons of the wild-type sequence that code for a relatively rare tRNA in the cell by a codon that codes for a relatively frequent tRNA in the cell, which carries the same amino acid as the relatively rare tRNA. It is particularly preferred to combine the increased, in particular maximum, sequential G/C content in the mRNA as described above with the "frequent" codons, without changing the amino acid sequence of an antigenic peptide or polypeptide (one or more) coded for by the coding region of the mRNA. Preferred antigens, which may be coded by the G/C enriched/optimized mRNA, are listed above.

According to a fourth alternative of the second embodiment (for the composition of the present invention), the nucleic acid contained as a pharmaceutically active component in the pharmaceutical composition according to the invention is a dsRNA, preferably siRNA. A dsRNA, or a siRNA, is of interest particularly in connection with the phenomenon of RNA interference. Attention was drawn to the phenomenon of RNA interference in the course of immunological research. In recent years, a RNA-based defence mechanism has been discovered, which occurs both in the kingdom of the fungi and in the plant and animal kingdom and acts as an "immune system of the genome". The system was originally described in various species independently of one another, first in C. elegans, before it was possible to identify the underlying mechanisms of the processes as being identical: RNA-mediated virus resistance in plants, PTGS (posttranscriptional gene silencing) in plants, and RNA interference in eukaryotes are accordingly based on a common procedure. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 bp (Elbashir et al. (2001) Nature 411: 494-498). Recently, dsRNA molecules have also been used in vivo (McCaffrey et al. (2002), Nature 418: 38-39; Xia et al. (2002), Nature Biotech. 20: 1006-1010; Brummelkamp et al. (2002), Cancer Cell 2: 243-247).

The double-stranded RNA (dsRNA) eventually used as a pharmaceutically active component in the pharmaceutical composition according to the invention therefore preferably contains a sequence having the general structure 5'-($N_{17-29}$)-3', wherein N is any base and represents nucleotides. The general structure is composed of a double-stranded RNA having a macromolecule composed of ribonucleotides, the ribonucleotide comprising a pentose (ribose), an organic base and a phosphate. The organic bases in the RNA here comprise the purine bases adenosine (A) and guanosine (G) and of the pyrimidine bases cytosine (C) and uracil (U). The dsRNA eventually used as a pharmaceutically active component in the pharmaceutical composition according to the invention contains such nucleotides or nucleotide analogues having an oriented structure. dsRNAs used as a pharmaceutically active component according to the invention preferably have the general structure 5'-($N_{21-23}$)-3', more preferably 5'-($N_{19-24}$)-3', yet more preferably 5'-($N_{21-23}$)-3', wherein N is any base. Preferably at least 90%, more preferably 95% and especially 100% of the nucleotides of a dsRNA used as a pharmaceutically active component will be complementary to a section of the (m)RNA sequence of a (therapeutically relevant) protein or antigen described (as a pharmaceutically active component) hereinbefore. 90% complementary means that with a length of a dsRNA used according to the invention of, for example, 20 nucleotides, this contains not more than 2 nucleotides without corresponding complementarity with the corresponding section of the (m)RNA. The sequence of the double-stranded RNA optionally used in the pharmaceutical composition according to the invention is, however, preferably wholly complementary in its general structure with a section of the (m)RNA of a protein or antigen described as a pharmaceutically active component hereinbefore.

In principle, all the sections having a length of from 17 to 29, preferably from 19 to 25, base pairs that occur in the coding region of the (m)RNA can serve as target sequence for a dsRNA eventually used as a pharmaceutically active component in the pharmaceutical composition according to the invention. Equally, dsRNAs used as a pharmaceutically active component can also be directed against nucleotide sequences of a (therapeutically relevant) protein or antigen described (as a pharmaceutically active component) hereinbefore that do not lie in the coding region, in particular in the 5' non-coding region of the (m)RNA, for example, therefore, against non-coding regions of the (m)RNA having a regulatory function. The target sequence of the dsRNA used as a pharmaceutically active component of a protein or antigen described hereinbefore can therefore lie in the translated and untranslated region of the (m)RNA and/or in the region of the control elements. The target sequence of a dsRNA used as a pharmaceutically active component in the pharmaceutical composition according to the invention can also lie in the overlapping region of untranslated and translated sequence; in particular, the target sequence can comprise at least one nucleotide upstream of the start triplet of the coding region of the (m)RNA.

A modified nucleotide can preferably occur in a dsRNA eventually used as a pharmaceutically active component in the pharmaceutical composition according to the invention. The expression "modified nucleotide" means according to the invention that the nucleotide in question has been chemically modified. The person skilled in the art understands by the expression "chemical modification" that the modified nucleotide has been changed in comparison with naturally occurring nucleotides by the replacement, addition or removal of one or more atoms or atom groups. At least one modified nucleotide in dsRNA used according to the invention serves on the one hand for stability and on the other hand to prevent dissociation. Preferably from 2 to 10 and more preferably from 2 to 5 nucleotides in a dsRNA used according to the invention have been modified. Advantageously, at least one 2'-hydroxy group of the nucleotides of the dsRNA in the double-stranded structure has been replaced by a chemical group, preferably a 2'-amino or a 2'-methyl group. At least one nucleotide in at least one strand of the double-stranded structure can also be a so-called "locked nucleotide" having a sugar ring that has been chemically modified, preferably by a 2'-O, 4'-C-methylene bridge. Several nucleotides of the dsRNA used according to the invention are advantageously locked nucleotides. Moreover, by modification of the backbone of a dsRNA used according to the invention, premature degradation thereof can be prevented. Particular preference is given in this connection to a dsRNA that has been modified in the form of phosphorothioate, 2'-O-methyl-RNA, LNA, LNA/DNA gapmers, etc. and therefore has a longer half-life in vivo. The ends of the double-stranded RNA (dsRNA) used as a pharmaceutically active component in the pharmaceutical composition according to the invention can preferably be modified in order to counteract degradation in the cell or dissociation into the individual strands, in particular in order to avoid premature degradation by nucleases. A normally undesirable dissociation of the individual strands of dsRNA occurs in particular when low concentrations thereof or short chain lengths are used. For the particularly effective inhibition of dissociation, the cohesion, effected by the nucleotide pairs, of the double-stranded structure of dsRNA used according to the invention can be increased by at least one, preferably more than one, chemical linkage(s). A dsRNA used as a pharmaceutically active component in the pharmaceutical composition according to the invention whose dissociation has been reduced has higher stability towards enzymatic and chemical degradation in the cell or in the organism (in vivo) or ex vivo and therefore has a longer half-life. A further possibility for preventing premature dissociation in the cell of dsRNA used according to the invention consists in forming hairpin loop(s) at each end of the strands. In a particular embodiment, a dsRNA used in the pharmaceutical composition according to the invention therefore has a hairpin structure in order to slow the dissociation kinetics. In such a structure, a loop structure is formed preferably at the 5' and/or 3' end. Such a loop structure has no hydrogen bridges, and typically therefore no complementarity, between nucleotide bases. Typically, such a loop has a length of at least 5, preferably at least 7 nucleotides and in that manner links the two complementary individual strands of a dsRNA used according to the invention. In order to prevent dissociation of the strands, the nucleotides of the two strands of the dsRNA used according to the invention can likewise preferably be so modified that strengthening of the hydrogen bridge bond is achieved, for example by increasing the hydrogen bridge bond capacity between the bases by optionally modified nucleotides. As a result, the stability of the interaction between the strands is increased and the dsRNA is protected against attack by RNases.

According to a particularly preferred embodiment, the dsRNA used as a pharmaceutically active component in the pharmaceutical composition according to the invention is directed against the (m)RNA of a protein or antigen as described hereinbefore. The dsRNA used preferably thereby suppresses the translation of an above-described protein or antigen in a cell to the extent of at least 50%, more preferably 60%, yet more preferably 70% and most preferably at least 90%, that is to say the cell contains preferably not more than half of the naturally occurring (without treatment with dsRNA used according to the invention) cellular concentration of an above-described protein or antigen. The suppression of the translation of these proteins or antigens in cells after addition of dsRNA molecules used according to the invention is based on the phenomenon of RNA interference caused by such molecules. The dsRNA used according to the invention is then a so-called siRNA, which triggers the phenomenon of RNA interference and can bind the (m)RNA of an above-described protein or antigen. Measurement or demonstration of the translation suppression triggered in cells by the dsRNA used according to the invention can be carried out by Northern blot, quantitative real-time PCR or, at protein level, with specific antibodies against an above-described protein or antigen. The dsRNA eventually used as a pharmaceutically active component in the pharmaceutical composition according to the invention, and a corresponding siRNA, can be prepared by processes known to the person skilled in the art.

The pharmaceutical composition (according to the first or the second embodiment) according to the invention typically contains a pharmaceutically acceptable carrier. The expression "pharmaceutically acceptable carrier" used here preferably includes the liquid or non-liquid basis of the composition. If the composition is provided in liquid form, the carrier will typically be pyrogen-free water; isotonic saline or buffered (aqueous) solutions, e.g phosphate, citrate etc. buffered solutions. Particularly for injection of the inventive pharmaceutical composition, a buffer, preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferrred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_2$) and optionally potassium chloride (KCl), wherein further anions may be present additional to the chlorides. Typically, the salts in the injection buffer are present in a concentration of at least 50 mM sodium chloride (NaCl), at least 3 mM potassium chloride (KCl) and at least 0.01 mM calcium chloride ($CaCl_2$).

The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. in "in vivo" methods occurring liquids such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may beused as well, which are suitable for administration to a person. The term "compatible" as used here means that the constituents of the pharmaceutical composition are capable of being mixed with the pharmaceutically active component, with the nucleic acid of the invention as immune-stimulating agent or as an adjuvant as such and with one another component in such a manner that no interaction occurs which would substantially reduce the pharmaceutical effectiveness of the composition under usual use conditions. Pharmaceutically acceptable carriers must, of course, have sufficiently high purity and sufficiently low toxicity to make them suitable for administration to a person to be treated. Some examples of compounds which can be used as pharmaceutically acceptable carriers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from *theobroma*; polyols, such as, for example, polypropylene glycol, glycerol, sorbitol, mannitol and polyethylene glycol; alginic acid.

The choice of a pharmaceutically acceptable carrier is determined in principle by the manner in which the pharmaceutical compositions according to the invention are administered. The pharmaceutical compositions according to the invention can be administered, for example, systemically. Routes for administration include, for example, transdermal, oral, parenteral, including subcutaneous or intravenous injections, topical and/or intranasal routes. The suitable amount of the pharmaceutical composition to be used can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the compound is to be administered perorally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

In order to further increase the immunogenicity, the pharmaceutical composition according to the invention can additionally contain one or more auxiliary substances. A synergistic action of the nucleic acid of either formula (I) or formula (II) according to the invention and of an auxiliary substance optionally additionally contained in the pharmaceutical composition (and, eventually, a pharmaceutically active component) as described above is preferably achieved thereby. Depending on the various types of auxiliary substances, various mechanisms can come into consideration in this respect. For example, compounds that permit the maturation of dendritic cells (DCs), for example lipopolysaccharides, TNF-α or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response produced by the immune-stimulating adjuvant according to the invention to be enhanced and/or influenced in a targeted manner. Particularly preferred auxiliary substances are cytokines, such as monokines, lymphokines, interleukins or chemokines, that promote the immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-α, IFN-β, INF-γ, GM-CSF, G-CSF, M-CSF, LT-β or TNF-α, growth factors, such as hGH.

Further additives which may be included in the compositions according to the invention are emulsifiers, such as, for example, Tween®; wetting agents, such as, for example, sodium lauryl sulfate; colouring agents; taste-imparting agents, pharmaceutical carriers; tablet-forming agents; stabilisers; antioxidants; preservatives.

The pharmaceutical composition according to the invention (first (without a pharmaceutically active component) and second (with a pharmaceutically active component) embodiment) can also additionally contain an adjuvant. Acoordingly, the nucleic acid of either formula (I) or formula (II) according to the invention as an immune-stimulating agent or as an adjuvant (for the second embodiment of the inventibve pharmaceutical composition), can be combined with further immune-stimulating agents/adjuvants. Within the scope of the present invention, suitable agents/adjuvants for these purposes are in particular those compounds that enhance (by one or more mechanisms) the biological property/properties of the (modified or unmodified) nucleic acid of either formula (I) or formula (II) according to the invention, that is to say in particular substances that potentiate the immune-stimulating action of the nucleic acid of either formula (I) or formula (II) according to the invention. Examples of agents/adjuvants which can be used according to the invention include, without implying any limitation, stabilising cationic peptides or polypeptides as described above, such as protamine, nucleoline, spermine or spermidine, and cationic polysaccharides, in particular chitosan, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyldodecanoyl-amide hydroacetate); CALCITRIOL™ (1α,25-dihydroxy-vitamin D3); calcium phosphate gel; CAPTM (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(b1-4)-N-acetylmuramyl-L-alanyl-D-isoglutamine); imiquimod (1-(2-methylpropyl)-1H-imidazo [4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-γ; interleukin-1β; interleukin-2; interleukin-7; interleukin-12; ISCOMS™ ("Immune Stimulating Complexes"); ISCOPREP 7.0.3.™; liposomes; LOXORIBINE™ (7-allyl-8-oxoguanosine); LT oral adjuvant (E. coli labile enterotoxin-protoxin); microspheres and microparticles of any composition; MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1, 2-dipalmitoyl-sn-glycero-3-(hydroxyphosphoryloxy))-ethylamide, monosodium salt); MURAMETIDE™ (Nac-Mur-L-Ala-D-Gln-OCH$_3$); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (β-glucan); PLGA, PGA and PLA (homo- and co-polymers of lactic acid and glycolic acid; micro-/nano-spheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5-c]-quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and the like, etc. Lipopeptides, such as Pam3Cys, are likewise particularly suitable for combining with the nucleic acid of either formula (I) or formula (II) according to the invention present in the form of an immune-stimulating adjuvant (see Deres et al., Nature 1989, 342: 561-564).

Adjuvants as mentioned above may be categorized into several classes, including adjuvants suitable for depot and delivery, for costimulation, adjuvants suitable as antagonists, etc. Preferred adjuvants suitable for depot and delivery may include e.g. aluminium salts such as Adju-phos, Alhydrogel, Rehydragel, etc., emulsions, such as CFA, SAF, IFA, MF59, Provax, TiterMax, Montanide, Vaxfectin, etc., copolymers, such as Optivax (CRL1005), L121, Poloaxmer4010), etc., liposomes, such as Stealth, etc., cochleates, such as BIORAL, etc., plant derived adjuvatns, such as QS21, Quil A, Iscomatrix, ISCOM, etc. Preferred adjuvants suitable for costimulation may include e.g. Tomatine, biopolymers, such as PLG, PMM, Inulin, etc., Microbe derived adjuvants, such as Romurtide, DETOX, MPL, CWS, Mannose, CpG7909, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP, etc. Preferred adjuvants suitable as antagonists may e.g. include CGRP neuropeptide, etc.

Any compound, which is known to be immune-stimulating due to its binding affinity (as ligands) to Toll-like receptors: TLR1, TLR2, TLR3, TLR4, TLR5, TLR6, TLR7, TLR8, TLR9, TLR10, TLR11, TLR12 or TLR13 may suitably be used as further component to further stimulate the immune response induced by nucleic acids of the invention in the inventive pharmaceutical compositions.

Another class of compounds, which may be added to a pharmaceutical composition of the invention are CpG nucleic acids, in particular CpG-RNA or CpG-DNA. A CpG-RNA or CpG-DNA can be a single-stranded CpG-DNA (ss CpG-DNA), a double-stranded CpG-DNA (ds-DNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

According to a particularly preferred embodiment, the pharmaceutical composition according to the invention can also be provided as a vaccine. Vaccines according to the invention typically comprise (correspond to) a pharmaceutical composition according to the invention. The composition of such vaccines according to the invention are characterized by a specific class of pharmaceutically active components incorporated into the vaccine composition. Typically, the pharmaceutically active compound will be an immunstimulatory substance, which evokes a specific immune response against a certain antigen/s. The specific immune response elicited allows the subject to develop an immune response (evoked by an active or passive mode) against e.g. a specific pathogen or a specific tumor.

Pharmaceutical compositions and, in particular vaccines, of the invention are specifically characterized by the manner in which they are administered. Typically, pharmaceutical compositions of the invention, in particular vaccines, are preferably administered systemically. Routes for the administration of such compositions/vaccines typically include transdermal, oral, parenteral, including subcutaneous or intravenous injections, topical and/or intranasal routes. Alternatively, vaccines or pharmaceutical composition of the invention may be administered by an intradermal, subcutaneous, intramuscular route. Compositions/vaccines are therefore formulated preferably in liquid or solid form. Further auxiliary substances (as defined above) can further increase the immunogenicity, in particular of the vaccine, which may preferably be incorporated into a vaccine according to the invention. Advantageously, one or more such auxiliary substances as defined hereinbefore is/are to be chosen, depending on the immunogenicity and other properties of the pharmaceutically active component in the vaccine according to the invention.

According to a further preferred object of the present invention, the pharmaceutical compositions according to the invention, particularly preferably the vaccines according to the invention, are used for the treatment of indications mentioned by way of example hereinbelow. With pharmaceutical compositions according to the invention, particularly preferably vaccines according to the invention, it is possible to treat, for example, diseases or conditions that are associated with various pathologically absent immune responses or that require an immune response, preferably an increased immune response, within the context of a therapy, for example tumour-specific or pathogen-specific diseases, infectious diseases, etc or diseases, which may be treated by shifting the (exceeding) immune response to a TH1 dominated immune response and/or by desensitizing the patient suffering from a exceeding immune response, as e.g. in allergies or autoimmune diseases. The production of such an immune response, or the increase of an already existing but optionally inadequate immune response, by the pharmaceutical composition according to the invention is based substantially on its ability to trigger an a non-antigen-specific immune reaction. An important factor for a suitable immune response is the stimulation of different T-cell sub-populations. T-lymphocytes typically differentiate into two subpopulations, the T-helper 1 (Th1) cells and the T-helper 2 (Th2) cells, with which the immune system is capable of destroying intracellular (Th1) and extracellular (Th2) pathogens (e.g. antigens). The two Th cell populations differ in the pattern of the effector proteins (cytokines) produced by them. Thus, Th1 cells assist the cellular immune response by activation of macrophages and cytotoxic T-cells. Th2 cells, on the other hand, promote the humoral immune response by stimulation of the B-cells for conversion into plasma cells and by formation of antibodies (e.g. against antigens). The Th1/Th2 ratio is therefore of great importance in the immune response. In connection with the present invention, the Th1/Th2 ratio of the immune response is preferably displaced by the pharmaceutical composition according to the invention containing a nucleic acid of either formula (I) or formula (II) according to the invention in the direction towards the cellular response, that is to say the Th1 response, and a predominantly cellular immune response is thereby induced. Only by this displacement and the preferential, or even exclusive, occurrence of a TH1 immune response an efficient treatment of the above-mentioned indications is possible. Preferably, therefore, the present pharmaceutical compositions or vaccines according to the invention are used to trigger tumour-specific or pathogen-specific immune responses. Such pharmaceutical compositions or vaccines according to the invention can be used particularly preferably for increasing immune responses of antigen-presenting cells (APCs). Likewise particularly preferably, the pharmaceutical compositions or vaccines according to the invention can be used for the treatment of cancer or tumour diseases, preferably selected from colon carcinomas, melanomas, renal carcinomas, lymphomas, acute myeloid leukaemia (AML), acute lymphoid leukaemia (ALL), chronic myeloid leukaemia (CML), chronic lymphocytic leukaemia (CLL), gastrointestinal tumours, pulmonary carcinomas, gliomas, thyroid tumours, mammary carcinomas, prostate tumours, hepatomas, various virus-induced tumours such as, for example, papilloma virus-induced carcinomas (e.g. cervical carcinoma), adenocarcinomas, herpes virus-induced tumours (e.g. Burkitt's lymphoma, EBV-induced B-cell lymphoma), heptatitis B-induced tumours (hepatocell carcinoma), HTLV-1- and HTLV-2-induced lymphomas, acoustic neuromas/neurinomas, cervical cancer, lung cancer, pharyngeal cancer, anal carcinomas, glioblastomas, lymphomas, rectal carcinomas, astrocytomas, brain tumours, stomach cancer, retinoblastomas, basaliomas, brain metastases, medulloblastomas, vaginal cancer, pancreatic cancer, testicular cancer, melanomas, thyroidal carcinomas, bladder cancer, Hodgkin's syndrome, meningiomas, Schneeberger disease, bronchial carcinomas, hypophysis tumour, Mycosis fungoides, oesophageal cancer, breast cancer, carcinoids, neurinomas, spinaliomas, Burkitt's lymphomas, laryngeal cancer, renal cancer, thymomas, corpus carcinomas, bone cancer, non-Hodgkin's lymphomas, urethral cancer, CUP syndrome, head/neck tumours, oligodendrogliomas, vulval cancer, intestinal cancer, colon carcinomas, oesophageal carcinomas, wart involvement, tumours of the small intestine, craniopharyngeomas, ovarian carcinomas, soft tissue tumours/sarcomas, ovarian cancer, liver cancer, pancreatic carcinomas, cervical carcinomas, endometrial carcinomas, liver metastases, penile cancer, tongue cancer, gall bladder cancer, leukaemia, plasmocytomas, uterine cancer, lid tumour, prostate cancer, etc. It is particularly preferred, if the lipid used in the lipid-modified nucleic acid or as pharmaceutically active component in the composition is α-tocopherol (vitamin E), D-α-tocopherol, L-α-tocopherol, D,L-α-tocopherol or vitamin E succinate (VES). α-Tocopherol (vitamin E) is not very toxic and exhibits potent anti-tumour activity (A. Bendich, L. J. Machlin Am. *J. Clin. Nutr.* 48 (1988) 612), which makes it appear very promising in cancer therapy. As an explanation for the inhibition of the proliferation of tumour cells or the cytotoxic activity thereon, two mechanisms inter alia are known: On the one hand, vitamin E is a potent antioxidant and a good radical acceptor (C. Borek *Ann. NY Acad. Sci.* 570 (1990) 417); on the other hand, it is able, by stimulating the immune response, to prevent tumour growth (G. Shklar, J. Schwartz, D. P. Trickler, S. Reid *J. Oral Pathol. Med.* 19 (1990) 60). In more recent works, a connection has further been found between the expression of the tumour suppressor gene p53 in tumour cells (oral squamous cancer) and treatment with vitamin E succinate (VES) (J. Schwartz, G. Shklar, D. Trickler *Oral Oncol. Europ. J. Cancer* 29B (1993) 313). It has thereby been possible to observe both a stimulation of the production of wild-type p53, which acts as a tumour suppressor, and a reduction in mutated p53, which develops oncogenic activity. Interestingly, the biological activity of VES on these tumour cells is dose-dependent in two respects: in physiological doses (0.001 to 50 µmol/l), increasing cell growth is to be observed; in pharmacological doses (100 to 154 µmol/l), cell growth is inhibited. This has been shown in cell culture (T. M. A. Elattar, A. S. Virji *Anticancer Res.* 19 (1999) 365). It has also been possible to induce apoptosis in various breast cancer cell lines by treatment with VES (W. Yu, K. Israel, Q. Y. Liao, C. M. Aldaz, B. G. Sanders, K. Kline *Cancer Res.* 59 (1999) 953). The induced apoptosis is initiated via an interaction of Fas ligand and Fas receptor. This is to be particularly emphasised because it has hitherto not been possible to observe such a mechanism in the corresponding cell lines. There are various isomers of vitamin E, which differ in the number and position of the methyl groups on the aromatic ring. In the described works, the biologically most active form of naturally occurring vitamin E, α-tocopherol, was used. This in turn occurs in various stereoisomers, because the molecule contains three optically active centres. The natural form of vitamin E is RRR-α-tocopherol (formerly D-α-tocopherol), but the racemate (D,L-α-tocopherol) is predominantly used nowadays. All the above-mentioned forms of vitamin E are likewise included as lipid within the scope of the present invention.

Likewise particularly preferably, the pharmaceutical compositions according to the invention are used for the treatment of infectious diseases. Without implying any limitation, such infectious diseases are preferably selected from influenza, malaria, SARS, yellow fever, AIDS, Lyme borreliosis, Leishmaniasis, anthrax, meningitis, viral infectious diseases such as AIDS, Condyloma acuminata, hollow warts, Dengue fever, three-day fever, Ebola virus, cold, early summer meningoencephalitis (FSME), flu, shingles, hepatitis, herpes simplex type I, herpes simplex type II, Herpes zoster, influenza, Japanese encephalitis, Lassa fever, Marburg virus, measles, foot-and-mouth disease, mononucleosis, mumps, Norwalk virus infection, Pfeiffer's glandular fever, smallpox, polio (childhood lameness), pseudo-croup, fifth disease, rabies, warts, West Nile fever, chickenpox, cytomegalic virus (CMV), from bacterial infectious diseases such as miscarriage (prostate inflammation), anthrax, appendicitis, borreliosis, botulism, *Camphylobacter, Chlamydia trachomatis* (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, leprosy, listeriosis, pneumonia, meningitis, bacterial meningitis, anthrax, otitis media, *Mycoplasma hominis*, neonatal sepsis (Chorioamnionitis), noma, paratyphus, plague, Reiter's syndrome, Rocky Mountain spotted fever, *Salmonella* paratyphus, *Salmonella* typhus, scarlet fever, syphilis, tetanus, tripper, tsutsugamushi disease, tuberculosis, typhus, vaginitis (colpitis), soft chancre, and from infectious diseases caused by parasites, protozoa or fungi, such as amoebiasis, bilharziosis, Chagas disease, athlete's foot, yeast fungus spots, scabies, malaria, onchocercosis (river blindness), or fungal diseases, toxoplasmosis, trichomoniasis, trypanosomiasis (sleeping sickness), visceral Leishmaniosis, nappy/diaper dermatitis, schistosomiasis, fish poisoning (Ciguatera), candidosis, cutaneous Leishmaniosis, lambliasis (giardiasis), or sleeping sickness, or from infectious diseases caused by *Echinococcus*, fish tapeworm, fox tapeworm, canine tapeworm, lice, bovine tapeworm, porcine tapeworm, miniature tapeworm.

Accordingly, the nucleic acid of the invention or the pharmaceutically active compositions of the invention may be used for the preparation of a medicament for the treatment of an allergic disorder or disease. Allergy is a condition that typically involves an abnormal, acquired immunological hypersensitivity to certain foreign antigens or allergens. Allergies normally result in a local or systemic inflammatory response to these antigens or allergens and leading to an immunity in the body against these allergens. Allergens in this context include e.g. grasses, pollens, molds, drugs, or numerous environmental triggers, etc. Without being bound to theory, several different disease mechanisms are supposed to be involved in the development of allergies. According to a classification scheme by P. Gell and R. Coombs the word "allergy" was restricted to type I hypersensitivities, which are caused by the classical IgE mechanism. Type I hypersensitivity is characterised by excessive activation of mast cells and basophils by IgE, resulting in a systemic inflammatory response that can result in symptoms as benign as a runny nose, to life-threatening anaphylactic shock and death. Well known types of allergies include, without being limited thereto, allergic asthma (leading to swelling of the nasal mucosa), allergic conjunctivitis (leading to redness and itching of the conjunctiva), allergic rhinitis ("hay fever"), anaphylaxis, angiodema, atopic dermatitis (eczema), urticaria (hives), eosinophilia, respiratory, allergies to insect stings, skin allergies (leading to and including various rashes, such as eczema, hives (urticaria) and (contact) dermatitis), food allergies, allergies to medicine, etc. With regard to the present invention, e.g. a pharmaceutical composition is provided, which contains an allergen (e.g. from a cat allergen, a dust allergen, a mite antigen, a plant antigen (e.g. a birch antigen) etc.) either as a protein, an mRNA (or DNA) encoding for that protein allergen in combination with a nucleic acid of the invention. Pharmaceutical compositions of the present invention may shift the (exceeding) immune response to a stronger TH1 response, thereby suppressing or attenuating the undesired IgE response.

Likewise, the present invention provides medicaments for the treatment of autoimmune diseases. Autoimmune diseases can be broadly divided into systemic and organ-specific or localised autoimmune disorders, depending on the principal clinico-pathologic features of each disease. Autoimmune disease may be divided into the categories of systemic syndromes, including SLE, Sjögren's syndrome, Scleroderma, Rheumatoid Arthritis and polymyositis or local syndromes which may be endocrinologic (DM Type 1, Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus), systemic lupus erythematosus (SLE), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), psoriasis, Reiter's syndrome, rheumatic arthritis, psoriasis, vasculitis, etc, or type II diabetes.

While the exact mode as to why the immune system induces a immune reaction against autoantigens has not been elucidated so far, there are several findings with regard to the etiology. Accordingly, the autoreaction may be due to a T-Cell Bypass. A normal immune system requires the activation of B-cells by T-cells before the former can produce antibodies in large quantities. This requirement of a T-cell can be by-passed in rare instances, such as infection by organisms producing super-antigens, which are capable of initiating polyclonal activation of B-cells, or even of T-cells, by directly binding to the β-subunit of T-cell receptors in a non-specific fashion. Another explanation deduces autoimmune diseases from a Molecular Mimicry. An exogenous antigen may share structural similarities with certain host antigens; thus, any antibody produced against this antigen (which mimics the self-antigens) can also, in theory, bind to the host antigens and amplify the immune response. The most striking form of molecular mimicry is observed in Group A beta-haemolytic streptococci, which shares antigens with human myocardium, and is responsible for the cardiac manifestations of Rheumatic Fever. The present invention allows therefore to provide a pharmaceutical composition containing an autoantigen (as protein, mRNA or DNA encoding for a autoantigen protein) and a nucleic acid of the invention which typically allows the immune system to be desensitized.

The invention relates also to the use of the nucleic acid of either formula (I) or formula (II) according to the invention, as described above, or both, in the preparation of a pharmaceutical composition according to the invention or of a vaccine according to the invention for the treatment of indications described hereinbefore, for example for the treatment of the mentioned tumour, autoimmune diseases, allergies and infectious diseases. Alternatively, the invention includes the (therapeutic) use of a nucleic acid of either formula (I) or formula (II) according to the invention, or both, for the treatment of tumour or infectious diseases, as described hereinbefore.

Likewise included in the present invention are kits containing a nucleic acid of either formula (I) or formula (II) according to the invention, or both, and/or a pharmaceutical composition according to the invention and/or a vaccine according to the invention as well as, optionally, technical instructions for use with information on the administration and dosage of the nucleic acid of either formula (I) or formula (II) according to the invention and/or of the pharmaceutical composition according to the invention and/or of the vaccine according to the invention.

Methods of treating a disorder or disease selected from the group consisting of cancer diseases, infectious diseases, autoimmune diseases and allergies by administering to a patient in need thereof a pharmaceutically effective amount of a nucleic acid according to the invention.

The present invention is illustrated further hereinbelow by means of figures and examples, which are not intended to limit the subject-matter of the invention thereto.

DESCRIPTION OF THE FIGURES

FIG. 4 discloses SEQ ID NO: 94.

EXAMPLES

1. Synthesis of Exemplary Nucleic Acids of Formula (I) According to the Invention RNA oligonucleotides, as examples of the nucleic acid of the general formula (I) $G_lX_mG_n$ and of the general formula (II) $C_lX_mC_n$ according to the invention, were prepared by automatic solid-phase synthesis by means of phosphoramidite chemistry. In each case the RNA-specific 2'-hydroxyl groups of the nucleotides were protected with TBDMS protecting groups. In the synthesis of phosphorothioates, Beaucage reagent was used for the oxidation. The cleavage of carrier material and of the base-labile protecting groups was carried out with methylamine, and the cleavage of the TBDMS protecting group was effected with triethylamine hydrofluoride.

The crude product was purifed by means of HPLC either by ion-pair chromatography, by ion-exchange chromatography or by a combination of the two methods, desalinated and dried. The product was checked for purity and correct base composition by mass spectrometry.

Figure 1:
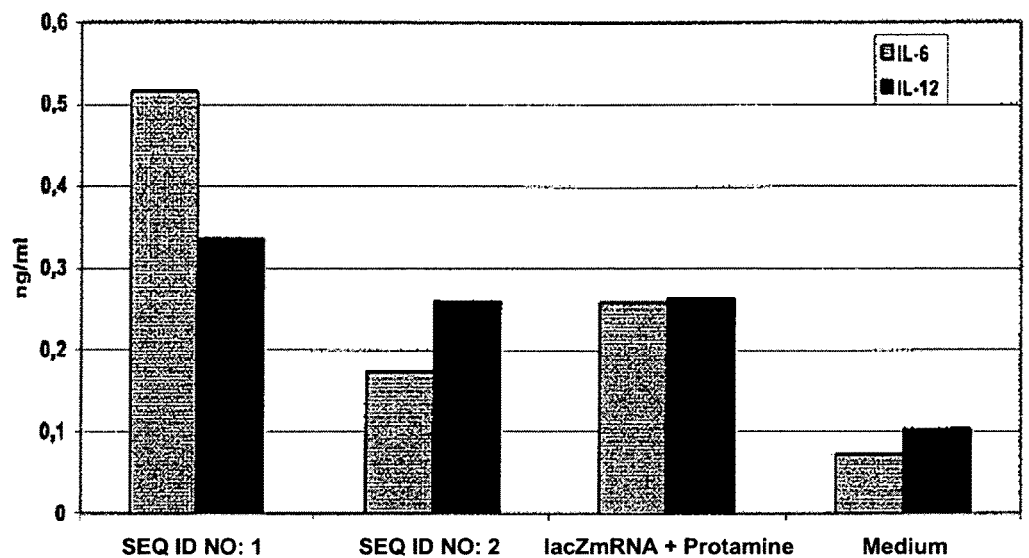
FIG. 1: shows the stimulation of mouse BMDCs (bone marrow dendritic cells) with nucleic acids according to the invention of SEQ ID NOs: 1 and 2. A stimulation can be observed most clearly in the case of SEQ ID NO: 1. The release of IL-6 and IL-12 (ng/ml) was measured as a measure of the immune stimulation (see Example 2). As positive control there was used the immune-stimulating uncapped wild-type mRNA of beta-galactosidase (lacZ), complexed with protamine.
Figure 2:
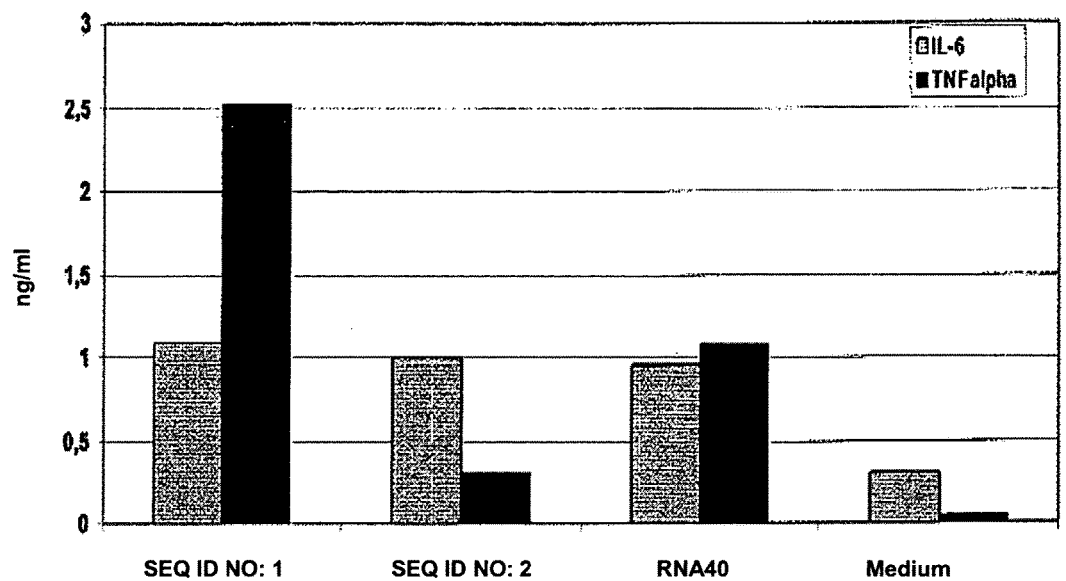
FIG. 2: shows the stimulation of human PBMCs (hPB-MCs) with oligonucleotides according to the invention of SEQ ID NOs: 1 and 2. A stimulation can be observed most clearly in the case of SEQ ID NO: 1. The release of interleukin-6 (IL-6) and TNF alpha (ng/ml) was measured as a measure of the immune stimulation (see Example 2).
Figure 3:
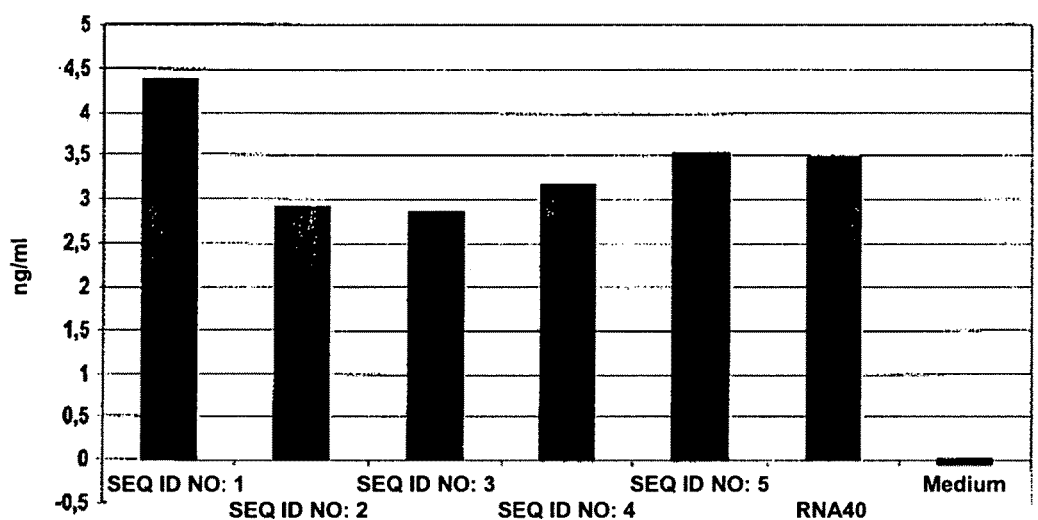
FIG. 3: shows the stimulation of human PBMCs (hPB-MCs) with oligonucleotides according to the invention of SEQ ID NOs: 1, 2, 3, 4 and 5. A stimulation can be observed most clearly in the case of SEQ ID NO: 1. The release of interleukin-6 (IL-6) (ng/ml) was measured as a measure of the immune stimulation (see Example 2).
Figure 4:
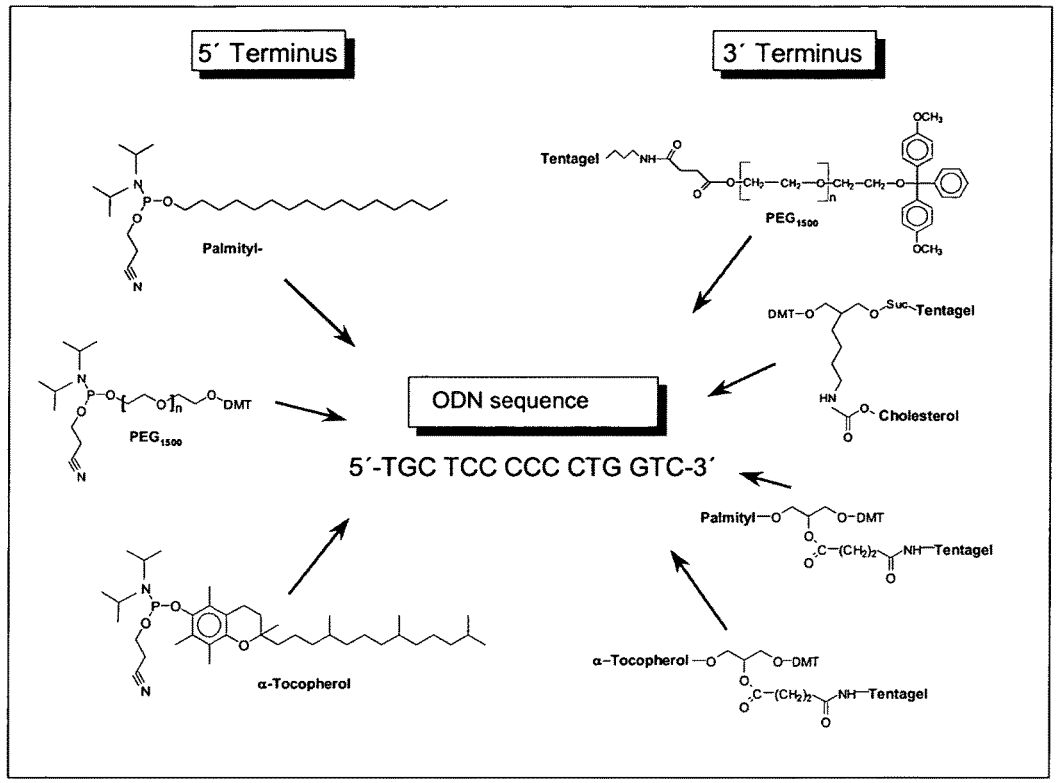
FIG. 4: shows various possibilities according to the invention for the terminal modification of nucleic acids of either formula (I) or formula (II) according to the invention with lipids. There are shown in particular the lipid-modified linkers and bifunctional peptides, respectively, which can be used for coupling or synthesis with nucleic acid sequences (ODN sequence for short).
Figure 5:
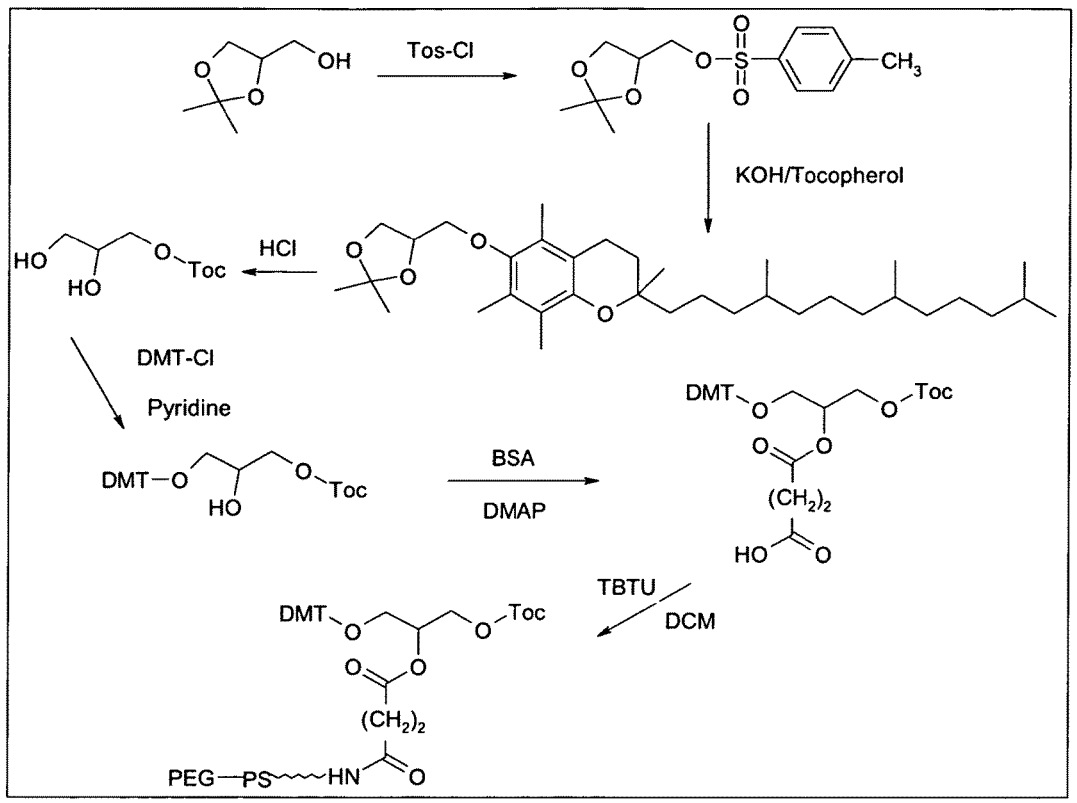
FIG. 5: describes by way of example a synthesis route for (trifunctional) lipid-modified linkers, with which, for example, a tocopherol modification can be introduced at the 3' end of a nucleic acid. Such compounds shown by way of example represent an intermediate in the preparation of the 5'- or 3'-lipid-modified nucleic acids according to the invention and of the adjuvants according to the invention.
Figure 6:
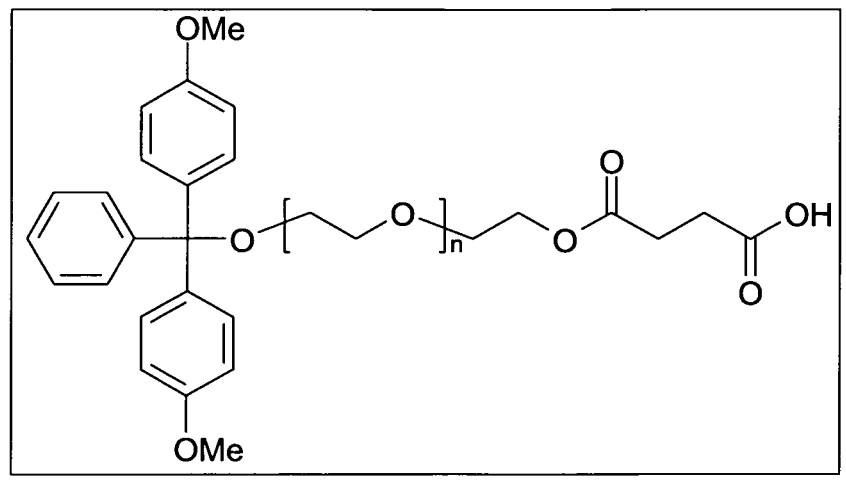
FIG. 6: shows by way of example a bifunctional lipid with a succinyl anchor, which permits a 3'-modification of a nucleic acid with a bifunctional lipid, for example with PEG.
Figure 7:
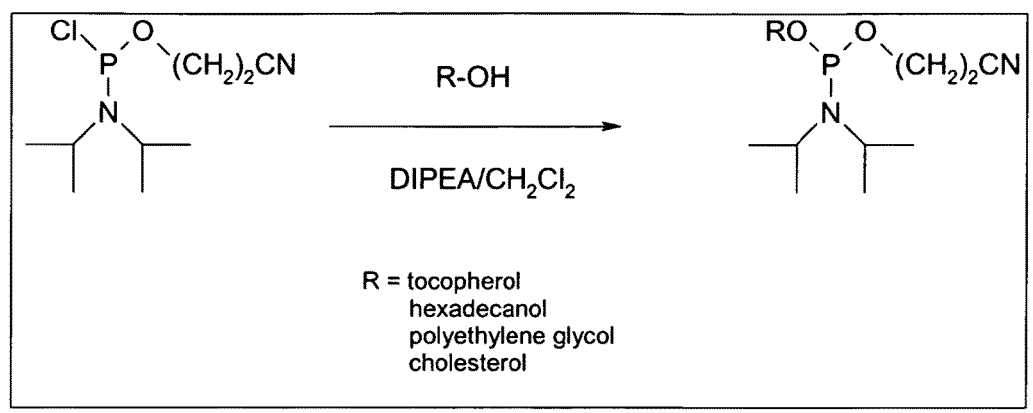
FIG. 7: shows diagrammatically the coupling of lipid-modified amidites to the 5' end of nucleic acids.

2. In Vitro Immune Stimulation with Exemplary Nucleic Acids of Formula (I) According to the Invention a) For the stimulation of mouse BDMCs (bone marrow derived dendritic cells), 3 µl of oligofectamine were mixed with 30 µl of FCS-free IMDM medium (Bio-Whittaker, catalogue no. BE12-722F) and incubated at room temperature for 5 minutes. 6 µg of the nucleic acids of formula (I) according to the invention of SEQ ID NOs: 1-2, in the form of RNA, were mixed with 60 µl of FCS-free IMDM and mixed with oligofectamine/IMDM, and incubated for 20 minutes at room temperature. 33 µl of this mixture were then placed for cultivation overnight in a well of a 96-well microtitre culture plate which contained 200,000 mouse BDMCs in 200 µl of FCS-free IMDM medium. After 4 hours, 100 µl of IMDM containing 20% FCS were added and, after 16 hours' co-incubation, the supernatant was removed and tested for interleukin-6 (IL-6) and interleukin-12 (IL-12) by a cytokine ELISA. Comparison tests were carried out analogously to the sequences SEQ ID NOs: 1 and 2 according to the invention using the immune-stimulating uncapped wild-type mRNA of beta-galactosidase (lacZ), complexed with protamine. It was possible to show that the nucleic acids of formula (I) according to the invention, present in the form of RNA, in particular the sequences according to the invention of SEQ ID NOs: 1 and 2, have good immune-stimulating properties. SEQ ID NO: 1 in particular showed immune stimulation that substantially exceeded the stimulatory properties of the immune-stimulating uncapped wild-type mRNA of beta-galasctosidase (lacZ) used for comparison purposes.

b) Human PBMCs were obtained via a Ficoll density gradient and cultivation overnight in X-VIVO-15 medium (BioWhittaker, catalogue no. BE04-418Q), which contained 1% glutamine and 1% penicillin in the presence of 10 µg/ml of the nucleic acids of formula (I) according to the invention in the form of RNA, in particular of the sequences according to the invention SEQ ID NO: 1 and 2 (see FIG. 2) and SEQ ID NO: 1-5 (see FIG. 3), respectively.

For stimulation, 3 µl of oligofectamine were mixed with 30 µl of X-VIVO-15 medium (BioWhittaker, catalogue no. BE04-418Q) and incubated at room temperature for 5 minutes. 6 µg of the nucleic acids of formula (I) according to the invention in the form of RNA, in particular the sequences according to the invention SEQ ID NO: 1 and 2 (see FIG. 2) and SEQ ID NO: 1-5 (see FIG. 3), respectively, were mixed with 60 µl of X-VIVO-15 medium (BioWhittaker, catalogue no. BE04-418Q) and, mixed with oligofectamine/X-VIVO medium, incubated for 20 minutes at room temperature. 33 µl of this mixture were then placed for cultivation overnight in a well of a 96-well microtitre culture plate which contained 200,000 PBMCs in 200 µl of X-VIVO-15 medium (BioWhittaker, catalogue no. BE04-418Q). After co-incubation for 16 hours, the supernatant was removed and tested for interleukin-6 (IL-6) and interleukin-12 (IL-12) and TNFα by means of a cytokine-ELISA. Comparison tests were carried out analogously to the sequences according to the invention SEQ ID NO: 1 and 2 with the immune-stimulating oligo RNA40 (5'-GCCCGUCUGUUGU-GUGACUC-3', SEQ ID NO: 87).

It was possible to show that the nucleic acids of formula (I) according to the invention in the form of RNA, in particular having the sequences according to the invention SEQ ID NO: 1 and 2 (see FIG. 2) and SEQ ID NO: 1-5 (see FIG. 3), respectively, have good immune-stimulating properties. SEQ ID NO: 1 in particular exhibited immune stimulation that substantially exceeded the stimulatory properties of the RNA oligonucleotide used for comparison purposes.

3. In Vivo Immune Stimulation with Exemplary Nucleic Acids of Formula (I) According to the Invention—Use as Adjuvant BALB/c mice (5 per group) were injected with β-galactosidase protein and with an adjuvant (as defined herein) on days 0 and 10. The mice were sacrificed on day 20 and the blood serum was used for an antibody test against β-galactosidase protein by means of ELISA, and the IL-6, IL-12 and TNF-α values were determined analogously to the above-described in vitro cultures.

4. Synthesis of 1-(4,4'-dimethoxytrityl)-polyethylene glycol (DMT-PEG$_{1500}$)

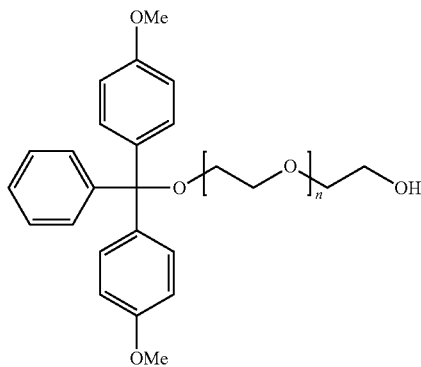

Procedure:

21 g of PEG$_{1500}$ (14 mmol) are dissolved twice, for drying, in 30 ml of absolute pyridine each time, which is subsequently distilled off azeotropically. The dried starting material is dissolved in 35 ml of abs. pyridine. 4.7 g of 4,4'-dimethoxytrityl chloride (13.9 mmol) dissolved in 35 ml of abs. pyridine are added dropwise to this solution over a period of 30 minutes. Stirring is carried out for a further 2 hours at RT, during which the progress of the reaction is monitored by means of TLC. In addition to detection of the DMT group by means of a UV lamp, the TLC plates can be developed in two steps: 1. in an HCl-saturated atmosphere for the detection of DMT; 2. in an iodine chamber for the detection of PEG; PEG can additionally be detected with Dragendorff-Bürger spray reagent. When the reaction is complete, the solvent is removed and the product is taken up in 50 ml of DCM. The organic phase is washed twice with 25 ml of 5% NaHCO$_3$ solution and twice with 25 ml of H$_2$O. Phase separation between aqueous and organic phase is tedious because PEG is of both hydrophobic and hydrophilic nature. After drying over Na$_2$SO$_4$, the solvent is removed and the crude product is purified by column chromatography on silica gel with DCM/MeOH/TEA=18:2:0.5. The product-containing fractions are identified by means of TLC, combined and concentrated to dryness. A yellowish oil is obtained which, after thorough drying under a high vacuum, becomes a wax-like solid.

Yield: 18.3 g (72.5% of theory)

TLC (DCM/MeOH/TEA=18:2:0.5): R$_f$ value≈0.55 (signal spread by the molar mass distribution of PEG)

5. Synthesis of 1-(4,4'-dimethoxytrityl)-hexaethylene glycol (DMT-HEG)

Procedure:

10 g of hexaethylene glycol (35 mmol) are dried by coevaporation with 2×30 ml of abs. pyridine and then dissolved in 20 ml of abs. pyridine. Analogously to the procedure of Example 1, the HEG is reacted with 10 g of DMT-Cl (29.5 mmol) dissolved in 50 ml of abs. pyridine. Purification by column chromatography is carried out with ethyl acetate/TEA=95:5. A viscous, yellow oil is obtained as the dried product.

Yield: 12.5 g (60.5% of theory)

TLC (DCM/MeOH=95:5): R$_f$ value t=0.59

MS (FD): m/z 583.9 (M$^+$)

$^1$H-NMR (CDCl$_3$): δ 3.21 (t, DMT-O—CH$_2$—), 3.47-3.68 (m, —CH$_2$—), 3.76 (s, —CH$_3$), 6.77-7.46 (m, aromatic compound)

6. Synthesis of 1-(4,4'-dimethoxytrityl)-polyethylene glycol succinate (DMT-PEG-Suc)

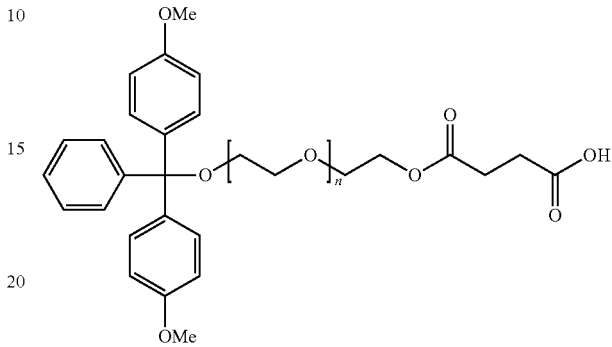

The procedure below can be used for both DMT-PEG$_{1500}$ and DMT-HEG.

Procedure:

5 g of DMT-PEG$_{1500}$ (2.8 mmol) are dissolved in 25 ml of DCM/pyridine=5:1, and 420 mg of succinic anhydride (4.2 mmol, i.e. 1.5 eq.) dissolved in 7 ml of pyridine, and 170 mg of DMAP (1.4 mmol, i.e. 0.5 eq.) dissolved in 3 ml of pyridine are added thereto. After 12 hours' stirring at RT, the solvents are removed in vacuo and the residue is taken up in DCM. The organic phase is washed thoroughly three times with NaHCO$_3$ solution (10% in H$_2$O) and twice with saturated aqueous NaCl solution, in order to separate off the excess succinic acid. After drying over Na$_2$SO$_4$, the solvent is removed. After thorough drying under a high vacuum, the succinates can be used without further working up for coupling to amino-modified carrier materials.

TLC: DMT-PEG$_{1500}$-Suc (DCM/MeOH/TEA=18:2:0.5): R$_f$ value=0.41

DMT-HEG-Suc (DCM/MeOH=9:2): R$_f$ value=0.70

7. Synthesis of 1-tosyl-2,3-isopropylideneglycerol

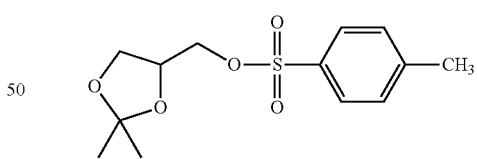

Procedure:

200 mmol of isopropylideneglycerol (26.4 g) are dissolved in 200 ml of acetonitrile, and 22.2 g of triethylamine (220 mmol) are added thereto. 220 mmol of p-toluenesulfonic acid chloride (41.9 g) are dissolved in 250 ml of acetonitrile and added dropwise to the reaction mixture, with stirring, over a period of 2 hours. Stirring is continued for a further 20 hours at RT, whereupon a white precipitate forms, which is filtered off when the reaction is complete. The solvent is removed and the crude product is purified by column chromatography on silica gel with n-hexane/ethyl acetate=2:1. The product-containing fractions are identified by means of TLC, combined and concentrated to dryness. The product is dried under a high vacuum. A yellowish oil is obtained (L. N. Markovskii et al. *J. Org. Chem. UdSSR* 26 (1990) 2094.).

Yield: 31.3 g (54.7% of theory)
TLC (n-hexane/ethyl acetate=2:1): $R_f$ value=0.2
MS (FD): m/z 272.0 ($M^+$-CH) (286.3 calculated)
$^1$H-NMR (CDCl$_3$): δ 1.31 (s); 1.34 (s); 2.45 (s); 3.74-3.79 (m); 3.90-4.08 (m); 4.23-4.32 (m); 7.36 (d); 7.77 (d)
$^{13}$C-NMR: δ 21.7; 25.2; 26.7 (methyl-C); 66.2; 69.5; 72.9 (glycerol-C); 110.1 (methylene-C); 128.0; 129.9; 132.7; 145.1 (aromatic compound-C)

8. Synthesis of 2,3-isopropylidene-1-D,L-α-tocopherolglycerol (Toc1)

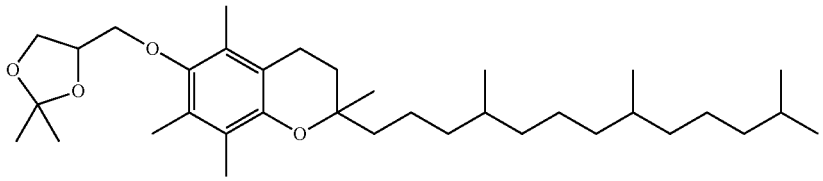 [SMILES: Cc1c(C)c2c(c(C)c1OCC1COC(C)(C)O1)CCC(C)(CCCC(C)CCCC(C)CCCC(C)C)O2]

Procedure:
5.6 g of powdered potassium hydroxide (100 mmol) are added to 56 mmol of D,L-α-tocopherol (24.06 g) in 280 ml of DMSO. After 2 hours' stirring at RT with the exclusion of light, 56 mmol of 1-tosyl-2,3-isopropylidene-glycerol (16 g) dissolved in 20 ml of DMSO are added dropwise, and stirring is continued for a further 12 hours at 60° C. The reaction mixture is then hydrolysed on 1 liter of ice-water, and the aqueous phase is extracted with 1.5 liters of toluene. After drying over sodium sulfate, the solvent is removed. The crude product is purified by column chromatography on silica gel with n-hexane/ethyl acetate=1:1. The product-containing fractions are identified by means of TLC, combined and concentrated to dryness. The product is dried under a high vacuum and stored with the exclusion of light. A yellowish oil is obtained (D. W. Will, T. Brown *Tetrahedron Lett.* 33 (1992) 2729.).

Yield: 24.2 g (79.2% of theory)
TLC (n-hexane/ethyl acetate=1:1): $R_f$ value=0.69
MS (FD): m/z 544.6 ($M^+$)

9. Synthesis of 1-D,L-α-tocopherylglycerol (Toc2)

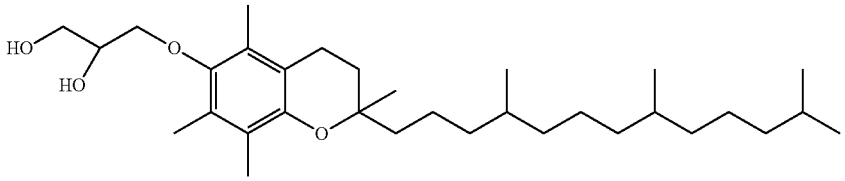 [SMILES: Cc1c(C)c2c(c(C)c1OCC(O)CO)CCC(C)(CCCC(C)CCCC(C)CCCC(C)C)O2]

Procedure:
16.9 mmol of Toc1 (9.2 g) are dissolved in 100 ml of HCl(2 M)/THF (1:1) and stirred for 2 hours at RT with the exclusion of light. The solvent is then removed, 2×50 ml of absolute ethanol are added to the residue, and the mixture is concentrated to dryness again. The crude product is purified by column chromatography on silica gel with diethyl ether/toluene=1:1. The product-containing fractions are identified by TLC, combined and concentrated to dryness. The product is dried under a high vacuum and stored with the exclusion of light. A yellow oil is obtained.

Yield: 6.6 g (77.5% of theory)
TLC (diethyl ether/toluene=1:1): $R_f$ value=0.22
MS (FD): m/z 504.4 ($M^+$)

10. Synthesis of [1-(4,4'-dimethoxytrityl)]-3-D,L-α-tocopherylglycerol (Toc3)

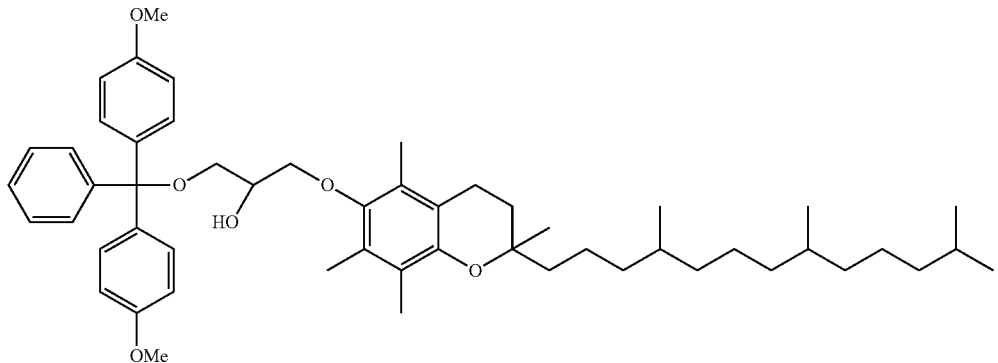 [SMILES: COc1ccc(C(OCC(O)COc2c(C)c(C)c3c(c2C)CCC(C)(CCCC(C)CCCC(C)CCCC(C)C)O3)(c2ccccc2)c2ccc(OC)cc2)cc1]

Procedure:

6.6 g of Toc2 (13 mmol) are dissolved twice for drying in 15 ml of absolute pyridine, which is distilled off again azeotropically. The dried starting material is dissolved in 50 ml of absolute pyridine, and 5.34 g of DMT-Cl (15.8 mmol) are added thereto. After 12 hours' stirring at RT with the exclusion of light, the reaction is terminated by addition of 50 ml of methanol, and the reaction mixture is concentrated to dryness. The residue is taken up in 500 ml of dichloromethane and washed twice with 150 ml of aqueous, saturated NaCl solution and then once with 150 ml of water. After drying over $Na_2SO_4$, the solvent is removed and the residue is purified by column chromatography on silica gel (n-hexane/diethyl ether/triethylamine=40:60:1). The product-containing fractions are identified by means of TLC, combined and concentrated to dryness. The product is dried under a high vacuum. A yellowish oil is obtained, which is stored with the exclusion of light.

Yield: 8.5 g (81% of theory)
TLC (n-hexane/diethyl ether/TEA=40:60:1): $R_f$ value=0.43
MS (FD): m/z 807.2

11. Synthesis of [1-(4,4'-dimethoxytrityl)]-2-succinyl-3-D,L-α-tocopherylglycerol (Toc4)

Procedure:

1.45 g of Toc3 (1.8 mmol) are dissolved twice, for drying, in 5 ml of abs. pyridine each time, which is distilled off again azeotropically. When the starting material has been dissolved in 8 ml of abs. pyridine, 140 mg of DMAP (1.08 mmol) and 194.4 mg of succinic anhydride (1.8 mmol) are added thereto in an argon countercurrent. Stirring is then carried out for 18 hours at RT with the exclusion of light. For working up, 45 ml of DCM are added to the reaction solution, and washing is carried out four times with 50 ml of water each time. After drying over sodium sulfate, the solvent is removed and the crude product is purified by column chromatography on silica gel with ethyl acetate/methanol/$NH_3$ (25% in $H_2O$)=5:1:1. The product-containing fractions are identified by means of TLC, combined and concentrated to dryness. After drying under a high vacuum, a brownish, viscous oil is obtained and stored with the exclusion of light.

Yield: 1.35 g (82.8% of theory)
TLC (EtOAc/$NH_3$/MeOH=5:1:1): $R_f$ value=0.30
MS (FD): m/z 906.2 ($M^+$), 604.2 ($M^+$-DMT)

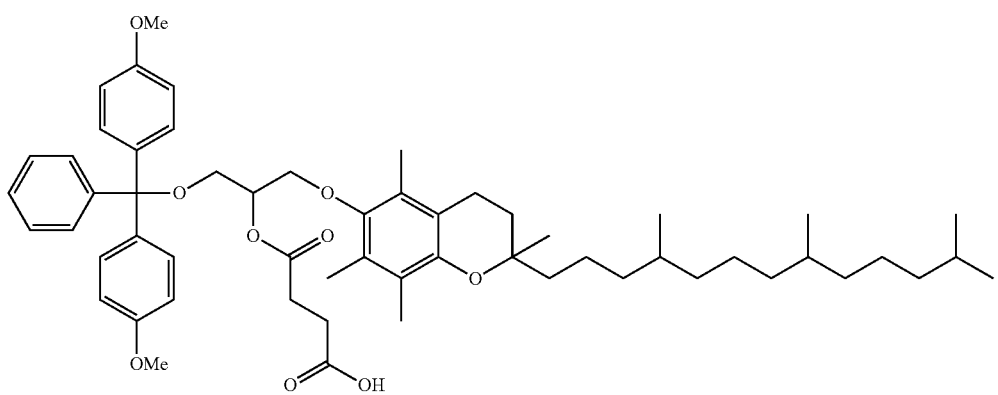 [SMILES: COc1ccc(C(OCC(COc2c(C)c(C)c3c(c2C)CCC(C)(CCCC(C)CCCC(C)CCCC(C)C)O3)OC(=O)CCC(=O)O)(c2ccccc2)c2ccc(OC)cc2)cc1]

12. Synthesis of D,L-α-tocopheryl-β-cyanoethyl-N,N-diisopropyl-phosphoramidite

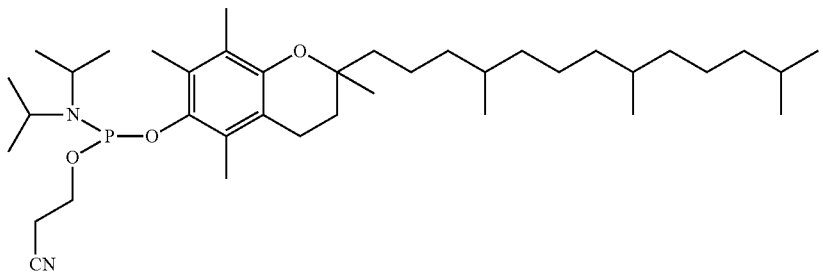 [SMILES: Cc1c(C)c2c(c(C)c1OP(OCCC#N)N(C(C)C)C(C)C)CCC(C)(CCCC(C)CCCC(C)CCCC(C)C)O2]

Procedure:

2×25 ml of pyridine are added to 5 g of D,L-α-tocopherol (11.6 mmol), and the mixture is dried by azeotropic entrainment. The starting material is dissolved in 40 ml of $DCM_{abs}$. In an argon counter-current, 7.9 ml of $DIPEA_{abs}$ (46.4 mmol) and 2.5 ml of 2-cyanoethyl-N,N-diisopropylphosphine chloride (11 mmol) are slowly added dropwise. When the reaction mixture has been stirred for 1 hour at RT with the exclusion of light, it is diluted with 100 ml of ethyl acetate/TEA (20:1) and washed twice with 25 ml of 10% $NaHCO_3$ and twice with saturated NaCl solution. The organic phase is then dried over $Na_2SO_4$ and the solvent is removed in vacuo. The crude product is purified by column chromatography on silica gel with ethyl acetate.

Yield: 5.62 g (81% of theory)
TLC (EtOAc): $R_f$ value=0.75
MS (FD): ink 630.1 ($M^+$)
$^{31}$P-NMR: δ 152.24

13. Synthesis of [1-(4,4'-dimethoxytrityl)]-(3-D,L-α-tocopheryl)-glycerol-2-phosphoramidite

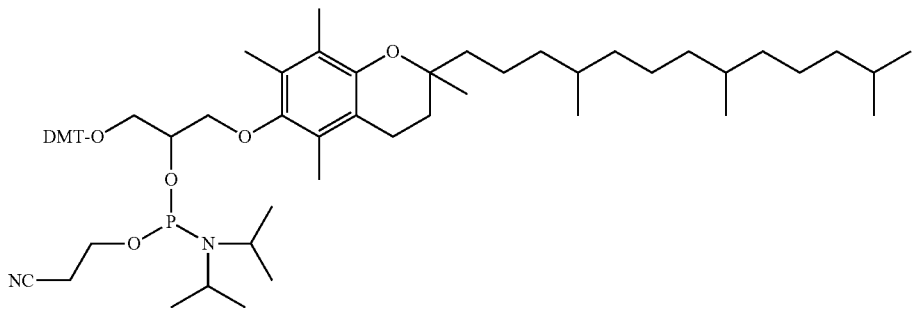

Procedure:

1 g of Toc3 (1.24 mmol) is dissolved twice, for drying, in 10 ml of abs. pyridine each time, which is distilled off again azeotropically. The starting material is then dissolved in 20 ml of $DCM_{abs}$, and 0.84 ml of $DIPEA_{abs}$ (4.96 mmol) are added dropwise under an argon counter-current. 0.27 ml of 2-cyanoethyl-N,N-diisopropylphosphine chloride (1.19 mmol) are then slowly added dropwise in an argon counter-current. The reaction mixture is stirred for 1 hour at RT, thereafter the solution is diluted with 50 ml of ethyl acetate/TEA (20:1). The organic phase is washed twice with 15 ml of a 10% $NaHCO_3$ solution and twice with a saturated NaCl solution and then dried over $Na_2SO_4$. The solvent is removed and the crude product is purified by column chromatography on silica gel with ethyl acetate/TEA (99:1).

The product-containing fractions are identified by means of TLC, combined and concentrated to dryness. After drying under a high vacuum, a yellowish-brown, very viscous oil is obtained, which is cooled and stored with the exclusion of light.

Yield: 0.76 g (63.4% of theory)
TLC (EtOAc, 1% TEA): $R_f$ value=0.68
MS (FD): m/z 1006.4 ($M^+$), 953.6 ($M^+$-cyanoethyl), 651.4 ($M^+$-DMT,-cyanoethyl),
603.1 ($M^+$-DMT,-diisopropylamine), 303.1 ($DMT^+$)
$^{31}$P-NMR: δ 150.5

14. Synthesis of 1-hexadecyl-2,3-isopropylideneglycerol (Pam1)

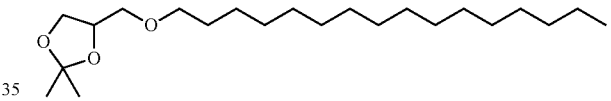

Procedure:

0.11 mol of sodium hydride (2.42 g) is added in portions, under an argon counter-current, to 0.1 mol of D,L-α,β-isopropylidene-glycerol (12.4 ml) in 500 ml of $THF_{abs}$. After 12 hours' stirring at RT, 0.11 mol of 1-bromohexadecane (33.6 ml) in 80 ml of $THF_{abs}$ is added dropwise to the resulting alcoholate. After addition of 0.5 mmol of tetrabutylammonium iodide as catalyst, the mixture is heated at boiling for 12 hours. After cooling of the reaction mixture, the resulting sodium bromide is filtered off and the filtrate is concentrated to dryness. The residue is taken up in diethyl ether and the ether phase is extracted by shaking three times with $H_2O$. After drying of the organic phase over $Na_2SO_4$, the mixture is concentrated to dryness and the residue is purified by column chromatography on silica gel (EtOAc/n-hexane=1:9) (S. Czernecki, C. Georgoulis, C. Provelenghiou *Tetrahedron Lett.* 39 (1976) 3535).

Yield: 18.5 g (52% of theory)
TLC (EtOAc/n-hexane=1:9): $R_f$ value=0.47
MS (FD): m/z 357.6 ($M^+ +1$)
$^1$H-NMR (CDCl$_3$): δ 0.80 (t), 1.18 (s), 1.35 (s), 1.37 (s), 3.30-3.48 (m), 3.63-3.69 (dd), 3.96-4.01 (dd), 4.19 (q)
$^{13}$C-NMR (CDCl$_3$): δ 14.1; 22.7; 25.4; 26.1; 26.8; 29.4; 29.6; 29.7; 31.9 (alkyl chain), 67.0 (alkyl-C—O—), 71.8; 71.9; 74.7 (glycerol-C), 109.3 (ketyl-C)

15. Synthesis of 1-hexadecylglycerol (Pam2)

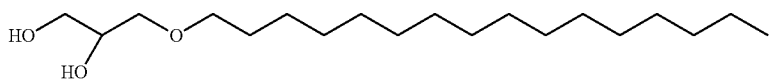 [SMILES: CCCCCCCCCCCCCCCCOCC(O)CO]

Procedure:

18.5 g of Pam1 (52 mmol) are stirred in 300 ml of acetic acid (65%) for 24 hours at 40° C. The white precipitate is filtered off and concentrated to dryness several times with n-hexane. For purification, the product is suspended three times in n-hexane and filtered off. Starting material that has not been deprotected, unlike the product, is soluble in n-hexane and can accordingly be separated off. The residue that remains is dried in vacuo. The combined filtrates are likewise concentrated to dryness and again subjected to the separation procedure (H. Paulsen, E. Meinjohanns, F. Reck, I. Brockhausen *Liebigs Ann. Chem.* (1993) 721).

Yield: 14.6 g (88% of theory)
TLC (EtOAc/n-hexane=1:1): $R_f$ value=0.2
MS (FD): m/z 317.4 ($M^+ +1$)
$^1$H-NMR (CDCl$_3$): δ 0.86 (t), 1.23 (s), 3.30-3.48 (m), 3.41-3.49 (m), 3.55-3.75 (m), 3.78-3.9 (m)
$^{13}$C-NMR (CDCl$_3$): δ 14.1; 22.7; 25.4; 26.1; 29.4; 29.5; 29.6; 31.9 (alkyl chain), 70.5 (alkyl-C—O—), 64.2; 71.8; 72.4 (glycerol-C)

16. Synthesis of [1-(4,4'-dimethoxytrityl)]-3-hexadecylglycerol (Pam3)

Procedure:

For drying, 10 mmol of Pam2 (3.16 g) are dissolved in 15 ml of pyridine$_{abs}$ and the solvent is removed again. This procedure is repeated. 12 mmol (4.06 g) of dimethoxytrityl chloride (dissolved in 50 ml of pyridine) are slowly added dropwise to a solution of the diol in 100 ml of pyridine$_{abs}$, and stirring is carried out for 24 hours at RT. The reaction is then terminated with 5 ml of methanol and the reaction mixture is concentrated to dryness. Final traces of pyridine are removed by azeotropic entrainment with toluene. The residue is taken up in 300 ml of DCM, washed with saturated aqueous KCl solution and H$_2$O and dried over Na$_2$SO$_4$. After removal of the solvent, the residue is chromatographed on silica gel (n-hexane/diethyl ether/TEA=40:60:1) (R. A. Jones *"Oligonucleotide Synthesis: A Practical Approach"* ed. M. J. Gait, IRL Press (1984) 23).

Yield: 4.9 g (79.3% of theory)

TLC (n-hexane/diethyl ether/TEA=40:60:1): $R_f$ value=0.42

MS (FD): m/z 618.2 ($M^+$), 303 ($DMT^+$)

$^1$H-NMR (CDCl$_3$): δ 0.80 (t), 1.20 (s), 1.96 (s), 2.36 (d), 2.72 (s), 3.27 (d), 3.32-3.48 (m), 3.75 (m), 6.61-6.76 (m), 7.08-7.37 (m)

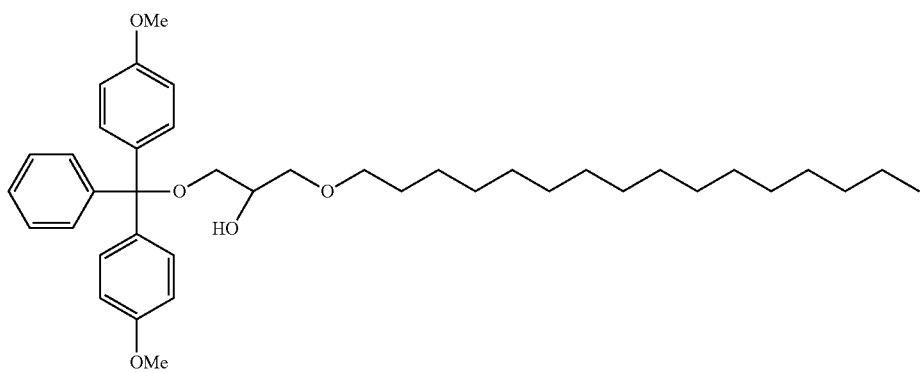 [SMILES: CCCCCCCCCCCCCCCCOCC(O)COC(c1ccccc1)(c1ccc(OC)cc1)c1ccc(OC)cc1]

17. Synthesis of [1-(4,4'-dimethoxytrityl)]-2-succinyl-3-hexadecylglycerol (Pam4)

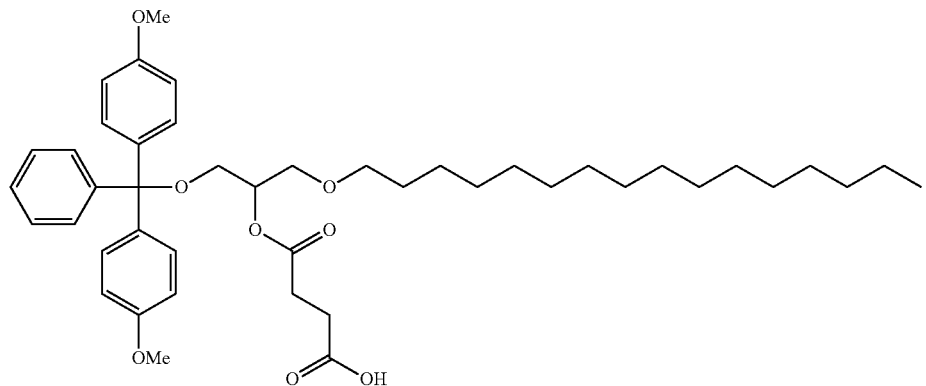 [SMILES: CCCCCCCCCCCCCCCCOCC(COC(c1ccccc1)(c1ccc(OC)cc1)c1ccc(OC)cc1)OC(=O)CCC(=O)O]

Procedure:

1.26 mmol of Pam3 (0.78 g) are dried twice with pyridine. 0.76 mmol of DMAP (92 mg) and 1.26 mmol of succinic anhydride (126 mg) are added to a solution of the alcohol in 5 ml of pyridine$_{abs}$. After 12 hours' stirring at RT, the reaction solution is taken up in 30 ml of DCM, washed twice with 30 ml of water and dried over $Na_2SO_4$. After removal of the solvent, the residue is chromatographed on silica gel (ethyl acetate/methanol/$NH_3$ (25% in $H_2O$)=5:1:1) (D. W. Will, T. Brown *Tetrahedron Lett.* 33 (1992) 2729.).

Yield: 0.6 g (66.3%)

TLC (EtOAc/MeOH/$NH_3$($H_2O$)=5:1:1): $R_f$ value=0.32

MS (FD): m/z 718 ($M^+$), 303 ($DMT^+$), 1020.7 $(M+DMT)^+$

18. Stimulation of Human Cells with an Adjuvant According to the Invention in the Form of a Lipid-Modified Nucleic Acid a) In order to determine the immunogenic activity of nucleic acids according to the invention in the form of adjuvants, lipid-modified nucleic acids containing a sequence according to SEQ ID NO: 1, 2, 3, 4 or 5 were co-incubated with human cells. To this end, human PBMC cells, for example, were co-incubated for 16 hours in X-VIVO-15 medium (BioWhittaker, catalogue no. BE04-418Q), enriched with 2 mM L-glutamine (BioWhittaker), 10 U/ml penicillin (BioWhittaker) and 10 µg/ml streptomycin, with 10 µg/ml of RNA (mRNA coding for β-galactosidase or a nucleic acid of formula (I) according to the invention which had been lipid-modified) and optionally with 10 µg/ml protamine. The supernatants were removed and the release of IL-6 and TNFα was analysed by means of ELISA.

b) In a further experiment, the release of TNF-α by human PBMC cells was determined after stimulation with RNA oligonucleotides used according to the invention (see above) and also adjuvants used according to the invention.

To that end, human PBMC cells were co-incubated for 16 hours with 10 µg/ml of RNA oligonucleotides in X-VIVO 15 medium (BioWhittaker), enriched with 2 mM L-glutamine (BioWhittaker), 10 U/ml penicillin (BioWhittaker) and 10 µg/ml streptomycin.

The supernatants were removed and analysed by means of ELISA.

19. Release of TNFalpha in hPBMCs

Figure 8:
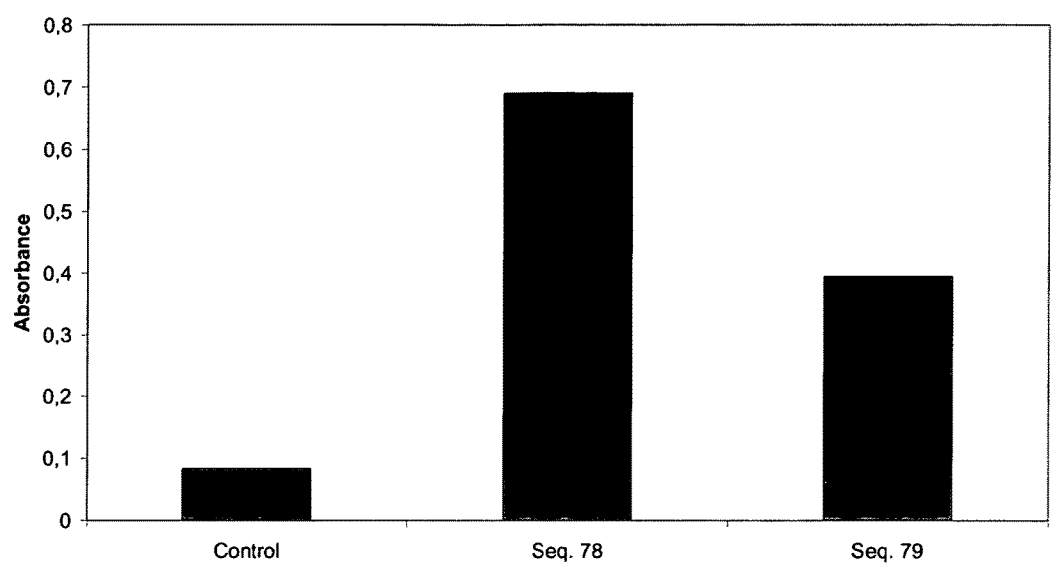
FIG. 8: shows the stimulation of human PBMCs (hPB-MCs) with oligonucleotides according to the invention of SEQ ID NOs: 78 and 79 (formula (I)). A stimulation can be observed most clearly in the case of SEQ ID NO: 78 and also for SEQ ID NO: 79.
Figure 9:
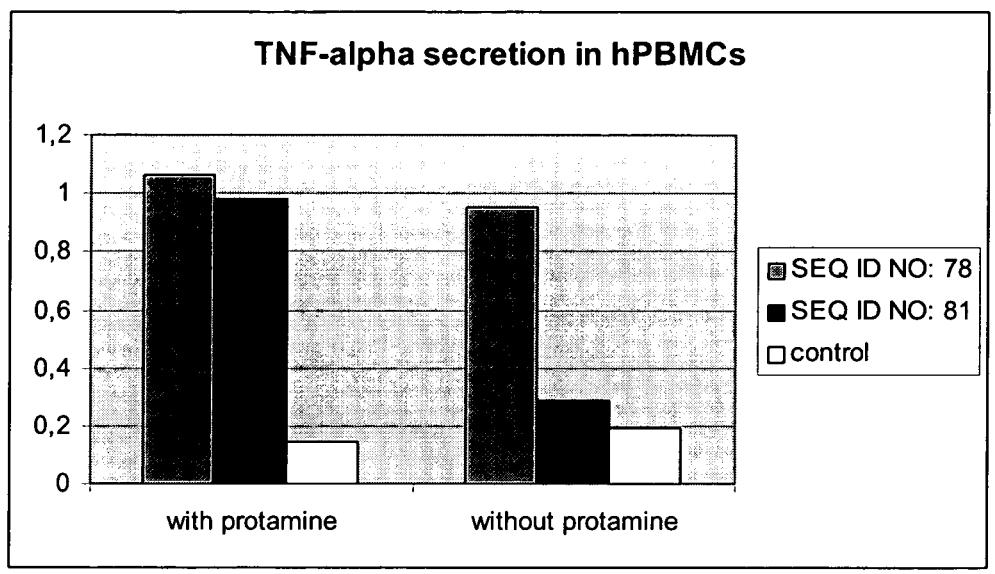
FIG. 9: depicts the stimulation of human PBMCs (hPB-MCs) with oligonucleotides according to the invention of SEQ ID NOs: 78 (formula (I)) and 81 (formula (II)) with and without protamin. A better stimulation can be observed most clearly with protamin in the case of SEQ ID NO: 81. Surprisingly, in the case of SEQ ID NO: 78 a similar stimulation can be observed with and without protamin (see FIG. 9).
Figure 10:
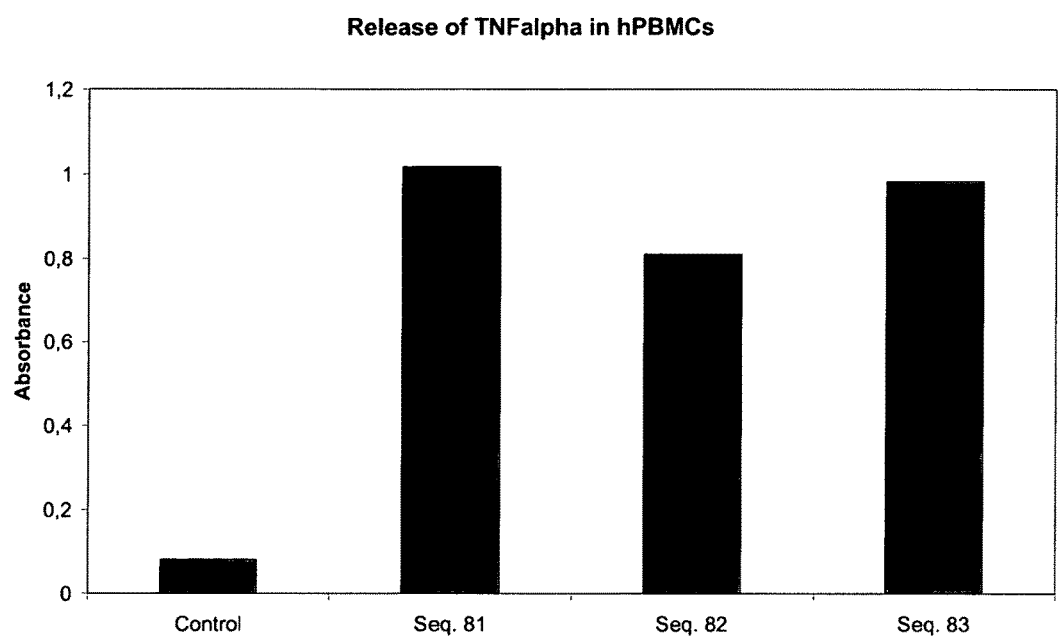
FIG. 10: shows the stimulation of human PBMCs (hPB-MCs) with oligonucleotides according to the invention of SEQ ID NOs: 81, 82 and 83 (formula (II)). A significant stimulation can be observed most clearly in each case, i.e. for SEQ ID NOs: 81, 82 and 83.
Figure 11:
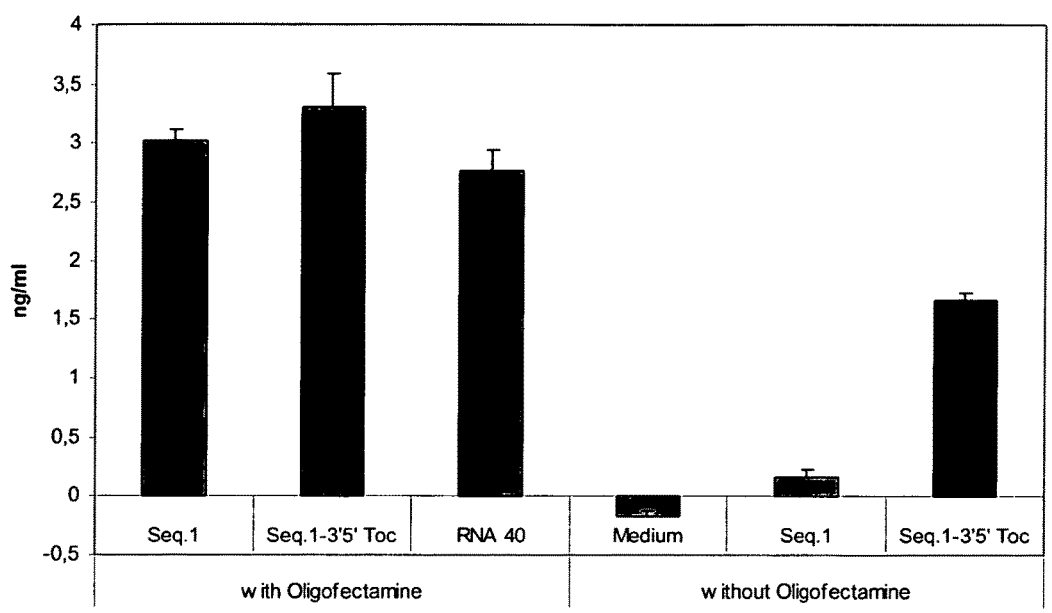
FIG. 11: depicts the release of TNFalpha after stimulation of human PBMCs (hPBMCs) with oligonucleotides according to formula (I) of the invention. Transfection was carried out with and without oligofectamine. Sequences transfected with oligofectamine were a) SEQ ID NO: 1 (Seq. 1), b) SEQ ID NO: 1 modified 3'5' with Tocopherol as a comparison b) RNA40 (SEQ ID NO: 87); Sequences transfected without oligofectamine were d) Medium (no sequence), e) SEQ ID NO: 1 (Seq. 1) and f) SEQ ID NO: 1 modified 3'5' with Tocopherol. Best results were obtained when transfecting SEQ ID NO: 1 (Seq. 1), SEQ ID NO: 1 modified 3'5' with Tocopherol along with oligofectamine. As a result, tocopherol increases the transfection of the RNA and thereby increases immuno-stimulation.

Human PBMCs were seeded on a 96 well microtiter plate ($2\times10^5$ in 200 µl per well) in serum free medium. Aqueous RNA-solutions (either complexed or non-complexed with protamine) were added to the cells (final RNA concentration: 10 µg/ml (in 33 µl)), thoroughly mixed and incubated at 37° C. for 24 h. The TNFalpha secretion was measured in the cell free cell supernatants using ELISA. The experiments were carried out in triplicate.

a) In a first experiment, stimulation of human PBMCs (hPBMCs) with oligonucleotides according to the invention of SEQ ID NOs: 78 and 79 (formula (I)) was measured. A stimulation can be observed most clearly in the case of SEQ ID NO: 78 and also for SEQ ID NO: 79 (see FIG. 8).

b) In a second (comparative) experiment, stimulation of human PBMCs (hPBMCs) was tested with oligonucleotides according to the invention of SEQ ID NOs: 78 (formula (II)) and 81 (formula (II)) with or without protamin. A better stimulation can be observed most clearly with protamin in the case of SEQ ID NO: 81. Surprisingly, in the case of SEQ ID NO: 78, a similar stimulation can be observed with and without protamin (see FIG. 9).

b) In a third experiment, stimulation of human PBMCs (hPBMCs) was tested with oligonucleotides according to the invention of SEQ ID NOs: 81, 82 and 83 (formula (II)) was measured. A significant stimulation can be observed most clearly in each case, i.e. for SEQ ID NOs: 81, 82 and 83 (see FIG. 10).

20. Release of TNFalpha in hPBMCs—Transfection Based on Complexation with and Without Oligofectamine Human PBMCs were seeded on a 96 well microtiter plate ($2\times10^5$ in 200 µl per well) in serum free medium. RNA solutions or solutions of RNA complexed with oligofectamine were added to the cells (final RNA concentration: 10 µg/ml), thoroughly mixed and incubated at 37° C. for 24 h. The TNF secretion was measured in the cell free cell supernatants using ELISA. Sequences transfected based on complexation with oligofectamine were a) SEQ ID NO: 1 (Seq. 1), b) SEQ ID NO: 1 modified 3'5' with Tocopherol as a comparison b) RNA40 (SEQ ID NO: 87); Sequences transfected (without oligofectamine complexation) were d) Medium (no sequence), e) SEQ ID NO: 1 (Seq. 1) and f) SEQ ID NO: 1 modified 3'5' with Tocopherol. Best results were obtained when transfecting SEQ ID NO: 1 (Seq. 1), SEQ ID NO: 1 modified 3'5' with Tocopherol along with oligofectamine. The experiments were carried out in triplicate.

21. Systemic Release of IL-12 in hPBMCs after I.V. (Intraveneous) Injection

Figure 12:
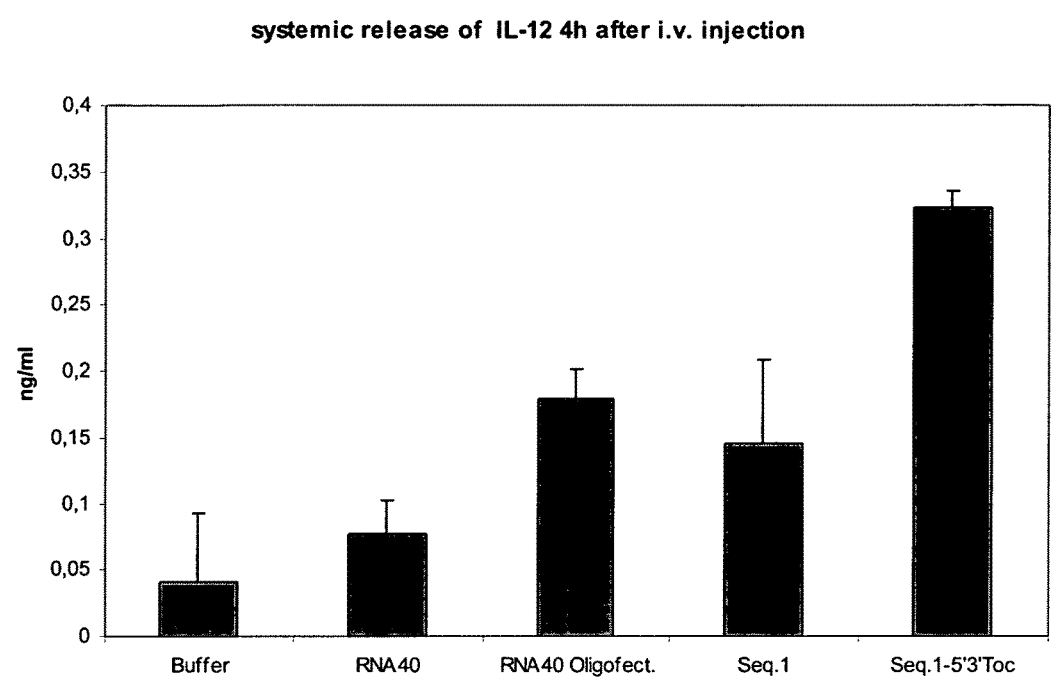
FIG. 12: depicts the systemic release of IL-12 after i.v. (intravenous) injection with oligonucleotides according to formula (I) of the invention. The graph shows the result of transfection with a) buffer as a control, b) RNA40 (SEQ ID NO: 87), c) RNA40 (SEQ ID NO: 87) complexed with oligofectamine, d) SEQ ID NO: 1 (Seq. 1) and e) SEQ ID NO: 1 modified 3'5' with Tocopherol. As can be seen from the graph, best results and thus significant immune-stimuation was obtained with inventive SEQ ID NO: 1 modified 5'3' with Tocopherol.

10 μg RNA in 100 μl Ringer-Lactate solution was i.v. administered. 4 h after administration, blood was taken was the patient and serum cytokine levels were determined. FIG. 12 shows the result of transfection with a) buffer as a control, b) RNA40 (SEQ ID NO: 87), c) RNA40 (SEQ ID NO: 87) complexed with oligofectamine, d) SEQ ID NO: 1 (Seq. 1) and e) SEQ ID NO: 1 modified 3'5' with Tocopherol. As can be seen from the graph, best results and thus significant immune stimuation was obtained with inventive SEQ ID NO: 1 modified 5'3' with Tocopherol.

22. Release of TNFalpha in hPBMCs—Using Different Modified SEQ ID NOS: 1

Figure 13:
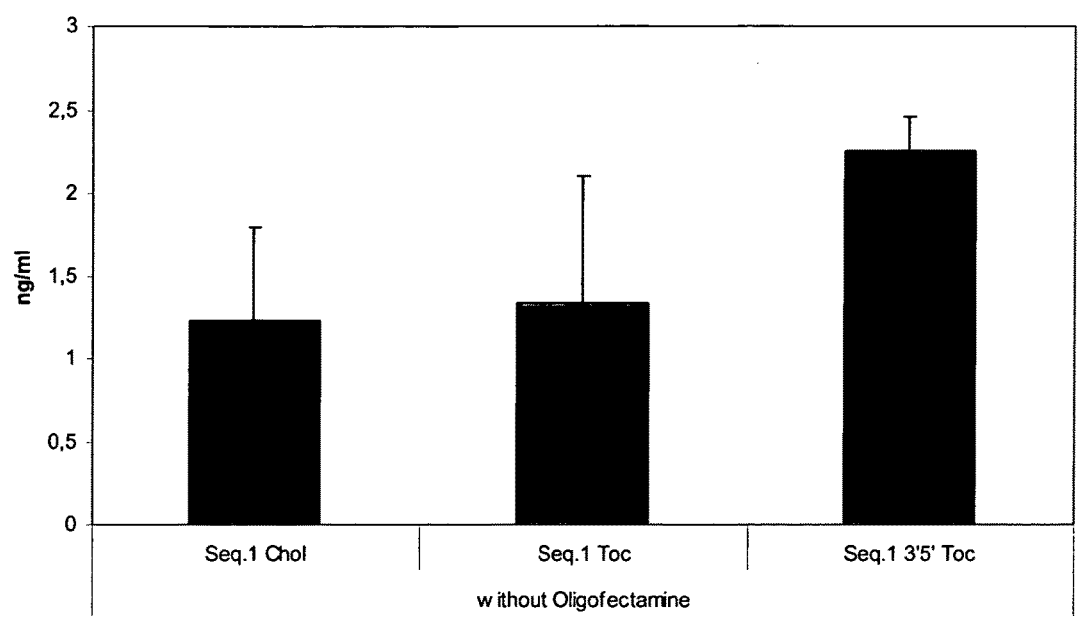
FIG. 13: describes a comparative experiment and shows the effect of different modifications of the inventive sequence according to SEQ ID NO: 1 on immune stimulation of human PBMCs (hPBMCs) and release of TNFalpha. SEQ ID NO: 1 (formula (I)) modified with Cholesterol, SEQ ID NO: 1 (formula (I)) modified with Tocopherol, and SEQ ID NO: 1 modified 3'5' with Tocopherol were used in the experiment, wherein best results were obtained with latter modification. However, modifications of to SEQ ID NO: 1 with either Cholesterol or Tocopherol also lead to significant stimulation of hPBMCs.

Again, human PBMCs were seeded on a 96 well microtiter plate ($2\times10^5$ in 200 μl per well) in serum free medium. 10 μl RNA solutions (RNA complexed with oligofectamine or without addition of oligofectamine) were added to the cells (final RNA concentration: 10 μg/ml), thoroughly mixed and incubated at 37° C. for 24 h. The TNF secretion was measured in the cell free cell supernatants using ELISA. In the comparative Experiment the effect of different modifications of the inventive sequence according to SEQ ID NO: 1 on immune stimulation of human PBMCs (hPBMCs) and release of TNFalpha was measured. SEQ ID NO: 1 (formula (I)) modified with Cholesterol, SEQ ID NO: 1 (formula (I)) modified with Tocopherol, and SEQ ID NO: 1 modified 3'5' with Tocopherol were used in the experiment, wherein best results were obtained with latter modification. However, modifications of to SEQ ID NO: 1 with either Cholesterol or Tocopherol also lead to significant stimulation of hPBMCs (see FIG. 13).

23. Reduction of Tumor Size after Prophylactic Vaccination with Ovalbumin and Inventive Oligonucleotides 6-8 week old C57/B16 mice were vaccinated with 10 μl protein (chicken ovalbumine) subcutaneously in the flank. Protein (chicken ovalbumine) and if applicable oligonucleotides was dissolved in IFA (incomplete Freud's adjuvant) and a total volume of 100 μl was used per injection. The solutions contained a) IFA, b) IFA and chicken ovalbumine, c) IFA and chicken ovalbumine and RNA40 (SEQ ID NO: 87), and d) IFA and chicken ovalbumine and the inventitive sequence SEQ ID NO: 1 when complexed with protamine, according to the following scheme:

|  | IFA | Protein (chicken Ovalbumine) | Protein + RNA 40 | Protein + RNA Seq. 1 + Protamine |
|---|---|---|---|---|
| Per mouse | 100 μl PBS | 10 μg Protein IFA | 10 μg Protein 50 μg RNA IFA | 10 μg Protein 50 μg RNA IFA |

Then, mice were boosted 10 days later with the same vaccination cocktail. 12 days after the boost, mice were challenged with $1\times10^6$ tumor cells (EG7.Ova) and tumour size was measured every day for 2 weeks.

Figure 14:
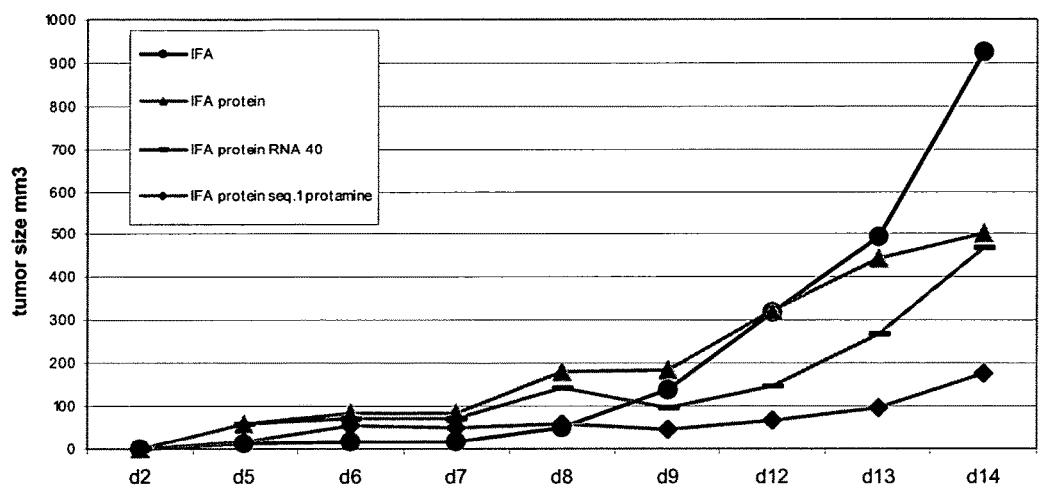
FIG. 14: shows the effect of the vaccination on tumor size using a) IFA, b) IFA and chicken ovalbumine, c) IFA and chicken ovalbumine and RNA40 (SEQ ID NO: 87), and d) IFA and chicken ovalbumine and the inventitive sequence SEQ ID NO: 1, when complexed with protamine. Best results, i.e. a significant reduction in tumour size, were obtained with IFA and chicken ovalbumine and the inventitive sequence SEQ ID NO: 1 (a)), indicating that inventive sequences exhibit superior adjuvant properties.

Best results, i.e. a significant reduction in tumour size, were obtained with IFA and chicken ovalbumine and the inventitive sequence SEQ ID NO: 1 (a)), indicating that inventive sequences exhibit superior adjuvant properties (see FIG. 14).

24. Reduction of Tumor Size after Intratumoral Injection

On day 0, mice $1\times10^6$ tumor cells (EG7.Ova) were implanted subcutaneously in the flank of 6-8 week old C57/B16 mice. On day 3, the treatment was started. 50 μg of RNA was diluted in PBS and a total volume of 100 μl was injected into the vicinity of the tumour. Treatment and measurement of tumour size were performed daily. When tumour size reached a volume of more than 160 mm$^3$, mice were sacrificed. 4 mice per group were treated and the shown values represent the medium values of 4 mice. For intratumoral injection a) PBS alone, b) the inventitive sequence SEQ ID NO: 1 (Seq. 1) modified 3'5' with Tocopherol in PBS, c) the inventitive sequence SEQ ID NO: 1 in PBS, and d) RNA40 (SEQ ID NO: 87) in PBS were used according to following protocol:

|  | PBS | RNA Seq. 1 5'3' Toc | RNA Seq. 1 | RNA 40 |
|---|---|---|---|---|
| Per mouse | 100 μl PBS | 50 μg RNA PBS | 50 μg RNA PBS | 50 μg RNA PBS |

Figure 15:
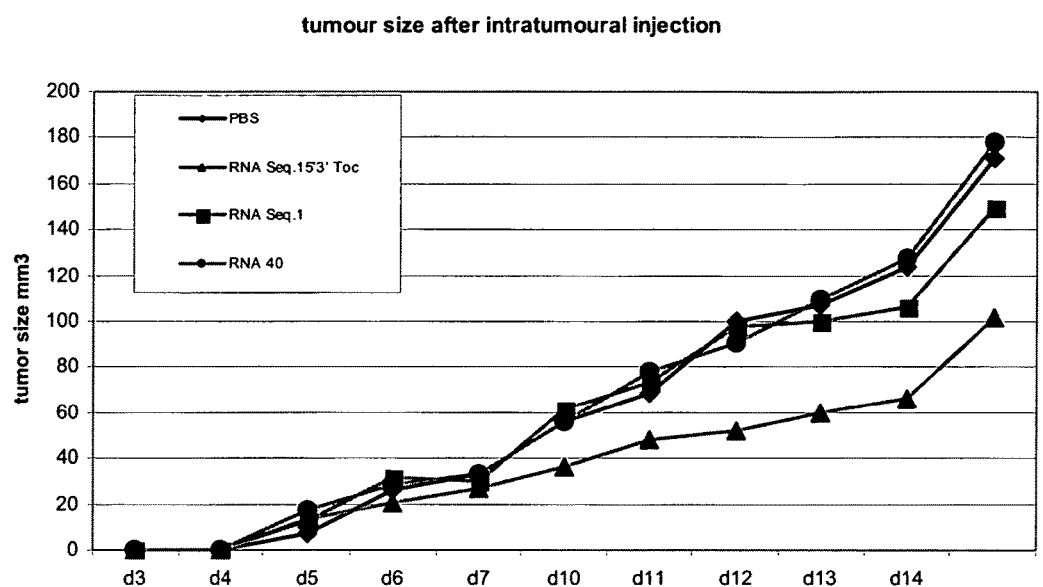
FIG. 15: depicts the effect of intratumoral injection on tumor size using a) PBS alone, b) the inventive sequence SEQ ID NO: 1 modified 3'5' with Tocopherol in PBS, c) the inventive sequence SEQ ID NO: 1 in PBS, and d) RNA40 (SEQ ID NO: 87) in PBS. Best results, i.e. a significant reduction in tumour size, were obtained with the inventive sequence SEQ ID NO: 1 modified 3'5' with Tocopherol followed by the unmodified inventive sequence SEQ ID NO: 1.

Best results, i.e. a significant reduction in tumour size, were obtained with the inventitive sequence SEQ ID NO: 1 modified 3'5' with Tocopherol followed by the unmodified inventitive sequence SEQ ID NO: 1 (see FIG. 15).

ADVANTAGES OF THE INVENTION

A nucleic acid of the general formula (I): $G_lX_mG_n$, or in the form of a nucleic acid of the general formula (II): $C_lX_mC_n$ according to the invention may be used as immune-stimulating agent as such. Preferably, the nucleic acid of the invention contains a lipid modification and may be used as such (e.g. dissolved in a pharmaceutically active carrier or vehicle). Thereby, the inventive nucleic acids stimulate the innate immune system and eleicit an unspecific immune response. This immunstimulating property may well be enhanced by the addition of other compounds known in the art as actively stimulating the innate immune response to the inventive nucleic acids. For example, according to the invention, a 3'-cholesterol-modified phosphodiester oligonucleotide has been disclosed as an immune-stimulating adjuvant that is able to induce a cytotoxic effect on specific tumour cells. This surprising effect is based substantially on an immune-stimulating action of the optionally lipid modified nucleic acid of the general formula (I) or (II) according to the invention that is used, the nature of the 3' or 5' modification (lipid modification) playing an important role. In summary, the immune-stimulating properties of nucleic acids according to general formula (I) or (II) render these molecules effective as therapeutics for eliciting an unspecific immune-stimulatory response either by their own (immune-stimulating agent) or—as an adjuvant—in combination with other pharmaceutically active components, which are typically immune-stimulatory components activating a specific immune response directed towards the pharmaceutically active compound.

The invention claimed is:

1. A method of stimulating an immune response to a disease antigen, comprising administering to a patient in need thereof a composition comprising:
   (a) the disease antigen or nucleic acid encoding a disease antigen; and
   (b) a pharmaceutically effective amount of an adjuvant nucleic acid, wherein the adjuvant nucleic acid comprises at least one adjuvant nucleic acid sequence selected from the following sequences:

```
GGUUUUUUUUUUUUUUGGG;                        (SEQ ID NO: 1)
GGGGGUUUUUUUUUUGGGGG;                        (SEQ ID NO: 2)
GGGGGUUUUUUUUUUUUUUUUUUUUUUUUUUUGGGGG;       (SEQ ID NO: 3)
GUGUGUGUGUGUUUUUUUUUUUUUUUGUGUGUGUGUGU;      (SEQ ID NO: 4)
GGUUGGUUGGUUUUUUUUUUUUUUUUGGUUGGUUGGUU;      (SEQ ID NO: 5)
GGGGGGUUUUUUUUGGGGGG;                        (SEQ ID NO: 10)
GGGGGGUUUUUUUUUGGGGG;                        (SEQ ID NO: 11)
GGGGGGUUUUUUUUUUGGGG;                        (SEQ ID NO: 12)
GGGGGUUUUUUUUUUUGGGG;                        (SEQ ID NO: 13)
GGGGGGUUUUUUUUUUUGGG;                        (SEQ ID NO: 14)
GGGGUUUUUUUUUUUUUGGG;                        (SEQ ID NO: 15)
GGGGUUUUUUUUUUUUUUGG;                        (SEQ ID NO: 16)
GGUUUUUUUUUUUUUUUUGG;                        (SEQ ID NO: 17)
GUUUUUUUUUUUUUUUUUUG;                        (SEQ ID NO: 18)
GGGGGGGUUUUUUUGGGGGGG;                       (SEQ ID NO: 23)
GGGGGGGUUUUUUUUGGGGGGG;                      (SEQ ID NO: 24)
GGGGGGGUUUUUUUUUGGGGG;                       (SEQ ID NO: 25)
GGGGGGUUUUUUUUUUGGGGG;                       (SEQ ID NO: 26)
GGGGGGUUUUUUUUUUUGGGG;                       (SEQ ID NO: 27)
GGGGGUUUUUUUUUUUUGGGG;                       (SEQ ID NO: 28)
GGGGGUUUUUUUUUUUUUGGG;                       (SEQ ID NO: 29)
GGGUUUUUUUUUUUUUUUGGG;                       (SEQ ID NO: 30)
GGUUUUUUUUUUUUUUUUUGG;                       (SEQ ID NO: 31)
GGGGGGGGUUUUUUUGGGGGGGG;                     (SEQ ID NO: 36)
GGGGGGGGUUUUUUUUGGGGGGG;                     (SEQ ID NO: 37)
GGGGGGGGUUUUUUUUUGGGGGG;                     (SEQ ID NO: 38)
GGGGGGGUUUUUUUUUUGGGGGG;                     (SEQ ID NO: 39)
GGGGGGGUUUUUUUUUUUGGGGG;                     (SEQ ID NO: 40)
GGGGGGUUUUUUUUUUUUGGGGG;                     (SEQ ID NO: 41)
GGGGGGUUUUUUUUUUUUUGGGG;                     (SEQ ID NO: 42)
GGGGUUUUUUUUUUUUUUUGGGG;                     (SEQ ID NO: 43)
GGGUUUUUUUUUUUUUUUUUGGG;                     (SEQ ID NO: 44)
GUUUUUUUUUUUUUUUUUUUUUUUUUUUUG;              (SEQ ID NO: 45)
GGUUUUUUUUUUUUUUUUUUUUUUUUUUUUGG;            (SEQ ID NO: 46)
GGGUUUUUUUUUUUUUUUUUUUUUUUUUUUUGGG;          (SEQ ID NO: 47)
GGGGUUUUUUUUUUUUUUUUUUUUUUUUUUUUGGGG;        (SEQ ID NO: 48)
GGGGGUUUUUUUUUUUUUUUUUUUUUUUUUUUUGGGGG;      (SEQ ID NO: 49)
GGGGGGUUUUUUUUUUUUUUUUUUUUUUUUUUUUGGGGGG;    (SEQ ID NO: 50)
GGGGGGGUUUUUUUUUUUUUUUUUUUUUUUUUUUUGGGGGGG;  (SEQ ID NO: 51)
GGGGGGGGUUUUUUUUUUUUUUUUUUUUUUUUUUUUGGGGGGGG;(SEQ ID NO: 52)
GGGGGGGGGUUUUUUUUUUUUUUUUUUUUUUUUUUUUGGGGGGGGG;(SEQ ID NO: 53)
GGUUUUUUUUGG;                                (SEQ ID NO: 59)
GGUUUUUUUUUGG;                               (SEQ ID NO: 60)
GGUUUUUUUUUUGG;                              (SEQ ID NO: 61)
GGUUUUUUUUUUUGG;                             (SEQ ID NO: 62)
GGUUUUUUUUUUUUGG;                            (SEQ ID NO: 63)
GGUUUUUUUUUUUUUGG;                           (SEQ ID NO: 64)
GGUUUUUUUUUUUUUUGG;                          (SEQ ID NO: 65)
GGUUUUUUUUUUUUUUUGG;                         (SEQ ID NO: 66)
```

-continued

GGGUUUUUUUUGGG;  (SEQ ID NO: 72)

GGGUUUUUUUUUGGG;  (SEQ ID NO: 73)

GGGUUUUUUUUUGGG;  (SEQ ID NO: 74)

GGGUUUUUUUUUUGGG;  (SEQ ID NO: 75)

GGGUUUUUUUUUUUGGG;  (SEQ ID NO: 76)

GGGUUUUUUUUUUUUGGG;  (SEQ ID NO: 77)

GGGUUUUUUUUUUUUUUUGGGUUUUUUUUUUUUUUGGGUUUUUUUUUUUUUUGGG;  (SEQ ID NO: 78)

GGGUUUUUUUUUUUUUUUGGGGGGUUUUUUUUUUUUUUUGGG; and  (SEQ ID NO: 79)

wherein the immune response to the disease antigen or disease antigen nucleic acid is greater than if the patient was provided the disease antigen or disease antigen nucleic acid without the adjuvant nucleic acid.

2. The method according to claim 1, wherein the adjuvant nucleic acid has a length of 15 to 100 nucleotides.

3. The method according to claim 1, wherein the adjuvant nucleic acid is RNA or DNA.

4. The method according to claim 1, wherein the adjuvant nucleic acid is single-stranded RNA.

5. The method according to claim 1, wherein at least one nucleotide of the adjuvant nucleic acid is a non-naturally occurring analogue of a naturally occurring nucleotide selected from 1-methyl-adenosine, 2-methyl-adenosine, 2-methylthio-N6-isopentenyl-adenosine, N6-methyl-adenosine, N6-isopentenyl-adenosine, 2-thio-cytidine, 3-methyl-cytidine, 4-acetyl-cytidine, 2,6-diaminopurine, 1-methyl-guanosine, 2-methyl-guanosine, 2,2-dimethyl-guanosine, 7-methyl-guanosine, inosine, 1-methyl-inosine, dihydro-uridine, 4-thio-uridine, 5-carboxymethylaminomethyl-2-thio-uridine, 5-(carboxyhydroxylmethyl)-uridine, 5-fluoro-uridine, 5-bromo-uridine, 5-carboxymethylaminomethyl-uridine, 5-methyl-2-thio-uridine, N-uridine-5-oxyacetic acid methyl ester, 5-methylaminomethyl-uridine, 5-methoxyaminomethyl-2-thio-uridine, 5'-methoxycarbonylmethyl-uridine, 5-methoxy-uridine, uridine-5-oxyacetic acid methyl ester, uridine-5-oxyacetic acid (v), queosine, beta-D-mannosyl-queosine, and wybutoxosine.

6. The method according to claim 1, wherein the adjuvant nucleic acid is an RNA and additionally has at the 5' terminus a cap structure and/or at the 3' terminus a poly-A tail.

7. The method according to claim 1, wherein the adjuvant nucleic acid contains a lipid modification.

8. The method according to claim 7, wherein the lipid-modified nucleic acid comprises the adjuvant nucleic acid, at least one linker covalently linked with the adjuvant nucleic acid, and a lipid covalently linked with the linker.

9. The method according to claim 7, wherein the lipid-modified nucleic acid comprises at least one bifunctional lipid covalently linked with the adjuvant nucleic acid.

10. The method according to claim 7, wherein the lipid-modified nucleic acid comprises at least one linker covalently linked with the nucleic acid and at least one lipid covalently linked with the linker, and at least one bifunctional lipid covalently linked with the adjuvant nucleic acid.

11. The method according to claim 7, wherein the lipid-modified nucleic acid contains 3 to 8 lipids per nucleic acid, wherein:
   a) all the lipids are covalently linked with the adjuvant nucleic acid via a linker;
   b) all the lipids are covalently linked directly with the adjuvant nucleic acid; or
   c) at least one of the lipids are covalently linked with the adjuvant nucleic acid via a linker and at least one of the lipids are covalently linked directly with the adjuvant nucleic acid.

12. The method according to claim 7, wherein the lipid comprises—vitamins, α-tocopherol, RRR-α-tocopherol, L-α-tocopherol, racemate D,L-α-tocopherol, vitamin A, retinoic acid, retinol, vitamin D, the ergosterol precursors of vitamin D, vitamin E, vitamin E succinate (VES), vitamin K, quinone compounds, phytol compounds, steroids bile acids, cholic acid, deoxycholic acid, dehydrocholic acid, cortisone, digoxygenin, testosterone, cholesterol, thiocholesterol, polyalkylene glycols, aliphatic groups, $C_1$-$C_{20}$-alkanes, $C_1$-$C_{20}$-alkenes, $C_1$-$C_{20}$-alkanol compounds, dodecanediol, hexadecanol, undecyl residues, phospholipids, phosphatidylglycerol, diacylphosphatidylglycerol, phosphatidylcholine, dipalmitoylphosphatidylcholine, distearoylphosphatidylcholine, phosphatidylserine, phosphatidylethanolamine, di-hexadecyl-rac-glycerol, sphingolipids, cerebrosides, gangliosides, triethylammonium 1,2-di-O-hexadecyl-rac-glycero-3-H-phosphonate, polyamines, polyalkylene glycols, polyethylene glycol (PEG), hexaethylene glycol (HEG), palmitin residues, palmityl residues, octadecylamines residues, hexylamino-carbonyl-oxycholesterol residues, waxes, terpenes, alicyclic hydrocarbons, saturated fatty acid residues mono-unsaturated fatty acid residues or poly-unsaturated fatty acid residues.

13. The method according to claim 8, wherein the linker is selected from a compound that contains at least two, three or four reactive groups selected from a hydroxy group, an amino group and an alkoxy group.

14. The method according to claim 13, wherein the linker is selected from glycol, glycerol, glycerol derivatives, 2-aminobutyl-1,3-propanediol, 2-aminobutyl-1,3-propaoediol derivatives a 2-aminobutyl-1,3-propaoediol skeleton, pyrrolidine linkers or pyrrolidine-containing organic molecules.

15. The method according to claim 7, wherein the lipid modification is at the 3' and/or 5' end of the adjuvant nucleic acid.

16. The method according to claim 1, wherein the composition further comprises a pharmaceutically acceptable carrier and at least one auxiliary substance, additive, and/or adjuvant.

17. The method according to claim 16, wherein the adjuvant is an immune-stimulating agent selected from the group consisting of cationic peptides and cationic polysaccharides.

18. The method according to claim 1, wherein the composition further comprises at least one additional disease antigen component, a pharmaceutically acceptable carrier and at least one auxiliary substance, additive, and/or adjuvant.

19. The method according to claim 18, wherein the at least one disease antigen component is selected from the group consisting of peptides, proteins, nucleic acids, therapeutically active low molecular weight organic or inorganic compounds having a molecular weight less than 5000, sugars, antigens, antibodies, pathogens, attenuated pathogens, de-activated pathogens, human cells, cellular fragments or fractions and other therapeutic agents, which are adapted to exhibit enhanced transfection properties by complexation with lipids and/or polycationic peptides.

20. The method according to claim 1, wherein the disease antigen is associated with a cancer selected from colon carcinomas, melanomas, renal carcinomas, lymphomas, acute myeloid leukaemia (AML), acute lymphoid leukaemia (ALL), chronic myeloid leukaemia (CML), chronic lymphocytic leukaemia (CLL), gastrointestinal tumours, pulmonary carcinomas, gliomas, thyroid tumours tumours, mammary carcinomas, prostate tumours, hepatomas, virus-induced tumours, adenocarcinomas, herpes virus-induced tumours, heptatitis B-induced tumours, HTLV-1- and HTLV-2-induced lymphomas, acoustic neuromas/neurinomas, cervical cancer, lung cancer, pharyngeal cancer, anal carcinomas, glioblastomas, rectal carcinomas, astrocytomas, brain tumours, stomach cancer, retinoblastomas, basaliomas, brain metastases, medulloblastomas, vaginal cancer, pancreatic cancer, testicular cancer, melanomas, thyroidal carcinomas, bladder cancer, Hodgkin's syndrome, meningiomas, Schneeberger disease, bronchial carcinomas, hypophysis tumour, Mycosis fungoides, oesophageal cancer, breast cancer, carcinoids, neurinomas, spinaliomas, Burkitt's lymphomas, laryngeal cancer, renal cancer, thymomas, corpus carcinomas, bone cancer, non-Hodgkin's lymphomas, urethral cancer, CUP syndrome, head/neck tumours, oligodendrogliomas, vulval cancer, intestinal cancer, colon carcinomas, oesophageal carcinomas, wart involvement, tumours of the small intestine, craniopharyngeomas, ovarian carcinomas, soft tissue tumours/sarcomas, ovarian cancer, liver cancer, pancreatic carcinomas, cervical carcinomas, endometrial carcinomas, liver metastases, penile cancer, tongue cancer, gall bladder cancer, leukaemia, plasmocytomas, uterine cancer, lid tumour and prostate cancer.

21. The method according to claim 1, wherein the disease antigen is associated with an infectious disease that is viral, bacterial, or parasitic.

22. The method according to claim 1, wherein the disease antigen is associated with an autoimmune disease that is selected from the group consisting of type I autoimmune diseases, type II autoimmune diseases, type III autoimmune diseases, and type IV autoimmune diseases.

23. The method according to claim 1, wherein the disease antigen is associated with an allergy that is selected from the group consisting of allergic asthma, allergic conjunctivitis, allergic rhinitis, anaphylaxis, angioedema, atopic dermatitis, urticaria, eosinophilia, respiratory, allergies to insect stings, skin allergies, food allergies, and allergies to medicine.

24. The method of claim 1, wherein the disease antigen is a tumour antigen.

25. The method of claim 24, wherein the tumor antigen is a tumour specific surface antigen.

26. The method of claim 1, wherein the disease antigen nucleic acid is an mRNA.

27. The method of claim 26, wherein the mRNA has been modified such that it has been stabilized to reduce its susceptibility to degradation by exo- and/or endonucleases relative to wild type version.

28. The method of claim 26, wherein the mRNA has been modified such that it has an increased G/C content relative to its wild type version.

29. The method of claim 26, wherein the mRNA is associated with a cationic compound.

30. The method of claim 29, wherein the cationic compound is polycationic peptide or protein.

31. The method of claim 1, wherein the adjuvant nucleic acid activates or binds a Toll-like receptor (TLR).

32. The method of claim 31, wherein the TLR is a TLR7 and/or TLR8.

33. The method of claim 1, wherein the adjuvant nucleic acid activates an innate immune response.

* * * * *